US 9,734,290 B2

(12) United States Patent
Srinivas et al.

(10) Patent No.: US 9,734,290 B2
(45) Date of Patent: Aug. 15, 2017

(54) SYSTEM AND METHOD FOR EVIDENCE BASED DIFFERENTIAL ANALYSIS AND INCENTIVES BASED HEALTHCARE POLICY

(71) Applicants: Neela Srinivas, Cupertino, CA (US); Srinivas Kumar, Cupertino, CA (US)

(72) Inventors: Neela Srinivas, Cupertino, CA (US); Srinivas Kumar, Cupertino, CA (US)

( * ) Notice: Subject to any disclaimer, the term of this patent is extended or adjusted under 35 U.S.C. 154(b) by 115 days.

(21) Appl. No.: 15/080,061

(22) Filed: Mar. 24, 2016

(65) Prior Publication Data

US 2016/0203279 A1    Jul. 14, 2016

Related U.S. Application Data

(63) Continuation-in-part of application No. 13/328,011, filed on Dec. 16, 2011.

(51) Int. Cl.
| | | |
|---|---|---|
| *G06Q 40/00* | (2012.01) | |
| *G06F 19/00* | (2011.01) | |
| *G06Q 50/22* | (2012.01) | |
| *G06Q 40/08* | (2012.01) | |

(52) U.S. Cl.
CPC .......... *G06F 19/328* (2013.01); *G06F 19/322* (2013.01); *G06Q 40/08* (2013.01); *G06Q 50/22* (2013.01)

(58) Field of Classification Search
CPC ....... G06Q 40/00; G06Q 40/08; G06Q 20/102
See application file for complete search history.

(56) References Cited

U.S. PATENT DOCUMENTS

| | | | |
|---|---|---|---|
| 6,059,724 A | 5/2000 | Campell et al. | |
| 7,302,398 B2 | 11/2007 | Ban et al. | |
| 7,912,734 B2 | 3/2011 | Kil | |
| 8,224,665 B2 | 7/2012 | Morris | |

(Continued)

OTHER PUBLICATIONS

Y Claire Wang et al., "Health and economic burden of the projected obesity trends in the USA and the UK," Obesity 2, Aug. 27, 2011, pp. 815-825, vol. 378, http://tollieschmidt.com/wp-content/uploads/2011/10/lancet-obesity-2-health-and-economic-burden-of-the-projected-obesity-trends-in-the-usa-and-the-uk.pdf.

(Continued)

*Primary Examiner* — Lalita M Hamilton
(74) *Attorney, Agent, or Firm* — Buchanan Ingersoll & Rooney PC

(57) ABSTRACT

An on-demand and real-time evidence based cost modeling and predictive analysis system, and a financial incentives based plan to reduce healthcare costs. An analytics system that includes a data aggregator and regression models generates incremental expenditures among overweight and obese individuals, predictive forecasts of future medical costs, and predictive forecasts of cost reduction based on financial incentives to recipients. The forecasts may include interactions, personalized variables, statistical trends, prevalence of diseases based on body mass index and/or age, and medical evidence associated with specific illnesses. A computer-based program may process and analyze variables in healthcare records. A health insurance provider may provide an annual rebate on paid premiums to recipients based on a qualifying annual BMI as an incentive. The recipients may receive the rebates in a qualified Healthcare Individual Reimbursement Account (HIRA) managed by the recipients towards future healthcare related expenditures.

20 Claims, 28 Drawing Sheets

(56) References Cited

U.S. PATENT DOCUMENTS

| | | |
|---|---|---|
| 2001/0020229 A1 | 9/2001 | Lash |
| 2005/0228692 A1 | 10/2005 | Hodgdon |
| 2006/0129436 A1 | 6/2006 | Short |
| 2007/0050215 A1 | 3/2007 | Kil et al. |
| 2008/0147438 A1 | 6/2008 | Kil |
| 2009/0048877 A1 | 2/2009 | Binns et al. |
| 2009/0265190 A1 | 10/2009 | Ashley et al. |
| 2009/0326976 A1 | 12/2009 | Morris |
| 2012/0245953 A1 | 9/2012 | Morris |
| 2013/0144642 A1 | 6/2013 | Bessette |
| 2015/0081222 A1 | 3/2015 | Laing et al. |

OTHER PUBLICATIONS

M. Malach et al., "Further Opportunities for Cost Reduction of Medical Care," J Community Health, Springer Science+Business Media, LLC, published online Mar. 27, 2010, 11 pages http://w4.stern.nyu.edu/newsroom/docs/cost_reduction_medical_care_baumol.pdf.

Hearle, "Study of Healthcare Outpatient Cost Drivers," The Lewin Group, Inc., Oct. 16, 2002, 88 pages, http://tux.ingenix.com/NR/rdonlyres/EA065563-C913-44F5-96B8-1DBAF5AF6C82/0/oct2002outpatientcost2388.pdf.

Michael E. Chernew, "What Does the RAND Health Insurance Experiment Tell Us About the Impact of Patient Cost Sharing on Health Outcomes?," The American Journal of Managed Care, vol. 14, No. 7, Jul. 2008, pp. 412-414, www.ajmc.com.

Thomas Stohr, et al., "An Integrative and Uniform Model for Metadata Management in Data Warehousing Environments," 16 pages.

Teresa M. Waters et al., Impact of High-Deductible Health Plans on Health Care Utilization and Costs, Health Services Research, 46:1, part 1, Feb. 2011, pp. 155-172.

Eric S. Rosenberg et al., "Mathematical-Statistical Modeling to Inform the Design of HIV Treatment Strategies and Clinical Trials," Modeling for Design of HIV Treatment and Trials, NC State University, ENAR, powerpoint, 32 pages.

Anne M. Wolf et al., "Current Estimates of the Economic Cost of Obesity in the United States," Obesity Research, vol. 6, No. 2, Article first published online: Sep. 6, 2012, pp. 97-106.

Timothy Bungum et al., "The Relationship of Body Mass Index Medical Costs, and Job Absenteeism," American Journal of Health Behavior, Jul./Aug. 2003, 27, 4, ProQuest Central, pp. 456-462.

Eliot A. Cohen, "Net Assessment: An American Approach," JCSS Memorandum No. 29, Apr. 1990, 28 pages.

U.S. Appl. No. 14/753,728, filed Jun. 29, 2015 to Srinivas et al.

U.S. Appl. No. 15/062,970, filed Mar. 7, 2016 to Srinivas et al.

Duan, "A Comparison of Alternative Models for the Demand for Medical Care", The Rand Corporation; Jan. 1982.

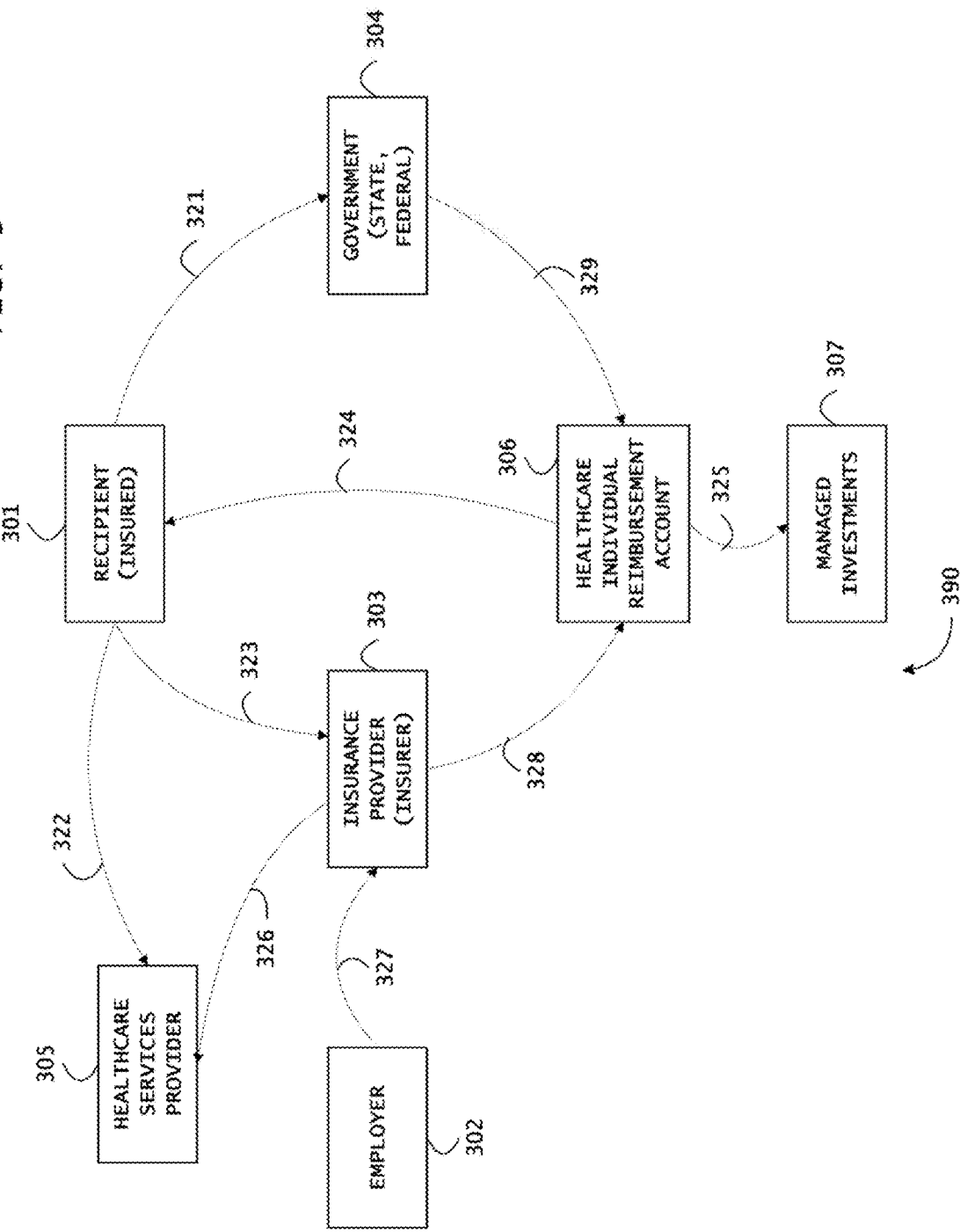

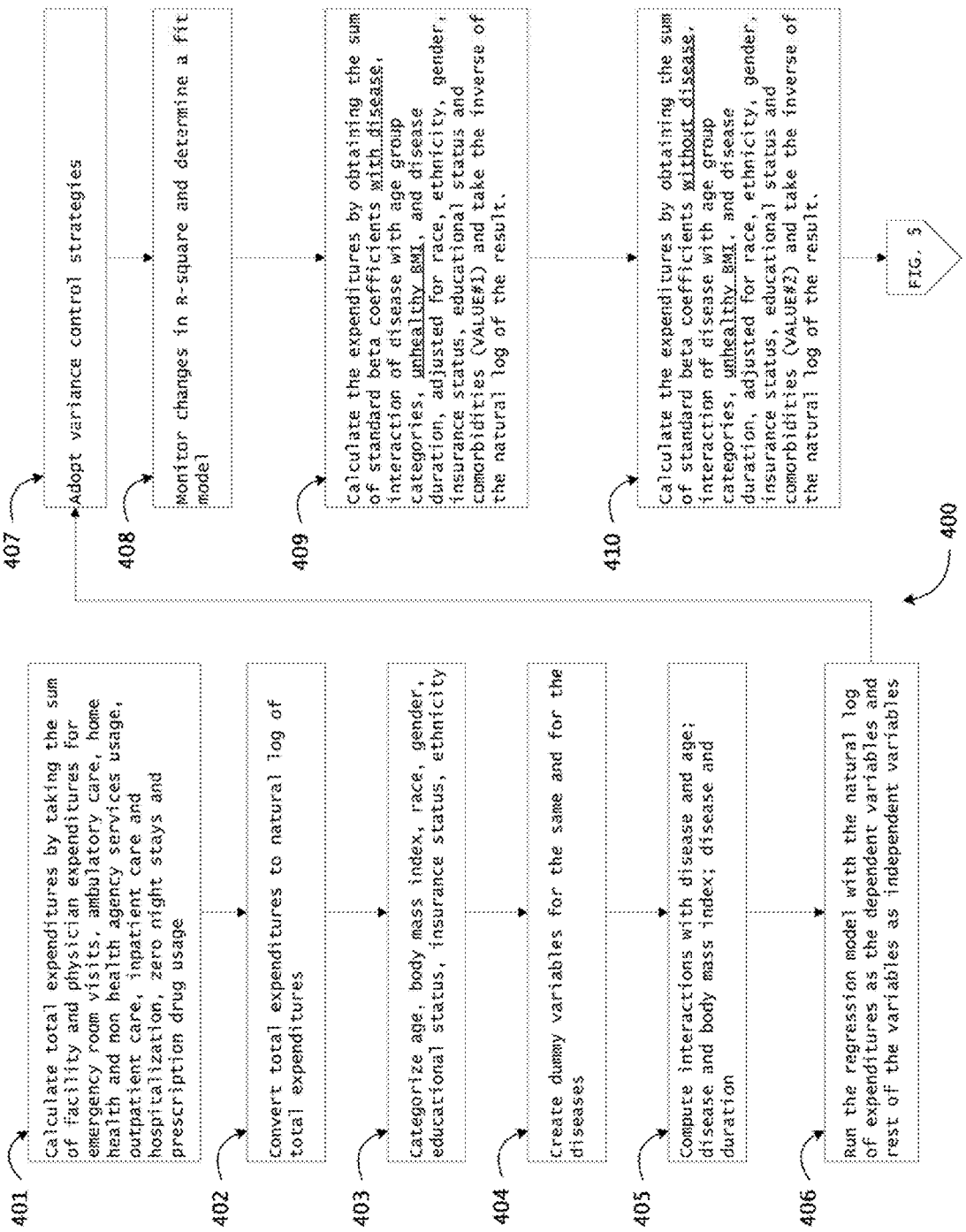

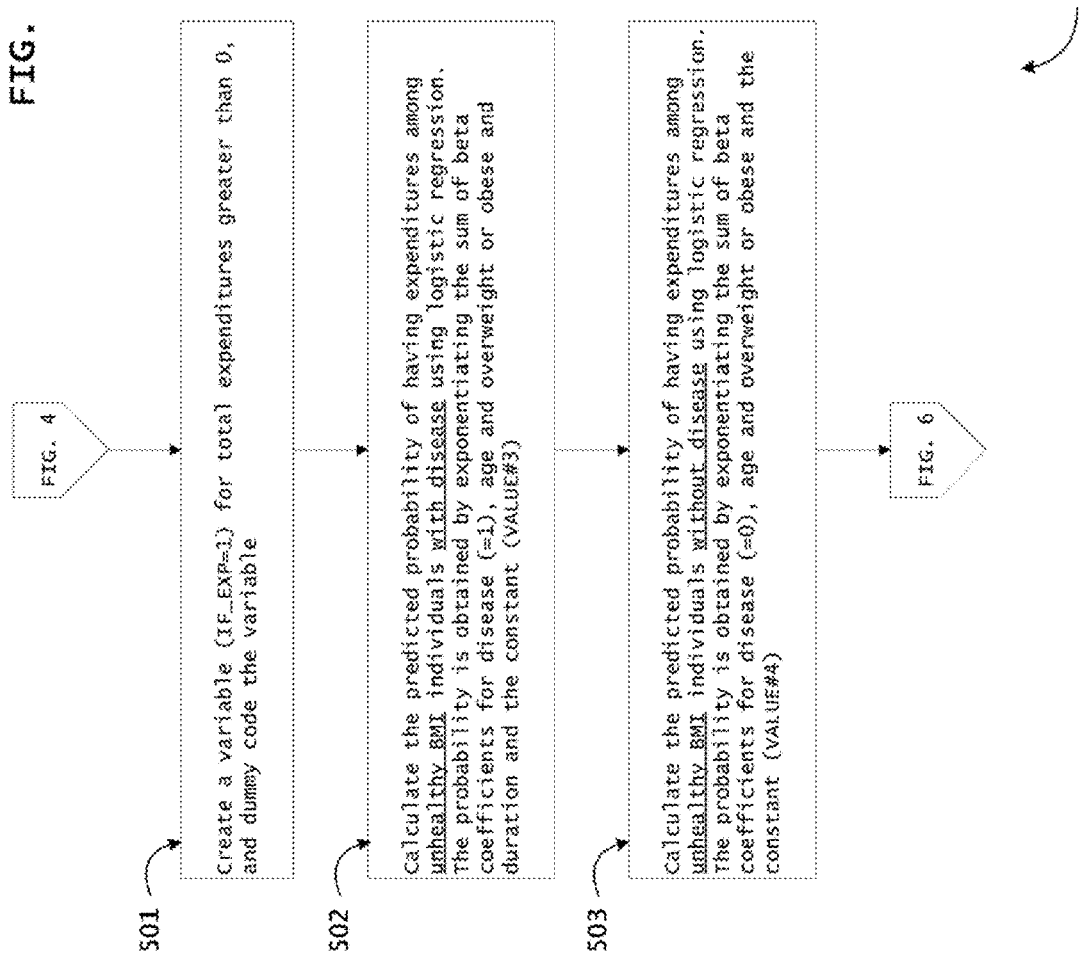

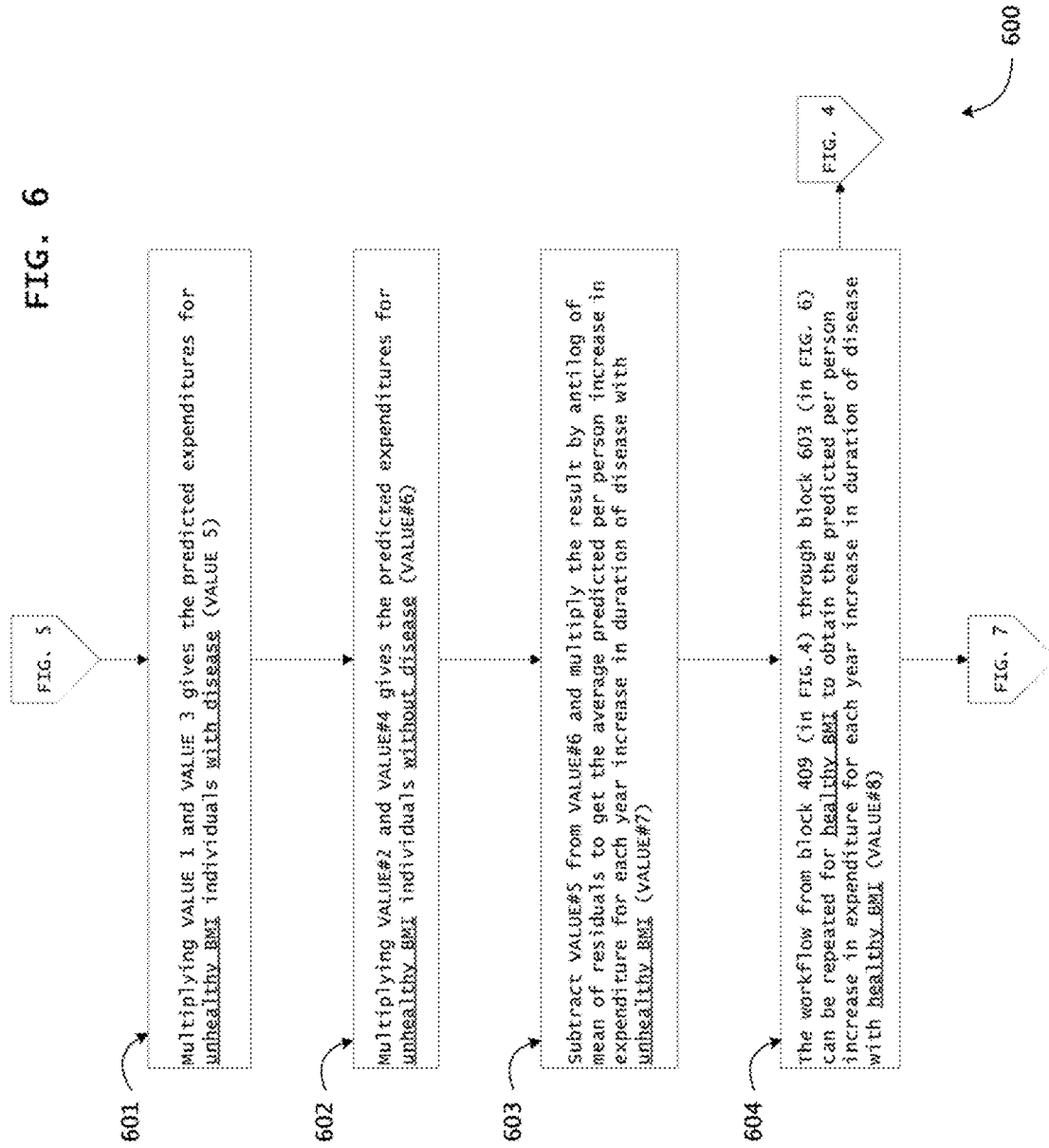

701 — To obtain estimated reduction in cost for unhealthy BMI individuals (on achieving a healthy BMI), subtract VALUE#7 from VALUE#8.

702 — Multiplying the average per person increase in expenditure for the unhealthy BMI population by the total number of unhealthy BMI individuals with the disease in the sample determines the total expenditures for the disease among unhealthy BMI population.

703 — Multiplying the average per person increase in expenditure for the healthy BMI population by the total number of healthy BMI individuals with the disease in the sample determines the total expenditures for the disease among the healthy BMI population.

704 — calculate the prevalence of individuals with limitations in activities of daily living, using variables such as difficulties in standing, walking, bending, reaching overhead, physical limitations in house work and in school, social limitations and cognitive limitations for individuals with unhealthy or healthy BMI.

705 — Prevalence of diseases among individuals by body mass index and age may be calculated.

706 — the annual healthcare premiums categorized by family income may be calculated.

707 — The average cost may also be modeled as a function of the discount rate, the survival probabilities of the individual with the health condition, and the average costs for the individual with each year past onset of disease.

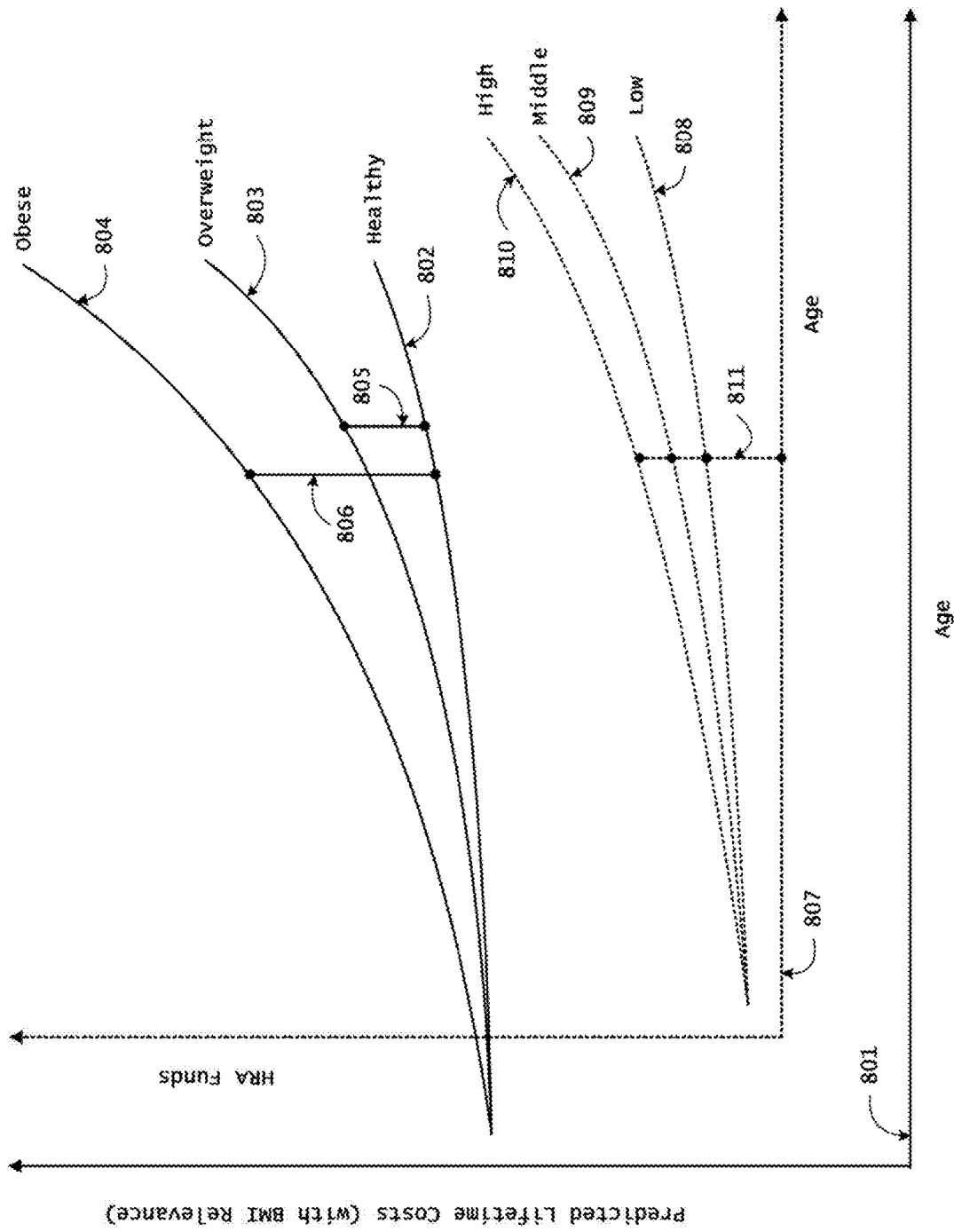

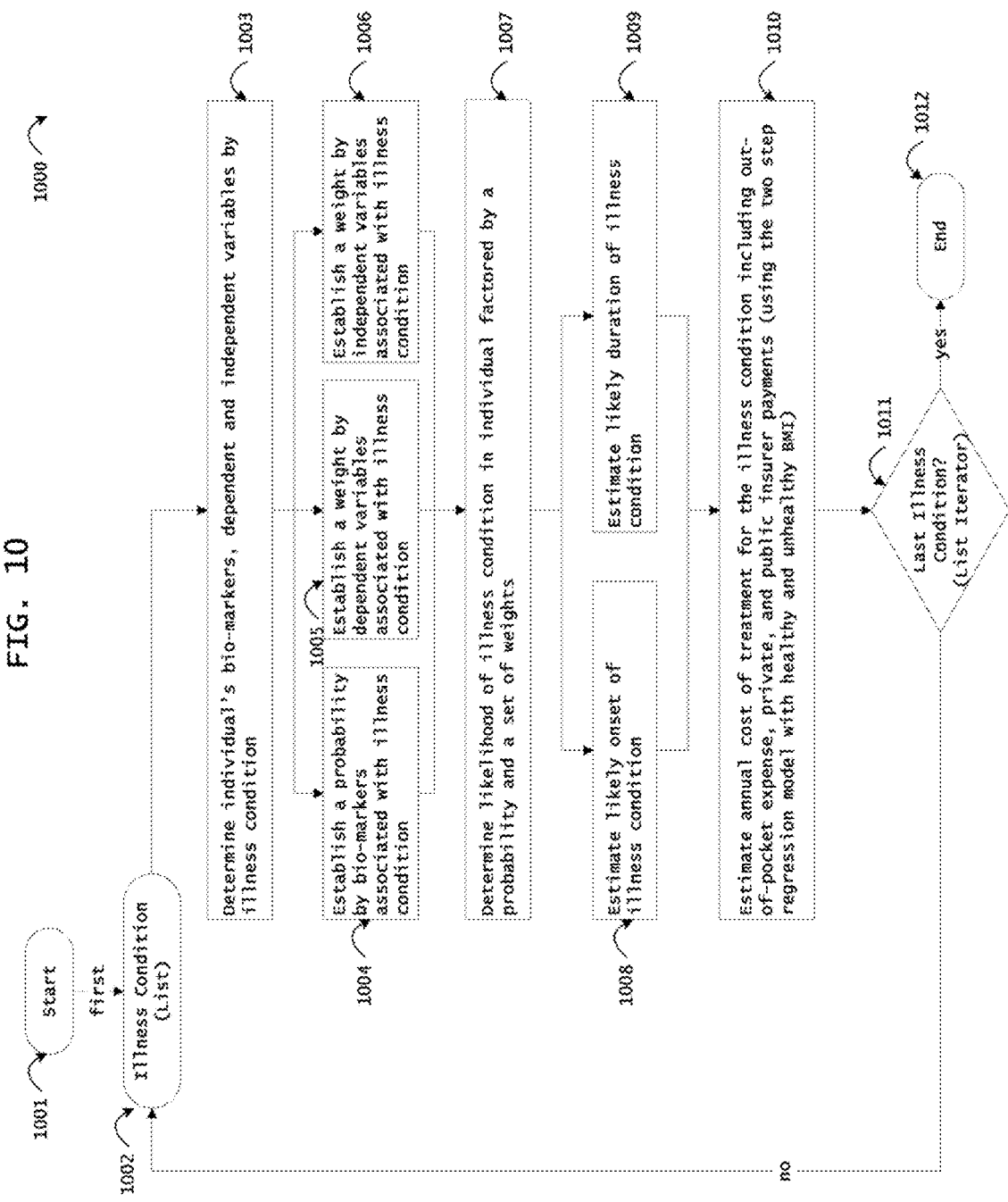

FIG. 17

Data imputing (multiple) from a corpus of population sample sets

```
           smk: linear regression
      chol_rec: linear regression
        mi_rec: linear regression
       chd_rec: linear regression
       ang_rec: linear regression
     wiklim_rec: linear regression
     actlim_rec: linear regression
   wikimagecen: linear regression
   actimagecen: linear regression
    actimagesq: linear regression
    wikimagesq: linear regression
       dbcldar: predictive mean matching
     dbdardarsq: predictive mean matching
     dbcldarsq: predictive mean matching
```
↳ 1702

| Variable | Observations per m | | | |
|---|---|---|---|---|
| | Complete | Incomplete | Imputed | Total |
| hpp_rec | 21928 | 19 | 0 | 21947 |
| ht_dia | 21936 | 11 | 1 | 21947 |
| archie_rec | 21937 | 10 | 0 | 21947 |
| diab_rec | 21941 | 6 | 0 | 21947 |
| strking_rec | 21940 | 7 | 0 | 21947 |
| BMI_kg | 21223 | 724 | 106 | 21947 |
| Educ_rec | 21727 | 220 | 224 | 21947 |
| smk | 20029 | 1918 | 274 | 21947 |
| chol_rec | 21929 | 18 | 0 | 21947 |
| mi_rec | 21939 | 11 | 1 | 21947 |
| chd_rec | 21937 | 10 | 0 | 21947 |
| wiklim_rec | 21930 | 17 | 3 | 21947 |
| actlim_rec | 21943 | 4 | 0 | 21947 |

↳ 1703

Linear regression in first part of model to calculate an expense for an illness

FIG. 19

Logistic regression in second part of model to calculate the probability of an illness Expenditure values (value-1 through value-8) computed by the two-part regression model for a specific age, at healthy and unhealthy BMI, with and without illness condition at the specific current age.

FIG. 22

| Interaction | Class | Type | Value | Example |
|---|---|---|---|---|
| Disease | Categorical | Binary | 0 or 1 | diabetes=0 or diabetes=1 |
| Race | Categorical | Binary | 0 or 1 | asian=1 or asian=0 |
| Gender | Categorical | Binary | 0 or 1 | male=0 or male=1 |
| Age Group | Categorical | Binary | 0 or 1 | age_18_24 == agelast >= 18 & agelast <= 24 |
| BMI Group | Categorical | Binary | 0 or 1 | healthy_weight==bmi_c >= 18.6 & bmi_c <= 24.9 if bmi_c !=, |
| Income (Low) | Categorical | Binary | 0 or 1 | income_low=1 or income_low=0 |
| Income (Medium) | Categorical | Binary | 0 or 1 | income_medium=1 or income_medium=0 |
| Income (High) | Categorical | Binary | 0 or 1 | income_high=0 or income_high=1 |
| Age | Continuous | Discrete | Integer | age=52 |
| BMI | Continuous | Discrete | Float | bmi=24.9 |
| centered-age | Continuous | Discrete | Integer | centered-age=17 |
| centered-bmi | Continuous | Discrete | Float | centered-bmi=20.0 |
| square of centered-age | Continuous | Discrete | Integer | square of centered-age=289 |
| square of centered-bmi | Continuous | Discrete | Float | square of centered-bmi=400.0 |
| Exponent of square of centered-age | Continuous | Equation | Float | exp(centered-age * centered-age) |
| Exponent of square of centered-bmi | Continuous | Equation | Float | exp(centered-bmi * centered-bmi) |
| Exponent of square of illness duration | Continuous | Equation | Float | exp(illness-duration * illness-duration) |
| Exponent of interaction between illness and any two | Continuous | Equation | Float | exp(illness-duration * coefficient of illness) |

FIG. 23

| Description | Variable | Source | Category | Class | Type | Example |
|---|---|---|---|---|---|---|
| Square of Duration of Stroke | strkdursq | Compute | Independent | Continuous | Equation | strk_rec * strkdur |
| Centered BMI | bmicen2 | Compute | Independent | Continuous | Equation | bmi_c - 40 if bmi_c != |
| Interaction between Walking Limitation and Centered BMI | wlkbmicen2 | Compute | Independent | Continuous | Equation | bmicen * wlkin_rec if wlkin_rec != |
| Interaction between Walking Limitation and Centered Age | wlkagecen2 | Compute | Independent | Continuous | Equation | agecen * wlkin_rec if wlkin_rec != |
| Centered Age | agecen | Compute | Independent | Continuous | Equation | age - 40 if age != |
| Smoking | smk | Import | Independent | Categorical | Binary | adsmok42 == 1 if adsmok42 != -9 ¦adsmok42 == -1 ¦adsmok2 != -1 |
| Cholesterol Recoded Variable | chol_rec | Compute | Independent | Categorical | Binary | choldx == 1 if choldx != |
| Myocardial Interaction Recoded Variable | mi_rec | Compute | Independent | Categorical | Binary | midx == 1 if midx != |
| Coronary Heart Disease Recoded Variable | chd_rec | Compute | Independent | Categorical | Binary | chddx == 1 if chddx != |
| Angina Recoded Variable | ang_rec | Compute | Independent | Categorical | Binary | angdx == 1 if angdx != |
| Walking Limitation Recoded Variable | wlkin_rec | Compute | Independent | Categorical | Binary | wlklmtdx == 1 if wlklmtdx != |
| Activity Limitation Recoded Variable | actlim_rec | Compute | Independent | Categorical | Binary | shotdx == 1 if choldx != |
| Interaction of Walking Limitation with Centered Age | wlkimagecen | Compute | Independent | Continuous | Equation | wlklm_rec * agecen |
| Interaction of Activity Limitation with Centered Age | actlimagecen | Compute | Independent | Continuous | Equation | actlim_rec * agecen |
| Interaction of Activity Limitation with Square of Centered Age | actlimagesq | Compute | Independent | Continuous | Equation | actlim_rec * agesq |
| Interaction of Walking Limitation with Square of Centered Age | wlklimagesq | Compute | Independent | Continuous | Equation | wlklm_rec * agesq |
| Duration of Diabetes | diabdur | Import | Independent | Continuous | Discrete | agedur - diabdiagd if diabdiagd >= 0 |
| Interaction of Diabetes with Duration of Diabetes | diabdurdxq | Compute | Independent | Continuous | Equation | diab_rec * diabdur |
| Interaction of Diabetes with Square of Duration of Diabetes | diabdursq | Compute | Independent | Continuous | Equation | diab_rec * diabdursq |
| High Blood Pressure Recoded | hbp_rec | Compute | Independent | Categorical | Binary | hbpdx == 1 if hbpdx != |
| Arthritis Recoded | arth_rec | Compute | Independent | Categorical | Binary | arthdx == 1 if arthdx != |
| Diabetes Recoded | diab_rec | Compute | Independent | Categorical | Binary | diabdx == 1 if diabdx != |
| Stroke Recoded | strk_rec | Compute | Independent | Categorical | Binary | strkdx == 1 if strkdx != |
| Recoded Body Mass Index | cbmi | Compute | Independent | Continuous | Equation | bmicalc53 >= 29 & bmicalc53 != |
| Education (High School) Recoded | Educ_HS | Compute | Independent | Categorical | Binary | hbpdx == 1 if hbpdx != |
| Education (College) Recoded | Educ_Col | Compute | Independent | Categorical | Binary | hbpdx == 1 if hbpdx != |
| Interaction of Arthritis with Centered Age | arthagecen | Compute | Independent | Continuous | Equation | arth_rec * agecen |
| Interaction of Activity Limitation with Square of Centered Body Mass Index | actlimbmicensq2 | Compute | Independent | Continuous | Equation | actlim_rec * bmicensq |
| Interaction of Diabetes with Centered BMI | dbbmicensq2 | Compute | Independent | Continuous | Equation | diab_rec * bmicen |
| Interaction of Diabetes with Square of Centered Body Mass Index | dbbmicensq2 | Compute | Independent | Continuous | Equation | diab_rec * bmicen |
| Interaction of Breast Cancer with Centered Body Mass Index | brstbmicen2 | Compute | Independent | Continuous | Equation | brst_rec * bmicen |
| Interaction of Breast Cancer with Square of Centered Body Mass Index | brstbmicensq2 | Compute | Independent | Continuous | Equation | brst_rec * bmicensq |
| Natural Log (Public) | pl_pub | Compute | Dependent | Continuous | Discrete | nl(pub_exp) if pub_exp != |
| Natural Log (Private) | pl_prv | Compute | Dependent | Continuous | Discrete | nl(prv_exp) if prv_exp != |
| Public_Logistic | d_pub | Compute | Dependent | Categorical | Discrete | pub_exp > 0 |
| Private_Logistic | d_prv | Compute | Dependent | Categorical | Discrete | nl(exp) |
| Natural Log (Out of Pocket) | brstagecen | Compute | Independent | Continuous | Equation | brst_rec * agecen |
| Interaction of Breast Cancer with Centered Age | brstbmicensq | Compute | Independent | Continuous | Equation | brst_rec * bmicen |
| Interaction of Stroke with Centered Body Mass Index | strkbmicen2 | Compute | Independent | Continuous | Equation | strk_rec * bmicen |
| Interaction of Stroke with Square of Centered Body Mass Index | strkbmicensq2 | Compute | Independent | Continuous | Equation | strk_rec * bmicensq |
| Interaction of High Blood Pressure with Centered Body Mass Index | hbptmicen2 | Compute | Independent | Continuous | Equation | hbp_rec * bmicen |
| Interaction of High Blood Pressure with Square of Centered Body Mass Index | hbptmicensq2 | Compute | Independent | Continuous | Equation | hbp_rec * bmicensq |
| Interaction of Osteoarthritis with Centered Body Mass Index | osbmicen2 | Compute | Independent | Continuous | Equation | os_arth * bmicen |
| Interaction of Rheumatoid Arthritis with Centered Body Mass Index | rhbmicen2 | Compute | Independent | Continuous | Equation | rh_arth * bmicen |
| Interaction of Unspecified Arthritis with Centered Body Mass Index | uspbmicen2 | Compute | Independent | Continuous | Equation | unsp_arth * bmicen |
| Interaction of Cholesterol with Centered Body Mass Index | cholbmicen2 | Compute | Independent | Continuous | Equation | chol_rec * bmicen |
| Interaction of Myocardial Infarction with Centered Body Mass Index | mibmicen2 | Compute | Independent | Continuous | Equation | mi_rec * bmicen |
| Interaction of Coronary Heart Disease with Centered Body Mass Index | chdbmicen2 | Compute | Independent | Continuous | Equation | chd_rec * bmicen |
| Interaction of Myocardial Infarction with Square of Centered Body Mass Index | mibmicensq2 | Compute | Independent | Continuous | Equation | mi_rec * bmicensq |
| Interaction of Coronary Heart Disease with Square of Centered Body Mass Index | chdbmicensq2 | Compute | Independent | Continuous | Equation | chd_rec * bmicensq |
| Interaction of Cholesterol with Square of Centered Body Mass Index | cholbmicensq2 | Compute | Independent | Continuous | Equation | chol_rec * bmicensq |

FIG. 24

| Type of Expenditure Category | Private | Public | Out of Pocket |
|---|---|---|---|
| Information Source(s) | MEPS Dataset | Medicare, Medicaid, Veteran's Affairs, Worker's Compensation, Tricare/Champava, and Federal/State/Local/Other Unclassified Sources | MEPS Dataset, Insurer Dataset |
| Description | Variable (Field Name) | Variable (Field Name) | Variable (Field Name) |
| Inpatient hospital stays (facility & doctor) | iptprv, iptopr | iptwcp, iptri, iptofd, iptopu, iptosr, iptmcr, iptmcd, iptva, iptsl | ipsif |
| Total medications | rxprv, rxopr | rxwcp, rxtri, rxofd, rxopu, rxosr, rxmcr, rxmcd, rxva, rxsl | rxsif |
| Home health agency | hhaprv, hhaopr | hhawcp, hhatri, hhaofd, hhaopu, hhaosr, hhamcr, hhamcd, hhava, hhasl | hhasif |
| Home health non-agency | hhnprv, hhnopr | hhnwcp, hhntri, hhnofd, hhnopu, hhnosr, hhnmcr, hhnmcd, hhnva, hhnsl | hhnsif |
| Zero night inpatient stays (doctor) | zdcprv, zidopr | zdwcp, zdtri, zdofd, zdopu, zdosr, zidmcr, zdimcd, zdva, zdsl | zdsif |
| Zero night inpatient stays (facility) | zifprv, zifopr | zifmcr, zifwcd, zifwcp, zifri, zifofd, zifopu, zifosr, zifva, zifsl | zifsif |
| Emergency room (facility & doctor) | ertprv, ertopr | ertmcr, ertmcd, ertwcp, ertri, ertofd, ertopu, ertosr, ertva, ertsl | ertsif |
| All out-patient visits (facility & doctor) | optprv, optopr | optmcr, optmcd, optwcp, optri, optofd, optopu, optosr, optva, optsl | optsif |
| OPD doctor visits (facility) | optprv, optopr | optmcr, optmcd, optwcp, optri, optofd, optopu, optosr, optva, optsl | opvsif |
| OPD doctor visits (doctor) | opsprv, opsopr | opsmcr, opsmcd, opswcp, opstri, opsofd, opsopu, opsosr, opsva, opssl | opssif |
| All office visits | obvprv, obvopr | obvmcr, obvmcd, obvwcp, obvri, obvofd, obvopu, obvosr, obvva, obvsl | obvsif |
| Nurse practitioner ambulatory visit | amnprv, amnopr | amnmcr, amnmcd, amnwcp, amnri, amnofd, amnopu, amnosr, amnva, amnsl | amnsif |
| Office based chiropractor visits | obcprv, obcopr | obcmcr, obcmcd, obcwcp, obctri, obcofd, obcopu, obcosr, obcva, obcsl | obcsif |
| Chiropractic ambulatory visits | amcprv, amcopr | amcmcr, amcmcd, amcwcp, amctri, amcofd, amcopu, amcosr, amcva, amcsl | amcsif |
| Nurse practitioners office visits | obnprv, obnopr | obnmcr, obnmcd, obnwcp, obnri, obnofd, obnopu, obnosr, obnva, obnsl | obnsif |
| Optometrist office visit | obeprv, obeopr | obemcr, obemcd, obewcp, obetri, obeofd, obeopu, obeosr, obeva, obesl | obesif |
| Optometrist ambulatory visits | ameprv, ameopr | amemcr, amemcd, amewcp, ametri, ameofd, ameopu, ameosr, ameva, amesl | amesif |
| Physician assistant ambulatory visits | amaprv, amaopr | amamcr, amamcd, amawcp, amatri, amaofd, amaopu, amaosr, amava, amasl | amasif |
| PT/OT ambulatory visits | amfprv, amfopr | amfmcr, amfmcd, amfwcp, amftri, amfofd, amfopu, amfosr, amfva, amfsl | amfsif |
| All dental care | dvtprv, dvtopr | dvtmcr, dvtmcd, dvtwcp, dvtri, dvtofd, dvtopu, dvtosr, dvtva, dvtsl | dvtsif |
| Other equipment & supplies | othprv, othopr | othmcr, othmcd, othwcp, othtri, othofd, othopu, othosr, othva, othsl | othsif |

SYSTEM AND METHOD FOR EVIDENCE BASED DIFFERENTIAL ANALYSIS AND INCENTIVES BASED HEALTHCARE POLICY

CROSS-REFERENCE TO RELATED APPLICATIONS

This patent specification is a continuation-in-part of application Ser. No. 13/328,011 filed on Dec. 16, 2011 in the United States Patent and Trademark Office, the entire contents of which are incorporated by reference herein.

BACKGROUND OF THE DISCLOSURE

Field of the Disclosure

This invention relates to the field of health insurance and, more particularly, to a system and method to estimate reduction in lifetime out-of-pocket expenses to the insured and direct cost to the insurer with an incentive-based plan to achieve a healthy body mass index (BMI) and evidence based predictive and differential analysis of relevant compound risks and incremental lifetime expenditures.

Description of the Related Art

The rising cost of insurance premiums and out-of-pocket expenses for healthcare, and an increasing population at risk with inadequate or no health insurance across all age groups, is becoming a cause of concern to governments and private healthcare industry at large. The projected cost of coverage to insurance companies based on trends in lifestyles and emerging patterns of diseases is alarming and is a serious challenge to the industry.

The Patient Protection and Affordable Care Act (PPACA) is a United States federal statute signed into law in 2010. PPACA requires health insurance companies in the United States to increase insurance coverage of pre-existing conditions, and spend 80 to 85 percent of premium dollars on medical care and health care quality improvement, rather than on administrative costs, starting in 2011. Insurance companies that do not meet the medical loss ratio standard provision will be required to provide rebates to their consumers, payable by August $1^{st}$ each year, starting in 2012. Enrollees, to whom rebates are owed, will receive a premium reduction rebate check or lump-sum reimbursement to a credit or debit card account. Pursuant to National Association of Insurance Commissioners (NAIC) recommendations, the regulation specifies quality improvement activities grounded in evidence-based practices, for innovations counted toward the 80 or 85 percent standard.

Families plan for future expenses towards the purchase a home, to pay for their children's college education, vacations, and other discretionary expenses. However, most families do not plan for their out-of-pocket healthcare costs—post-employment and in retirement. This innovation provides a method and system for families and financial advisors to plan for lifetime out-of-pocket costs of healthcare, while enabling healthcare insurers to participate in the process by offering financial incentives to motivate their beneficiaries and reduce the total cost of healthcare by lowering risks associated with early onset of illness and the duration of illness.

SUMMARY OF THE DISCLOSURE

Certain exemplary embodiments of the present disclosure provide an apparatus and/or system to predict relevant future lifetime out-of-pocket, facility and treatment expenses based on a plurality of dependent and independent variables, weighted by body mass index (BMI) influencers, including prior to the occurrence of any illness condition and post-treatment of an illness condition.

According to an exemplary embodiment, the present disclosure provides a method, apparatus, and/or system for a plurality of services that enable quality improvement activities grounded in evidence based practices and affordability of preventive and curative medical treatment based on a plurality of factors.

Certain exemplary embodiments may include a method, apparatus and/or system to establish medical insurance premiums and deductibles based on, or adjusted for, BMI.

Certain exemplary embodiments may include a method, apparatus and/or system for proactive measures to increase the likelihood of desired health outcomes based on BMI.

Certain exemplary embodiments may include a method, apparatus and/or system to estimate incremental lifetime healthcare expenditures among overweight and obese individuals with specific illnesses.

Certain exemplary embodiments may include a method, apparatus and/or system for a computer based program (e.g., web or non-web application or service) to process and analyze digital datasets (or electronic healthcare datasets), such as for example, electronic insurance records, electronic medical records (EMR), electronic health records (EHR), personal health records (PHR), etc. The system may include regression theory, differential analysis, statistical analysis and modeling using a plurality of data sources and filters to generate multiple reports and perspective data views. The report may represent risk analysis, mitigated risks, predictive forecasts of costs, and predictive forecasts of savings based on mitigated risks.

The computer based program may be configured to include (e.g., embedded or over secure communications channels) datasets of disease onset trends, patient profiles, and treatment patterns from structured and semi-structured datasets from multiple data providers.

Certain embodiments may be embodied as a method, apparatus and/or system that may include a professional (enterprise) service to healthcare providers as a web or non-web based subscription.

Certain embodiments may also be embodied as a method, apparatus and/or system that may include a personalized service to healthcare recipients as a web or non-web based subscription.

Certain exemplary embodiments may include a method, apparatus and/or system to create a Healthcare Individual Reimbursement Account (HIRA) for members (healthcare recipients, families, etc.) wherein an annual rebate (for example, a refund calculated as a percentage of paid premiums) is offered as a reimbursement on achieving a healthy BMI for the year.

Certain exemplary embodiments may include the use of the HIRA funds for: (1) deductibles; (2) out-of-pocket expenses; (3) health club membership fees; (4) weight loss programs; and/or (5) other activities to promote desired health outcomes for recipients.

Certain exemplary embodiments may include a method, apparatus and/or system to influence the food industry including, for example, one-off production, batch production, mass production and just-in-time production, to adopt desired consumer health outcome conscious approaches, based on BMI influencers.

According to an exemplary embodiment, the present disclosure provides a method for determining lifetime healthcare expenditures for an individual, on-demand and in real-time, based on body mass index on a computing system having a data harvester, a data aggregator, aggregate health profiles, a two-part regression model, and a final part regression model. The method includes: receiving a request for an estimate of the lifetime healthcare expenditures for an individual of interest; and querying, by the data aggregator, in real-time, the most recent healthcare datasets for a plurality of individuals, including the individual of interest, from the data harvester. The method also includes retrieving, by the data harvester, in real-time, using a plurality of data source specific connectors, the most recent healthcare datasets from a plurality of healthcare data providers, wherein each healthcare dataset includes at least the body mass index, the age, and the personal health record associated with an individual, and wherein the plurality of individuals includes a first subset of individuals associated with an illness condition and a second subset of individuals not associated with the illness condition; and receiving, by the data aggregator, the plurality of the most recent healthcare datasets for the plurality of individuals. The method also includes generating, by the data aggregator, processed healthcare datasets by mining data from a plurality of data exchange formats in the plurality of the most recent healthcare datasets, recoding data in the plurality of the most recent healthcare datasets for normalization and consideration of missing values in categories of data, and imputing data in order to account for missing values in the plurality of the most recent healthcare datasets; generating, by the data aggregator, aggregate health profiles for the plurality of individuals from the processed healthcare datasets, wherein the aggregate health profile includes attributes from at least the medical health records, personal profile, medical history, and claims history of the individual; and receiving, by a two-part regression model of the computing system, the aggregate health profiles, a first set of variables related to characteristics of the individual of interest, and interactions that are expressed as a second set of variables and represent a quantitative contextual and evidence based correlation between illnesses, treatments, the onset and duration of illness, and attributes in the individual's aggregate health profile. The method further includes generating, by the two-part regression model of the computing system, indicators for an illness, wherein the indicators include expenses for the illness, probability of the illness, and coefficients for the illness; receiving, by a final part regression model of the computing system, the indicators for the illness, the interactions, and the first set of variables; and estimating, by the final part regression model of the computing system, the total lifetime healthcare expenditures for the individual of interest and a healthcare risk score for the individual of interest based on the indicators for the illness, the interactions, and the first set of variables.

These and other features of the present disclosure will be readily appreciated by one of ordinary skill in the art from the following detailed description of various implementations when taken in connection with the accompanying drawings.

BRIEF DESCRIPTION OF THE DRAWING FIGURES

The disclosure is best understood from the following detailed description when read in connection with the accompanying drawings. According to common practice, various features/elements of the drawings may not be drawn to scale. Common numerical references represent like features/elements. The following figures are included in the drawings:

FIG. 3 is a schematic diagram illustrating method of modeling cost flows for affordable and sustainable healthcare services in accordance with various exemplary embodiments of the disclosed system;

FIG. 4 is a flowchart illustrating a method for providing a first part of a model for statistical analysis to compute healthcare expenditures in accordance with various exemplary embodiments of the disclosed system;

FIG. 5 is a flowchart illustrating a method for providing a second part of the model for statistical analysis to compute healthcare expenditures in accordance with various exemplary embodiments of the disclosed system;

FIG. 6 is a flowchart illustrating a method for providing statistical analysis, based on the first and second parts of the model illustrated in FIGS. 4 and 5, to compute healthcare expenditures in accordance with various exemplary embodiments of the disclosed system;

FIG. 7 is a flowchart illustrating a method for providing statistical analysis to compute healthcare cost reductions, prevalence of individuals with inadequate activities in daily living and functional limitations, and total expenditures for the population with the illness in accordance with various exemplary embodiments of the disclosed system;

FIG. 8 is a graphical representation illustrating a method for providing differential analysis of predicted lifetime costs and predicted cost reductions in accordance with various exemplary embodiments of the disclosed system;

Figure 11:
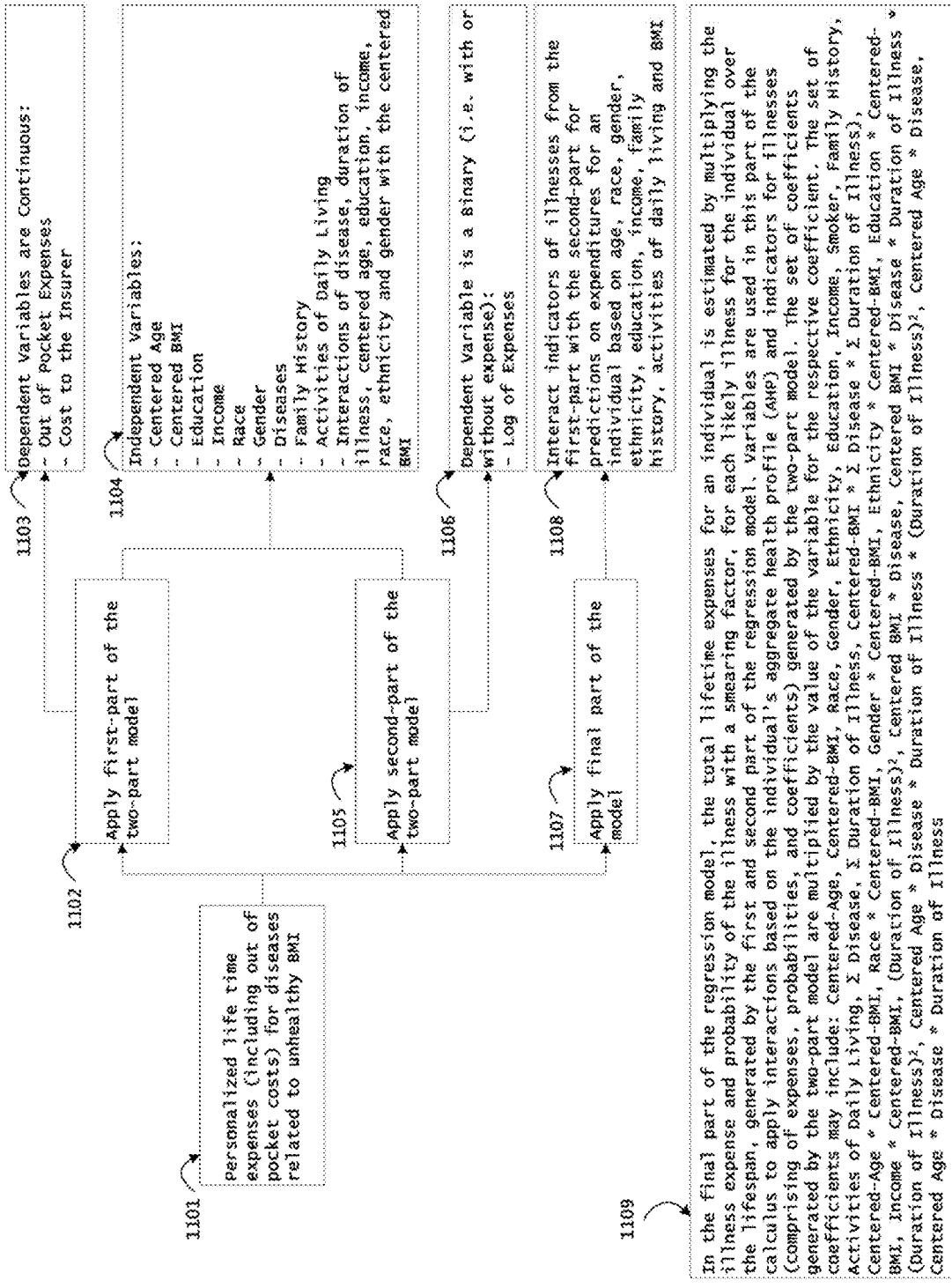

FIG. 10 is a graphical representation illustrating an algorithm for providing differential analysis of predicted lifetime costs and predicted cost reductions in accordance with various exemplary embodiments of the disclosed system; and FIG. 11 is a graphical representation illustrating a multipart model for providing personalized and interactions based granular differential analysis of predicted lifetime costs and predicted cost reductions in accordance with various exemplary embodiments of the disclosed system.

Figure 12:
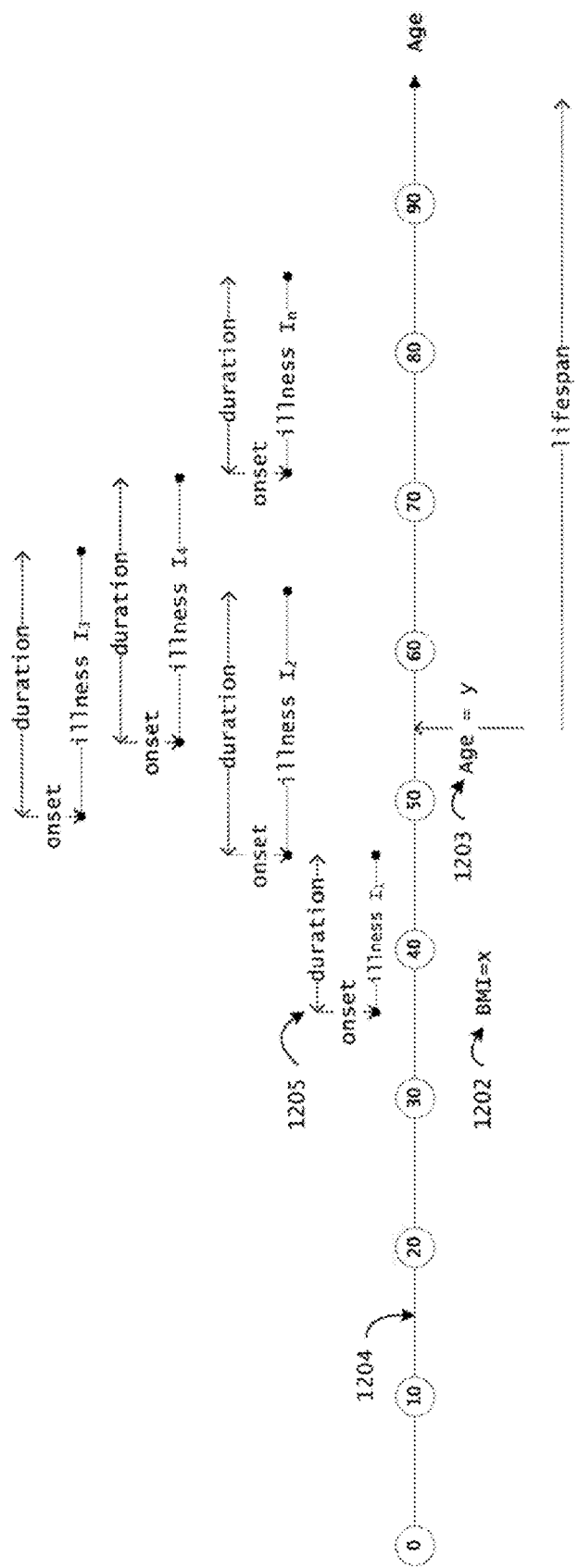

FIG. 12 is a graphical representation of a method to calculate in age and/or BMI centered increments the lifetime expenditures for an individual, iteratively over a plurality of illness related expenditures by onset and duration of illness, in accordance with various exemplary embodiments of the disclosed system.

Figure 13:
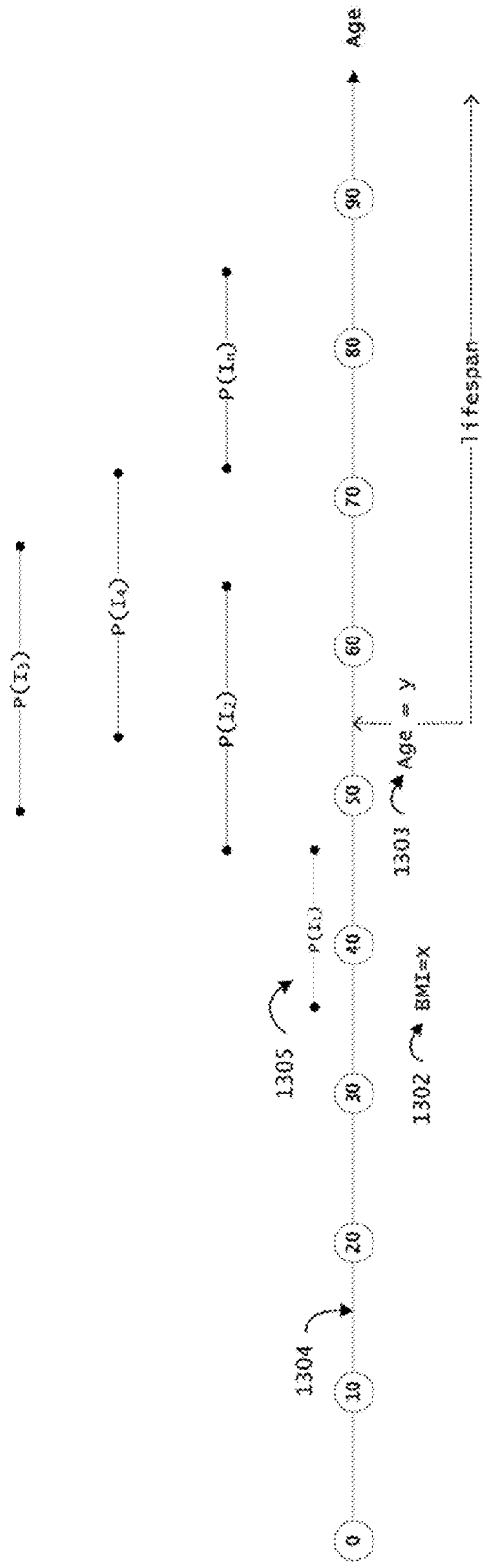

FIG. 13 is a graphical representation of a method to calculate in age and/or BMI centered increments the probability of an illness related expenditure for an individual, iteratively over a plurality of illnesses, in accordance with various exemplary embodiments of the disclosed system.

Figure 14:
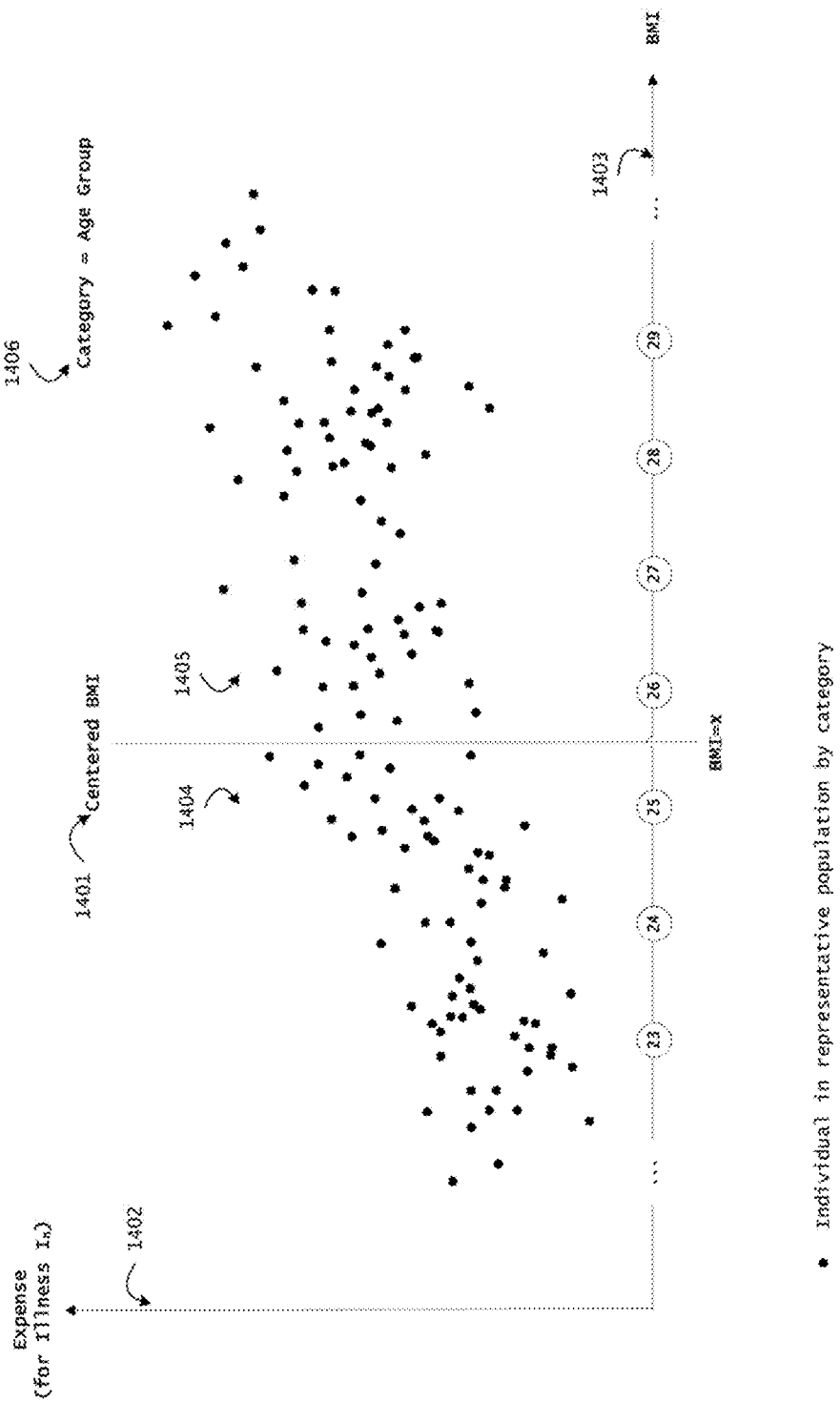

FIG. 14 is a graphical representation of a method to center by BMI within a population cluster categorized by age group, in accordance with various exemplary embodiments of the disclosed system.

Figure 15:
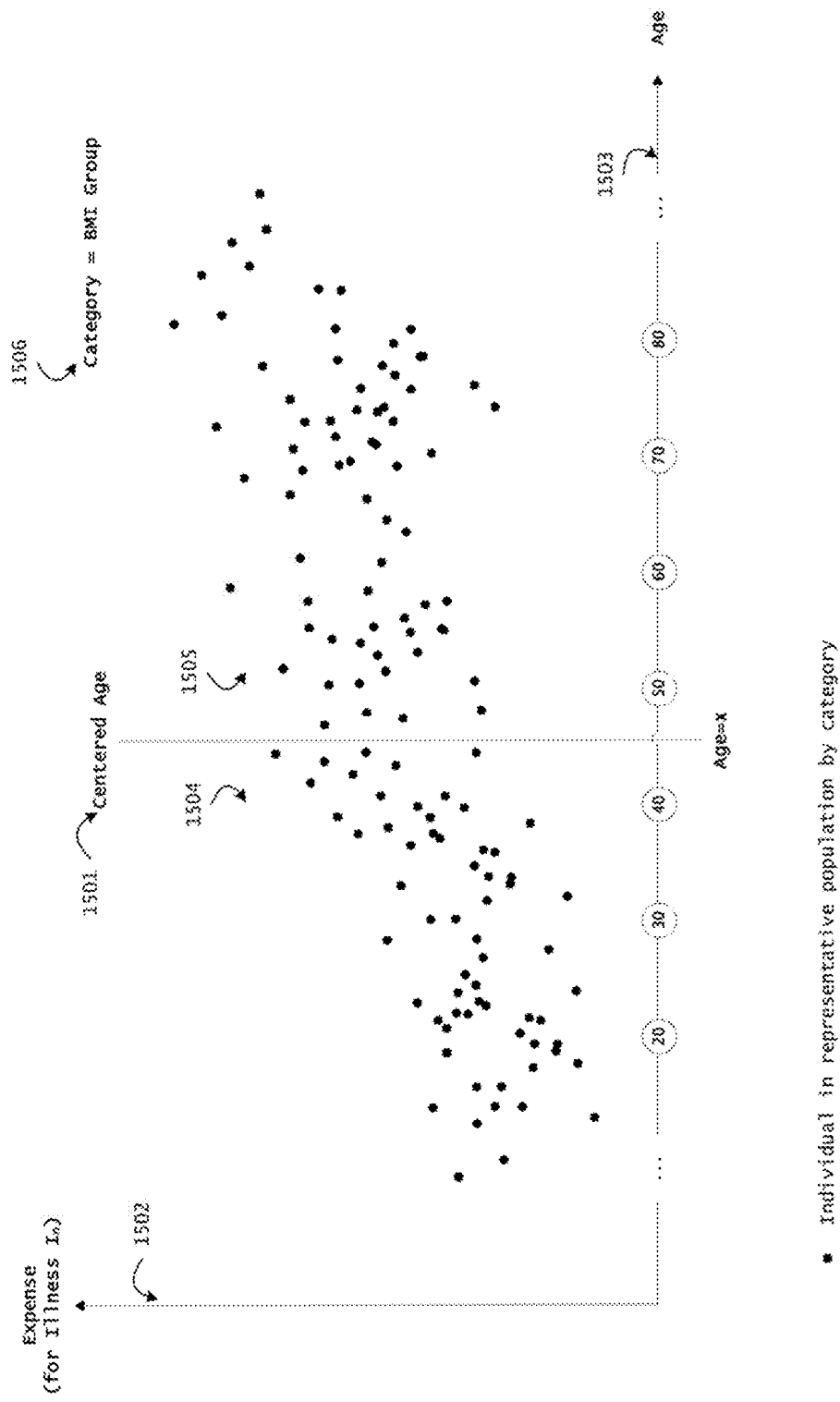

FIG. 15 is a graphical representation of a method to center by age within a population cluster categorized by BMI group, in accordance with various exemplary embodiments of the disclosed system.

Figure 16:
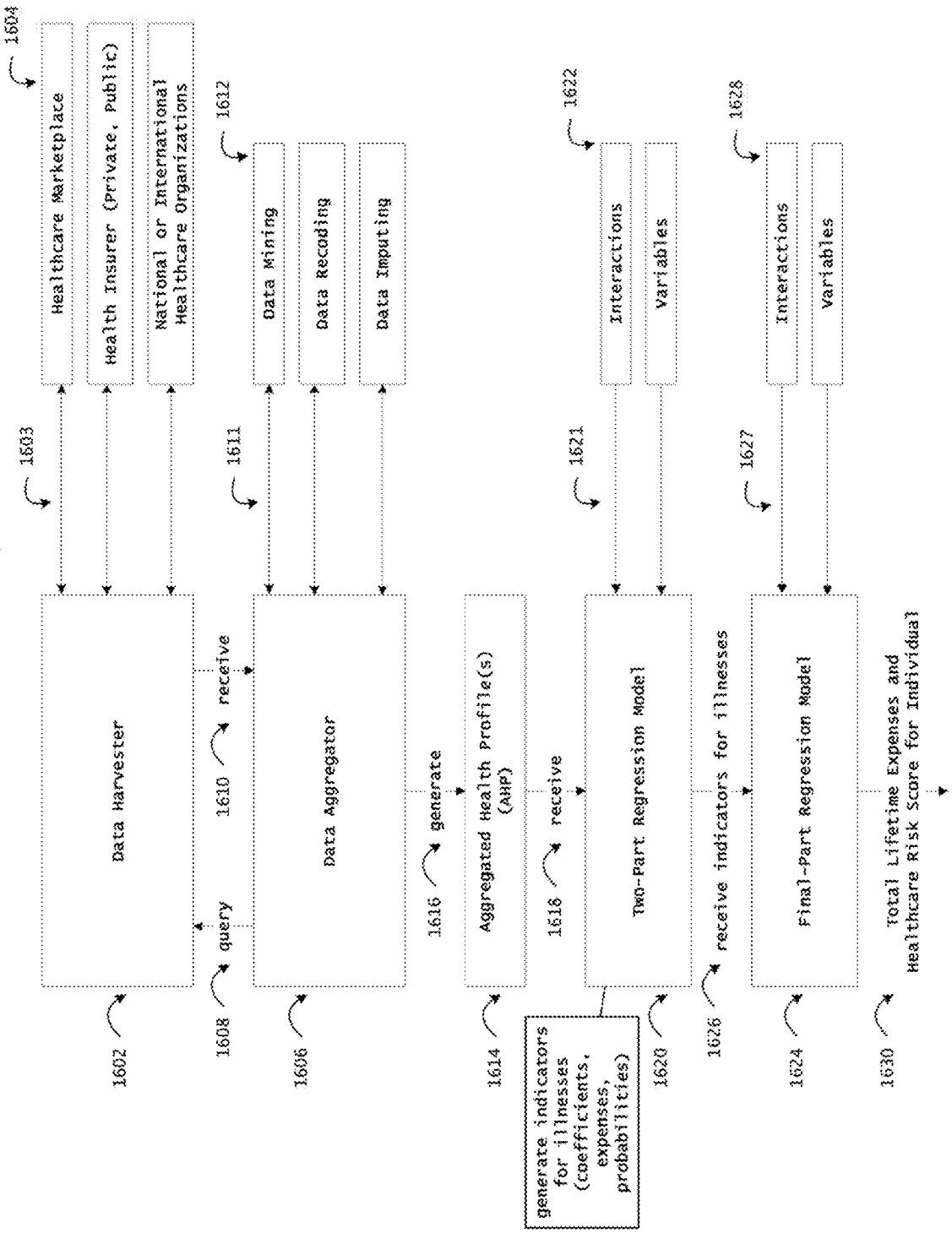

FIG. 16 is a flowchart illustrating a method for data aggregation based on mining, recoding, and imputing of received healthcare datasets, to generate aggregate health profiles for a population of individuals, for interactions based regression analysis and estimation of lifetime expenditures for an individual, in accordance with various exemplary embodiments of the disclosed system.

FIG. 17 is a graphical representation of a method to impute data from a corpus of population sample sets, in accordance with various exemplary embodiments of the disclosed system.

Figure 18:
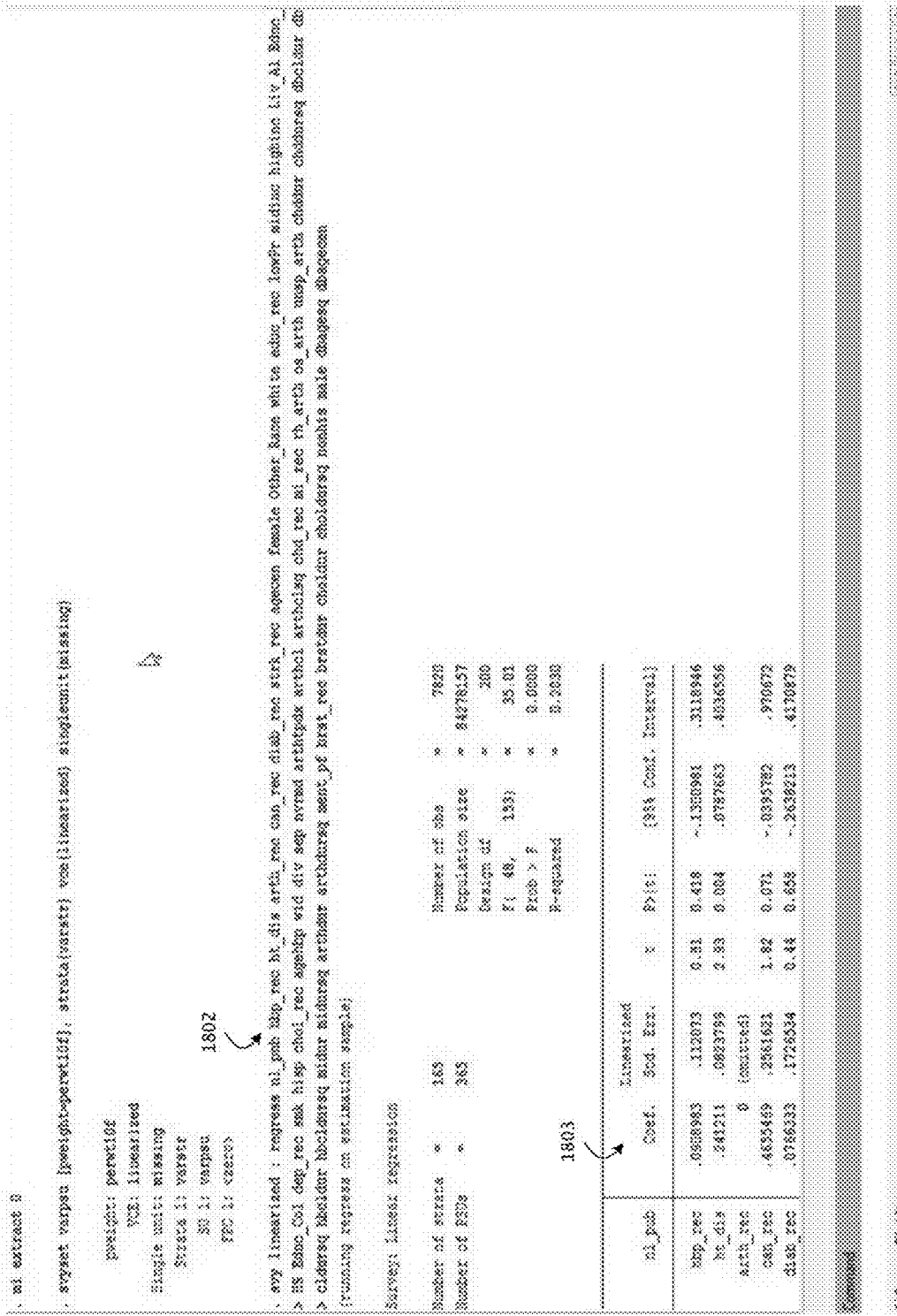

FIG. 18 is a graphical representation of a method to perform linear regression in the first part of the two-part model for calculation of an expense for an illness, in accordance with various exemplary embodiments of the disclosed system.

FIG. 19 is a graphical representation of a method to perform logistic regression in the second part of the two-part model for calculation of the probability of an illness for an individual, in accordance with various exemplary embodiments of the disclosed system.

Figure 20:
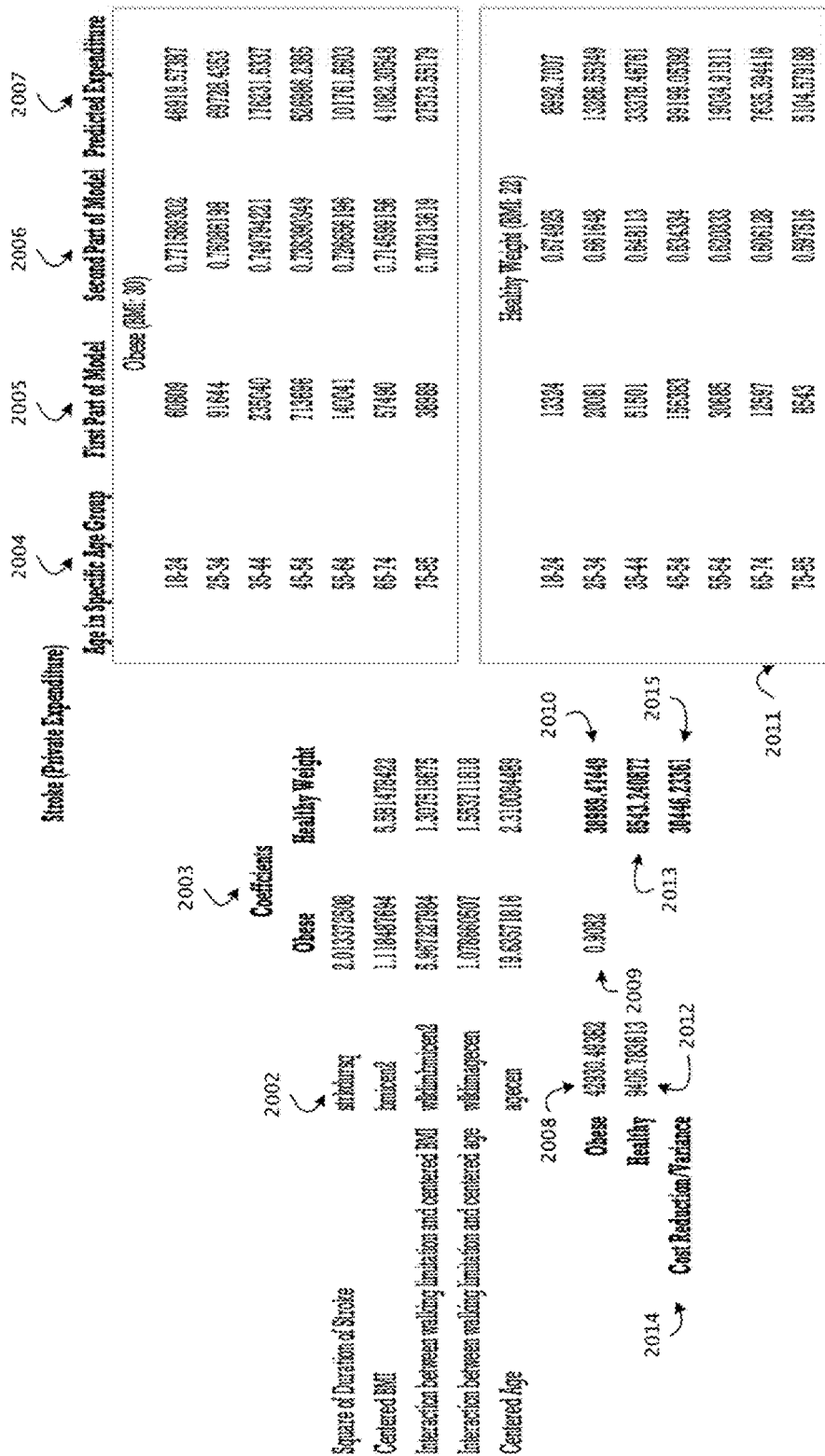

FIG. 20 is a graphical representation of a method to predict future expenditures for an illness, calculated by the regression model based on dependent and independent variables for the illness and an individual, in accordance with various exemplary embodiments of the disclosed system.

Figure 21:
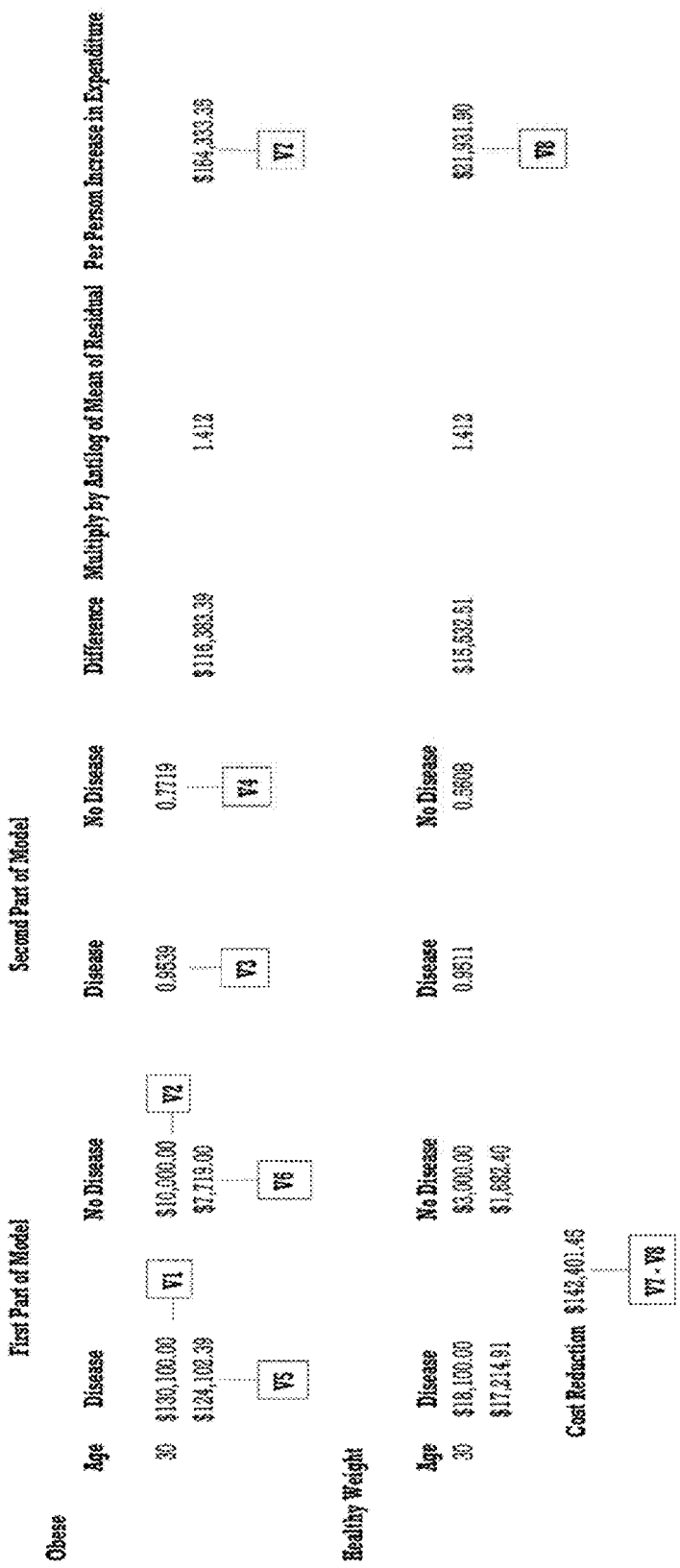

FIG. 21 is a graphical representation of a method that estimates likely future disease related expenditures for an individual, with and without the disease condition at the current age, in accordance with various exemplary embodiments of the disclosed system.

FIG. 22 is a table illustrating examples of interactions in the regression model by class, type and value, in accordance with various exemplary embodiments of the disclosed system.

FIG. 23 is a table illustrating examples of variables in the regression model by description, source, category, class, and type, in accordance with various exemplary embodiments of the disclosed system.

FIG. 24 is a table illustrating examples of variables in the regression model imported from datasets by source, description, and variable (field or tag), in accordance with various exemplary embodiments of the disclosed system.

Figure 25:
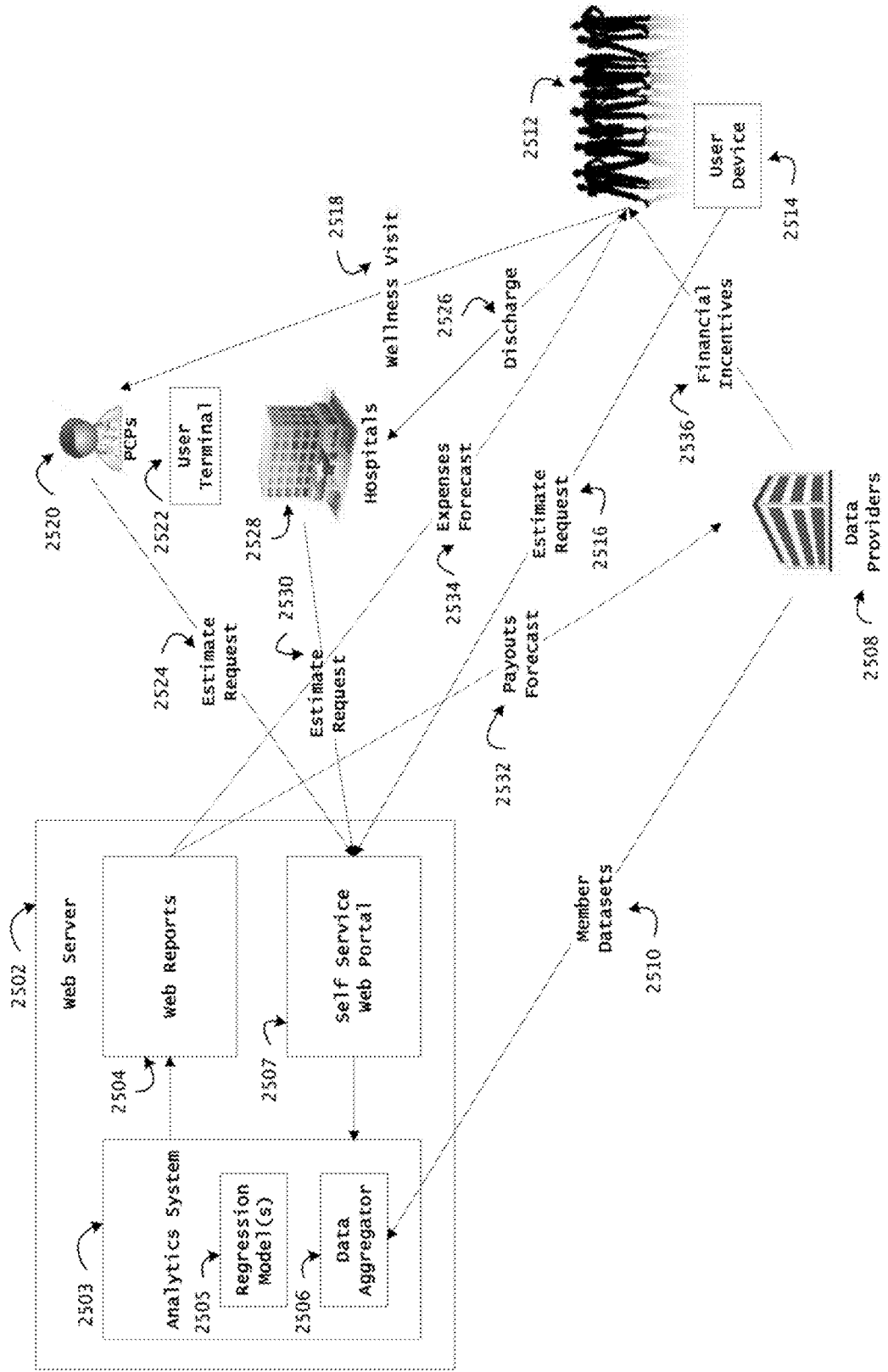

FIG. 25 is a workflow illustrating transactions between users and the on-demand real-time analytics service, in accordance with various exemplary embodiments of the disclosed system.

Figure 26:
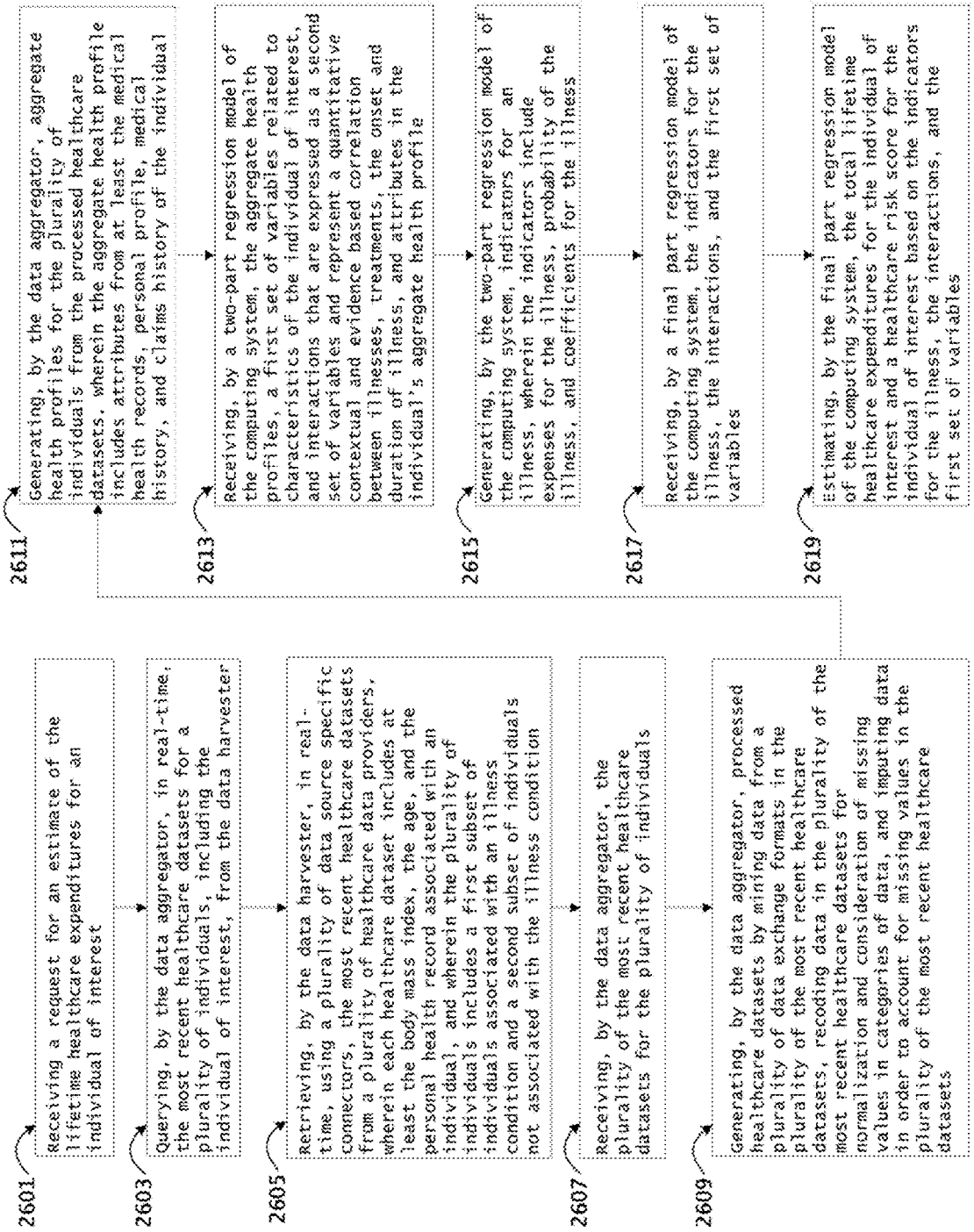

FIG. 26 is a flowchart illustrating a method for determining lifetime healthcare expenditures for an individual in accordance with various exemplary embodiments of the disclosed system.

Further areas of applicability of the present disclosure will become apparent from the detailed description provided hereinafter. It should be understood that the detailed description of exemplary embodiments are intended for illustration purposes only and are, therefore, not intended to necessarily limit the scope of the disclosure.

DETAILED DESCRIPTION

Although the disclosure is illustrated and described herein with reference to specific embodiments, the invention is not intended to be limited to the details shown herein. Rather, various modifications may be made in the details within the scope and range of equivalents of the claims and without departing from the scope of the disclosure.

National representative estimates of expenditures for the United States population for diseases common to overweight and obese individuals by years since time of diagnosis may be estimated using one among a plurality of regression analysis techniques.

Context Driven Predictive Analytics

The fundamental principle of the embodiments is based on the notion that there is no truth in data, just statistical probabilities. Therefore, data silos require relevant context for accuracy of analysis. Merely applying mathematical functions on one dataset to generate statistical metrics without context produces little value. Further, the predictive model must leverage the context with appropriate level of inductive, deductive and abductive reasoning, which may be expressed in forms that are consumable in a data and computation model. Weather predictions are accurate only in the immediate short term because of the dynamic and non-linear nature of the underlying data which the model relies on. Stock futures are accurate for a few quarters because of market volatility and uncertainties in long-term geo-political events, economic policies and flux in supply and demand. Predicting the outcome of a major league baseball game is based on the most recent information about the players batting, base running, fielding and pitching statistics. In medical health, the irreversible aging process, social history, family history, vital signs, activities of daily living, and personal habits are significant influencers of future outcomes. Further, the correlation between illnesses, the immune system, bio-markers and DNA of an individual are based on scientific evidence and case histories. Therefore, the orchestration of medical datasets to identify interactions, and apply similarity functions using grammar rules to analyze an individual's dataset in context is key to improving the accuracy of estimation of likely future outcomes. Unlike other approaches that use likelihood functions for a probability-based analytics, the present embodiments are context centric for a similarity-based analytics. The context, and not data silos, is the key variant in the proposed analytics model. The data is processed to derive context (through data orchestration), and then the context is applied to analyze the data (through a regression model).

A likelihood function determines an unconditional probability based on longitudinal data analysis that may produce an inaccurate estimate. For example, if 9 out of 100 individuals in a sample set categorized by BMI group (e.g. BMI range 35-45) have diabetes by the age of 50, a likelihood function produces a probability that an individual matching the profile is likely to have diabetes by age 50. In contrast, a similarity function is a conditional probability based on linearization of longitudinal data for a better (goodness of) fit in the model of the sample set, using interactions and variables personalized for an individual to produce a more accurate probability that an individual matching the profile is likely to have diabetes by age 50.

Modified RAND Two-Part Model

Published RAND studies on alternate models describe the merits and estimation precision of the one-part, two-part and four-part models. The two-part model is adjusted for the large number (20%) of zero expenses and uses a likelihood function to estimate probabilities. The four-part model adjusted for the positive expense skew (80%) with ambulatory and inpatient (hospital) utilization. Other approaches that adopted the RAND two-part estimation methods provided averages in lifetime expenditures.

The proposed model modifies the two-part model to address estimation problems posed by the distribution (or scatter) of medical expenses by pivoting on centered BMI and/or age, and categorization of datasets, to generate coefficients and consider interactions in the calculus of an expense and probability of an expense by illness. The model includes interactions of all diseases with age and BMI predictors as opposed to comorbidities only. Interpretation of the output is the predicted expense of the individual at the centered BMI and/or at the centered age. The contextual bias on the data thereby produces more reliable estimates within categorical subsets, and produces benefits for policy decisions on budgets and premiums.

The Regression Model

In an exemplary embodiment, the regression model is based on a modified two-part RAND model and a final part model, that interacts the first and second part of the two-part model and multiplies the result obtained with a statistical smearing factor (or bias correction factor). The de-identified (anonymized) information from a plurality of queried data sources are pruned by mining, recoding and imputing the received data in real time to generate attributes for an Aggregate Health Profile (AHP) for each individual in the received representative population sample. The lifespan (i.e. life expectancy of an individual) in the regression model may be set to the maximum age for which an AHP is available. The AHP attributes about an individual (i.e. a healthcare beneficiary) include medical health records and the personal profile of the individual (including, for example, at least one of age, height, weight, BMI, occupation, family history, illnesses, medications, allergies, gender, income, education, race, daily activities of living, activity limitations, smoker, bio-markers, immunizations, vital signs, social history (smoking, alcoholism, tobacco use, nicotine use, etc.), health conditions designated by ICD/HCPCS/CPT codes and onset dates, genetic disposition, medical history, claims history, etc. For privacy protection, appropriate information in the AHP may be anonymized by tokenization. The AHP attributes, a set of interactions, and a set of variables are then processed by the first and second part of the model to generate coefficients through linear and/or logistic regression analysis methods. The variables in the first and second part of the two-part model may be predominantly, but not limited to, binary or discrete values. The coefficients generated by the two-part model are then received by the final part of the model and processed using interactions (FIG. 22) and variables (FIGS. 23-24) to calculate the total lifetime expenses for an individual of interest by age and BMI. The received coefficients are multiplied by the value of the variables determined based on the AHP of the individual of interest. The variables in the final part may be binary or discrete values, or equations based on the received coefficients. The calculations of expenditures and probabilities in the regression model may be implemented using various techniques such as pivoting by age (centered age), and/or pivoting by BMI (centered BMI), and/or clustering by age groups, and/or clustering by BMI groups. The dependent variables may be transformed to a natural log. In certain exemplary embodiments, other techniques may also be applied. Further details of regression equations can be found at faculty.cas.usf.edu/mbrannick/regression/Reg2IV.html, and is incorporated by reference herein in its entirety.

Data Orchestration

In an exemplary embodiment, the method performs on-demand and in real-time healthcare data aggregation that includes directed queries to a data harvester 1602, data source specific connectors 1603 to data providers 1604 (e.g., healthcare marketplace, health insurer (private or public), national or international healthcare organizations), parsers for data mining, and grammar rules for data recoding and data imputing. The method transforms a disparate corpus of healthcare datasets into aggregate health profiles for processing by a multi-part regression model. In an exemplary embodiment, the model is programmed with variants, based on interactions and pivots (e.g. age, body mass index—BMI), to generate (a) the categorical expenditures (private, public and out-of-pocket payments) by illness; (b) the probability that an individual may incur that expenditure in the future; and (c) coefficients for the estimation of lifetime healthcare expenditures and a healthcare risk score of an individual.

The volume and variety of fragmented and distributed digital healthcare datasets, including electronic insurance records, electronic medical records (EMR), electronic health records (EHR), personal health records (PHR), in the hundreds of millions, in structured and semi-structured data formats (schemas), and diverse set of data exchange protocols require a highly scalable computing architecture and fabric for "big data" orchestration. Further, data harvesting and aggregation requires a high performance architecture and scalable engines to process voluminous data for mining, recoding and imputing that are critical to prepare the digital datasets for contextual analytics by a regression model. The task of consolidating a plurality of disparate healthcare data records, correlating the associated data fields, applying interactions across medical conditions and illnesses, and personalization of variants for an individual in a cohort based on an intricate decision logic and grammar, is impossible to accomplish humanly as a mental calculus without an automated data processing system with memory, compute, storage, and network resources.

Data Harvester

The data harvester 1602 provides data source specific connectors 1603 to harvest, on-demand and in real-time, the most recent information from a plurality of data providers 1604, the data harvester 1602 can perform the steps of:

a) Receiving de-identified (or anonymized) patient population datasets in real-time from a plurality of healthcare data providers 1604 (e.g. health insurance companies, healthcare marketplace, healthcare service providers, national and international healthcare organizations) over secure and encrypted transport protocols and APIs (e.g. Representational State Transfer (REST), Simple Object Access Protocol (SOAP), etc.).

b) Receiving healthcare datasets for identified individual(s) by qualifying criteria (e.g., age, BMI, illness, gender, race, occupation, education, allergies, family history, social history, income, geo-location, claims history, etc.) from healthcare data providers 1604.

c) Receiving health related statistical, scientific and population data from healthcare organizations (e.g. CDC Centers for Disease Control and Prevention, WHO World Health Organization) pertaining to illnesses, expenditures, and surveys.

The on-demand service may be provided through a web portal, software-as-a-service (SaaS) or cloud hosted application to the user of the service, such as for example healthcare beneficiaries, healthcare service providers, and healthcare insurers. The information is retrieved in real-time, through directed queries to data providers, i.e. the authoritative data sources. The information is stored in the memory 150 of a computer system 100 only for the duration of the data processing, without data retention on an intermediate volatile on non-volatile storage media.

Data Aggregation

In an exemplary embodiment, data aggregation includes the steps of data mining, data recoding and data imputing. Data mining extracts information from structured and semi structured data formats (e.g. Comma Separated Values (CSV), Tab Separated Values (TSV), Excel, JavaScript Object Notation or JSON, Extensible Markup Language or XML). Data recoding can be performed for normalization and generation of missing values in the received datasets. Data imputing can be performed to generate missing values in the received datasets.

Data Recoding

In an exemplary embodiment, data recoding may be performed to generate categorical or continuous variables, and to code missing values into different categories. For categorical variables, recoding can be performed to normalize enumerated or coded values received in the dataset to a binary value (0 or 1). For example, male=1, female=2 in received datasets is recoded to assign a 0 or 1 to a gender variable. Similarly, recoding may be applied to indicate variables such as race, ethnicity, income, education, etc. For continuous variables, recoding can be performed to normalize missing values in a dataset by mapping values in the received dataset to a contiguous range.

Data Imputing

In an exemplary embodiment, data imputing is performed to generate values for the missing variables in the population data received from multiple data providers. The various methods that may be used include linear regression, logistic regression for a binary variable, predictive mean matching for a continuous variable, and sequential matching using monotone missing pattern. A missing variable may also be imputed using other non-missing variables determined from the AHP of the individual.

Coefficients

For a dependent variable y with a single independent variable x, the linear part with a slope (m), intercept (b) and error (e) may be expressed as an equation y=mx+b+e. This may be further extended to multiple independent variables as $y=m_1x_1+m_2x_2+\ldots+m_nx_n+b+e$. R-square, the correlation coefficient or proportion of variance due to regression, is the ratio of variability in the modeled values to the variability in the original data set. It represents the fluctuation in the dependent variable that is accounted for by the independent variables within the regression model. Higher the R-square, better would be the accountability provided by the variables in the regression model. In a simple regression with a single independent variable, it may be calculated as: $R^2$=(variance of actual value)/(variance of predicted value+variance of error). In multiple regression with uncorrelated independent variables, it may be calculated as a sum of the squared correlations of the independent variables with the dependent variable, as $R^2=r^2_{y1}+\ldots+r^2_{yn}$. In multiple regressions with correlated independent variables, it may be calculated as a weighted sum of the correlation of each independent variable, where the beta weight is the respective standardized slope, as $R^2=B_1r_{y1}+\ldots+B_2r_{yn}$. Other general formulas may also be used to calculate R-square. The beta coefficient of the intercept b may be used in the calculation of expenditures when non-standardized beta coefficients are considered for the analysis.

Referring to FIGS. 18-20, in an exemplary embodiment, non-standard coefficients are output from the regression model. Standard (or beta) coefficients may be derived by subtracting the non-standard coefficient from the mean and then dividing by the linearized standard error. The method of linearization transforms the dataset by applying the variables generated (created) to produce a dataset that represents a better fit in the model. The standard errors calculation may be performed as follows:

1) Calculate the mean of the sample sets.
2) Subtract the mean from each value in the sample set.
3) Square the deviation.
4) Summate the deviation.
5) Calculate the standard deviation by dividing the value obtained in (4) by n−1, where n is the sample size.
6) Calculate the standard error by dividing value in (5) by the square root of n.

Categorization

In an exemplary embodiment, data clustering for categorization may be performed by age group (e.g. infants, children, teenagers, adults, seniors, generation X, generation Y), or BMI group (e.g. healthy, unhealthy, normal (18.5-25), very severely underweight (15), severely underweight (15-16), underweight (16-18.5), overweight (25-30), moderately obese (30-35), severely obese (35-40), very severely obese (40)). Regression analysis (linear, logistic) within a category may be centered by age and/or BMI to estimate expenditures and/or probabilities in the two-part model.

Dummy Variables

A dummy variable is a binary constant (i.e. the value is either 0 or 1).

Centered BMI

Referring to FIG. 14, centering by BMI establishes a pivot point within a subset of data (e.g. by age group 1406 as a category) as a reference of an absolute expense for the centered BMI. For example, the pivot may be set as the BMI of an individual (e.g. 35) for estimation of likely future expenses for the individual based on onset of an illness in a future age group (e.g., seniors). For example, to calculate the expense for an individual with a BMI of 40, the coefficient of centered BMI that is output from the regression model is calculated using values obtained by subtracting the BMI of each individual in the group from 35 (i.e. the pivot). Then, to calculate the relative personalized expense for an individual with a BMI of 40, the relative difference (e.g., 5 in the first row of the table below) from the pivot (i.e. 40−35) is multiplied by the coefficient obtained above from the regression model. Consider, as an example, a cohort of individuals with BMI ranging from 25 to 45.

|   | BMI | Pivot at BMI = 35 | Centered BMI |
|---|-----|-------------------|--------------|
| 1 | 40  | 40 − 35           | 5            |
| 2 | 50  | 50 − 35           | 15           |
| 3 | 35  | 35 − 35           | 0            |
| 4 | 25  | 25 − 35           | −10          |
| 5 | 40  | 40 − 35           | 5            |
| 6 | 43  | 43 − 35           | 8            |
| 7 | 35  | 35 − 35           | 0            |

Run the regression model with centered BMIs of all the individuals in the cluster.
a) The coefficient of centered BMI that is output from the regression model is the predicted absolute expense for that BMI (e.g. 35).
b) To obtain predicted expense for the BMI of another individual with BMI of 40, subtract 35 from 40 (i.e. 40−35=5), and then multiply 5 by the coefficient output from the regression model in (a) above.

Centered Age

Referring to FIG. 15, centering by age establishes a pivot point within a subset of data (e.g. by BMI group 1506 as a category) as a reference of an absolute expense for the centered age. For example, the pivot may be the age of an individual (e.g. 45) or the age of onset of an illness in a future age group during the estimation of likely future expenses for the individual. For example, to calculate the expense for an individual of age 60, the coefficient of centered age that is output from the regression model is calculated using values obtained by subtracting the age of each individual in the group (e.g., moderately obese) from 45 (i.e. the pivot). Then, to calculate the relative personalized expense for an individual of age 60, the relative difference from the pivot (i.e. 60−45) is multiplied by the coefficient obtained above.

Consider, as an example, a cohort of individuals with age ranging from 20 to 70 years.

|   | Age | Pivot at Age = 45 | Centered Age |
|---|-----|-------------------|--------------|
| 1 | 20  | 20 − 45           | −25          |
| 2 | 60  | 60 − 45           | 15           |
| 3 | 40  | 40 − 45           | −5           |
| 4 | 50  | 50 − 45           | −15          |
| 5 | 65  | 65 − 45           | 20           |
| 6 | 70  | 70 − 45           | 25           |
| 7 | 30  | 30 − 45           | −15          |

Run the regression model with the centered ages of all the individuals in the cluster.
a) The coefficient of centered age that is output from the regression model is the predicted absolute expense for that age (e.g. 45).
b) To obtain predicted expense for another individual aged 60, subtract 45 from 60 (i.e. 60−45=15), and then multiply 15 by the coefficient output from the regression model in (a) above.

Centering by BMI and/or age is one exemplary embodiment of a similarity function based on actuarial information in a representative sub population.

Interactions

Interactions represent a quantitative contextual and evidence based correlation between illnesses, treatments, the onset of an illness, the duration of an illness, and an individual's health profile such as age, BMI, gender, education, income, occupation, health conditions designated by ICD/HCPCS/CPT codes and onset dates, social history (e.g., smoking, alcoholism, tobacco use, nicotine use, etc.), family history, activities of daily living, activity limitations, vital signs (e.g., blood pressure, blood glucose, cholesterol, etc.), allergies, medications, bone mineral density, immunizations, bio-markers, and genetic disposition. The human genes, the 23 pairs of chromosomes and DNA, and their complex interactions pose high risk of illnesses in individuals who may not necessarily be born with the illness. Diseases such as cancer, diabetes, cardiovascular diseases (e.g., stroke, heart attack, etc.), asthma, neurological disorders, and mental illnesses are influenced by the genetic predisposition of an individual, lifestyle choices (e.g., smoking, alcoholism, etc.) and environmental hazards (e.g., exposure to chemicals, etc.). The onset and duration of such diseases may be aggravated by lifestyle habits of an individual. The analytics model provides the technology to dynamically plugin interactions associated with illnesses, and adapt (retool) the analysis based on variables on an individual basis. Identified interactions are quantified and expressed as variables and applied at any stage of the regression model. The class of an interaction may be classified as: centered-age, square of centered-age, centered-BMI, square of centered-BMI, duration of illness, square of duration of illness, disease, race, gender, ethnicity, income, activities of daily living, limitation in activities, education, family history, smoking, etc. The type of an interaction is either discrete, binary (0/1), or an equation. For example, referring to FIG. 22:
a) Binary: disease, race, gender, age group, BMI group, income (expressed as low, medium, high category), etc.
b) Discrete: age, BMI, centered-age, centered-BMI, square of centered-age, square of centered-BMI, etc.
c) Equation: exponent of the square of centered-age, exponent of the square of centered-BMI, exponent of the square of illness duration, exponent of the interaction between illness and any two variables, etc.

Variables

Referring to FIGS. 23-24, in an exemplary embodiment, variables may be defined manually, imported or computed for use in the first-part, the second-part and/or the final-part of the regression model 1624.
a) Source of Information: Manual, Import (e.g. header fields or tags in a structured CSV/TSV/Excel/XML/JSON data exchange format), Compute (recode, impute, regression output)
b) Category: Dependent or Independent
c) Class: Continuous or Categorical
d) Type: Binary: 0 or 1; Discrete: Integer, Fraction; Equation: Expression based on interactions, other variables, coefficients, weighted coefficients, exponent of coefficients or weighted coefficients, square of coefficients or weighted coefficients, log or natural log of weighted coefficients, rules of exponents, rules of logs.
  i. An equation with an exponential may be expressed as:

[2*exp(duration of illness*coefficient of illness)]

ii. An equation with an exponential of a negative value may be expressed as:

[1/(centered-BMI*coefficient of activity limitation)]

[(1/(centered-age*coefficient of illness)]

iii. An equation as a summation of multiple weighted variables may be expressed as:

[weight−1*(interaction−1*coefficient−1)+weigth−2*(interaction−2*coefficient−2)]

Continuous Variables

For example, the BMI may be input into the model as a continuous variable by entering all values for the BMI.

Categorical Variables

In an exemplary embodiment, the BMI may be input into the model as a categorical variable by separating into categories by healthy weight or overweight/obese. If entered as a categorical variable, then in the calculation of expenses, for individuals with a BMI in the health weight category it may receive a value of '1' and for others it may receive a value of '0'. For example, consider values of BMI for ten individuals in the population sample to set a categorical variable 'healthy_bmi'.

| BMI | Categorical Value |
|------|-------------------|
| 22   | 1 |
| 20   | 1 |
| 24   | 1 |
| 36   | 0 |
| 30.6 | 0 |
| 23.6 | 1 |
| 31   | 0 |
| 33.9 | 0 |
| 35   | 0 | if (BMI='22' or BMI='20' or BMI='24' or BMI='23.6') then {healthy_bmi=1}
else {healthy_bmi=0}

Final Part of the Model

In an exemplary embodiment, in the final part of the regression model 1624, the total lifetime expenses for an individual of interest may be estimated by multiplying the illness expense and probability of the illness with a smearing factor, for each likely illness for the individual of interest over the lifespan, generated by the first and second part of the regression model 1620. The smearing factor is the transformation factor applied to the data after the log-transformed data is converted back to estimates in the original scale. It is obtained by taking the mean of the residuals from the regression model and obtaining the anti-log of those values. Variables are used in this part of the calculus to apply interactions based on the individual of interest's aggregate health profile and indicators for illnesses (comprising of expenses, probabilities, and coefficients) generated by the two-part model 1620. The set of coefficients generated by the two-part model 1620 are multiplied by the value of the variable for the respective coefficient. For example, the set of coefficients may include:

1) Centered-Age
2) Centered-BMI
3) Race
4) Gender
5) Ethnicity
6) Education
7) Income
8) Smoker
9) Family History
10) Activities of Daily Living
11) Σ Disease
12) Σ Duration of Illness
13) Centered-BMI*Σ Disease*Σ Duration of Illness)
14) Centered-Age*Centered-BMI
15) Race*Centered-BMI
16) Gender*Centered-BMI
17) Ethnicity*Centered-BMI
18) Education*Centered-BMI
19) Income*Centered-BMI
20) (Duration of Illness)$^2$
21) Centered BMI*Disease
22) Centered BMI*Disease*Duration of Illness*(Duration of Illness)$^2$
23) Centered Age*Disease*Duration of Illness*(Duration of Illness)$^2$
24) Centered Age*Disease
25) Centered Age*Disease*Duration of Illness The asterisk (*) denotes interaction as a multiplication operator and Σ denotes a summation operator in the calculus of the coefficient.

For example, calculate the expenditure for an individual A with BMI of 30 at centered-age of 20, 30, 40, 50, 60, 70, 80, 90. Then calculate the expenditure for an individual B with BMI of 24.99 at centered-age of 20, 30, 40, 50, 60, 70, 80, 90. The cost difference is the difference of expenditure between the individual A and B.

Calculating Personalized Lifetime Expenses for an Individual

In an exemplary embodiment, the calculation of personalized lifetime expenditures for an individual aged A, with a BMI of B, may be performed as illustrated below.

a) For each illness in a list of illnesses, select all AHPs (with and without illness) from the population set and cluster by age groups.
b) Begin in the age group category for A, with centered-age set to A and centered-BMI set to B.
c) Calculate an expense and probability of the expense in that age group based on likely onset and duration of the illness.
d) Advance to the next forward age group, with centered-age set to the onset of the illness (if applicable) in that age group, with centered-BMI set to B.
e) Proceed to (c) unless life expectancy limit is reached.
f) Repeat for next illness in the list.

Healthcare Risk Score

In an exemplary embodiment, a healthcare risk score (HRS) based on information in an individual's aggregate health profile may be used to calculate a level of financial liability, or risk, inferred from the estimated lifetime expenses for the individual. The HRS may be calculated based on the estimated total lifetime expenses, direct payments by private insurer(s), direct payments by public insurer(s), the individual's out of pocket expenses (copayments, coinsurance, deductibles), and the individual's personal savings in healthcare accounts. The direct payments by insurers decreases HRS, whereas the total expenses and out of pocket expenses incurred by an individual increases HRS. The HRS may be represented, for example, on a scale of 0 to 1000, where a higher value indicates a higher risk.

HRS=[wt*ft(Total Expenditure)+woop*foop(Out of Pocket Expenses)]−[wprv*fprv(Private Insurer Payments)−wpub*fpub Public Insurer Payments)−wmsa*fmsa(Medical Savings Accounts)]

The risk estimation functions (fe) may be based on categorization of the component expenses, payments, and savings, and each category may further be assigned a weighted risk (wr) factor towards the calculation of the HRS. In an exemplary embodiment, the HRS can be outputted to a display device (e.g., monitor, screen, etc.) so that it is displayed in order for a user to view it.

HIRA is one embodiment of a personalized healthcare savings account based on financial incentives provided by the healthcare insurer through reimbursements on paid premiums for achieving a healthy BMI. Other types of medical savings accounts include an individual owned Health Savings Accounts (HSA) or company owned Health Reimbursement Arrangements (HRA).

USE CASE EXAMPLES

The following are examples that illustrate a real world application of the exemplary embodiments of the analytics system as a web-based service and benefit to society. The current aggregate health profile of the individual may be processed by the regression model to predict future illness conditions and estimate anticipated expenses.

a) Hispanic male, aged 62, with BMI of 36 has a history of type 2 diabetes from the age of 35. The individual is on medications for high blood pressure. The family history indicates heart diseases with related deaths. The social history indicates alcoholism and low level of activities of daily living. The blood tests indicate high cholesterol and vital signs include high blood pressure. The predicted future illness conditions may include a stroke between the ages of 60-70 requiring a pace maker, home health services, and a kidney failure between ages 70-80 requiring dialysis. Diabetes may increase the likelihood of expenses due to inpatient (hospital) utilization. The predicted future expenses for the preexisting illness condition (diabetes) may include complications of diabetes such as loss of vision, loss of a limb, or an intensive treatment regimen for control of blood sugar.

b) Caucasian female, aged 25, with BMI of 40 has type 2 diabetes. The individual is on medication to lower A1C. The family history indicates neurological disorders in first-degree relatives. The social history indicates alcoholism. The health records indicates hypertension. The predicted future illness conditions may include a heart attack between the ages of 50-60 requiring angioplasty, and multiple sclerosis or Parkinson's disease between the ages of 70-80. The predicted future expenses for the preexisting illness condition (diabetes) may include long-term medical management to lower A1C.

c) Asian male, aged 70, with BMI of 46 has a history of depression, nervous weakness and pain while walking or standing from the age of 40. The family history shows knee replacement because of osteoarthritis in a parent. Social history shows walking limitations and low level of activities of daily living. The eating habits indicates a low protein diet. The health record indicates a low bone mineral density and low level of iron and vitamin D. The predicted future illness conditions may include onset of rheumatoid arthritis or multi symptom atrophy between the ages of 75-85. The predicted future expenses may include home health services and therapy to improve activities of daily living.

Computing Systems for Predictive Healthcare Expenditures

Figure 1:
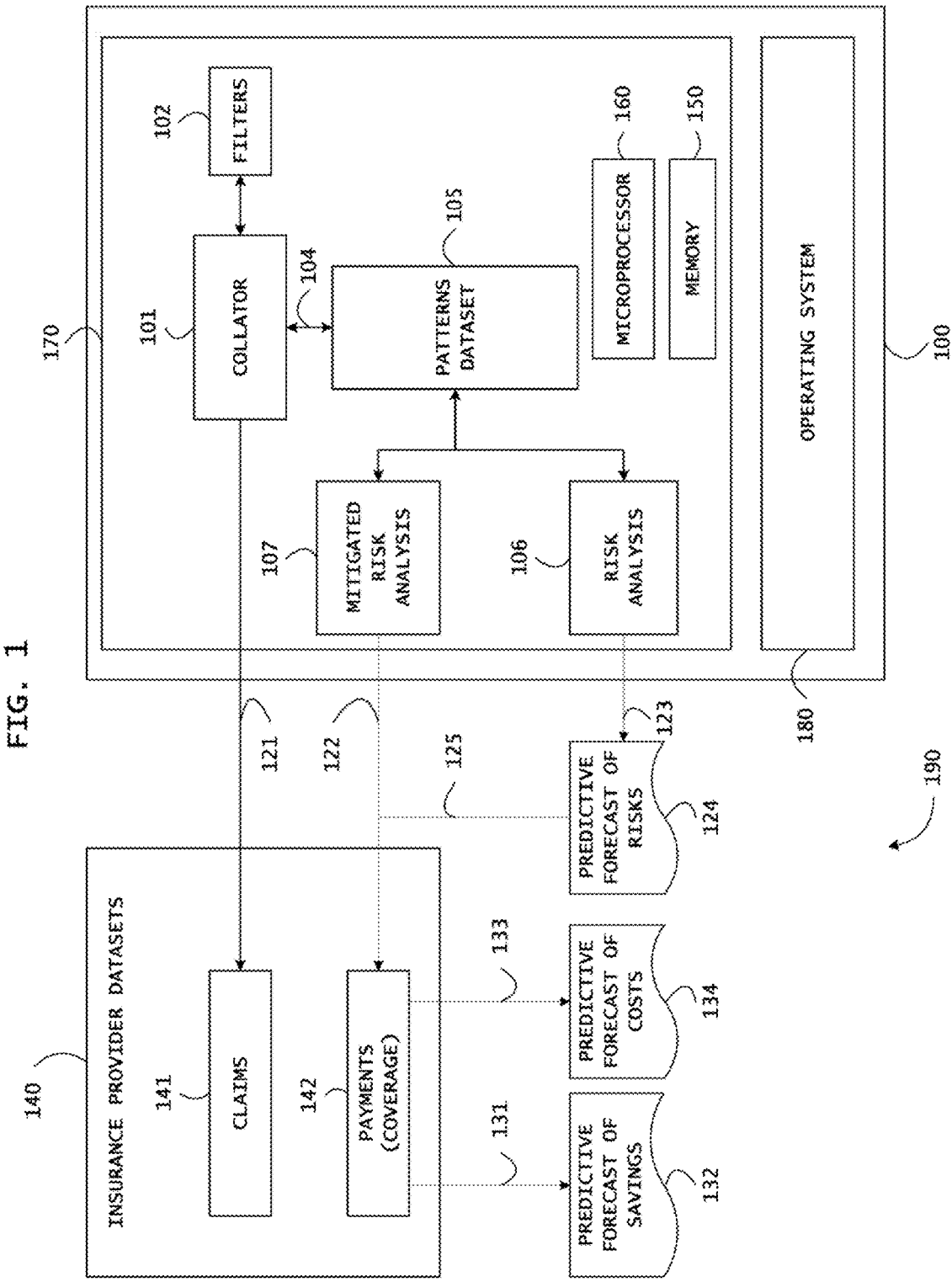
FIG. 1 is a schematic diagram illustrating an exemplary system/architecture in accordance with various exemplary embodiments.

FIG. 1 is a schematic diagram illustrating an exemplary predictive analysis system 190 in accordance with various exemplary embodiments.

Referring to FIG. 1, the predictive analysis system 190 includes a services platform 100 and insurance provider datasets 140 including electronic claims repositories 141 and insurance payments (or coverage plans) datasets 142. The services platform 100 may include an operating system 180, microprocessor 160, a memory 150, a collator 101 to consolidate multiple disparate datasets, at least one relevant filter 102 to include various elements contained in the datasets, a means to generate trends and build a patterns dataset 105, a means to perform risk analysis 106, a means 123 to estimate predictive forecast of risks 124, a means to perform mitigated risk analysis 107, a means to import datasets 121 from an insurance provider's electronic claims repositories 141, a method to import datasets 122 from insurance payments (or coverage plans) datasets 142, a means 131 to generate predictive forecast of cost reductions (savings) 132, a means 133 to generate predictive forecast of costs (payments) 134, and a means 125 to generate predictive forecast of costs 134. The insurance provider datasets 140 may include a plurality of electronically stored information, for example, insurance, medical and/or health records, and other data that may be used in performing the functions disclosed herein. The services platform 100 may also include additional components not illustrated in FIG. 1 suitable for performing the functions discussed herein, such as one or more communication devices (e.g., transmitting and/or receiving devices) for transmitting and receiving data from the insurance provider datasets 140 and other data sources, one or more input devices for the input of data by a user, one or more display devices for the display of data to a user, etc. It will be apparent to persons having skill in the relevant art that the configuration of the predictive analysis system 190 illustrated in FIG. 1 is provided as an illustration only, and that additional configurations may be suitable for performing the functions discussed herein. For instance, in some embodiments, the services platform 100 and insurance provider datasets 140 may be included in a single computing device or computing system.

Figure 2:
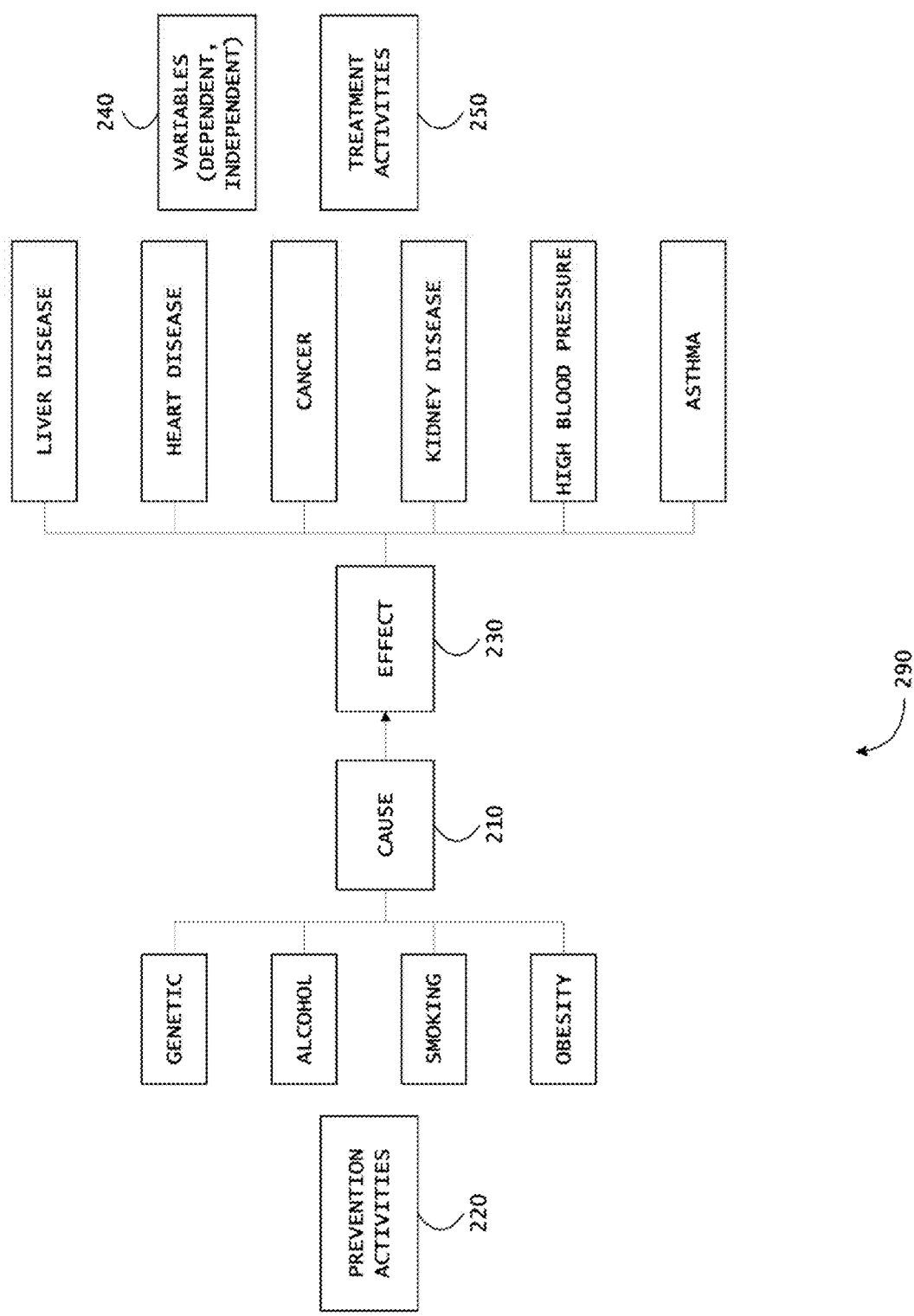
FIG. 2 is a schematic diagram illustrating a method to model cause-effect and prevention-treatment relationships in accordance with various exemplary embodiments of the disclosed system.

FIG. 2 is a schematic diagram illustrating an exemplary cause and effect relationship modeling system 290 in accordance with various exemplary embodiments.

Referring to FIG. 2, the cause-effect relationship modeling system 290 may include a means for cause analysis 210 (for example, illnesses correlated to genetics, alcohol, smoking, obesity, etc.), a means for effect analysis 230 (for example, illnesses as liver disease, heart disease, cancer, kidney disease, high blood pressure, asthma, etc.), prevention activities database 220, treatment activities database 250, and a plurality of dependent and independent variables 240. The means for cause analysis 210 and means for effect analysis 230, and/or the entire cause-effect relationship modeling system 290, may be implemented using the predictive analysis system 190 illustrated in FIG. 1 and discussed above. For instance, the microprocessor 160 of the predictive analysis system 190 may be configured to perform the cause analysis and effect analysis, and the memory 150 of the predictive analysis system 190 may be configured to store the prevention activities database 220, treatment activities database 250, and dependent and independent variables 240. Dependent and independent variables 240 may include variables suitable for use in determining healthcare expenditures for an individual, as discussed below, such as age, gender, weight, body mass index, disease length, personal expenditures, etc.

Incentives Based Healthcare Policy

FIG. 3 is a schematic diagram illustrating an exemplary incentive based healthcare policy 390 in accordance with various exemplary embodiments.

Referring to FIG. 3, the healthcare incentives system 390 includes a health insurance recipient 301, an insurance provider 303, a government entity (state or federal) 304, a healthcare services provider 305, an employer 302 of the recipient 301, a healthcare individual reimbursement account 306 of the recipient 301, managed investments 307, government tax collections (income, social security, Medicare, etc.) 321, a matching healthcare contribution by a government entity 329, a healthcare expense (for example, co-payments, co-insurance, deductibles, etc.) 322, an out-of-pocket health insurance premium 323, a healthcare claim payment 326, an employer-paid healthcare premium 327, an insurance reimbursement 328 to the health reimbursement account 306 and contributions 325 to managed investments 307.

As discussed in more detail below, the healthcare services provider 305, insurance provider 303, or other suitable entity (e.g., such as a third party entity not illustrated in FIG. 3) may be configured to predict healthcare expenditures incurred by the recipient 301, such as for use in determining insurance costs or other payments made in use of the healthcare incentives system 390, such as the healthcare expense 322, insurance premium 323, healthcare claim payment 326, etc. As discussed in more detail below, a prediction of incurred healthcare expenses may be made based on interactions between diseases and data associated with recipients 301, such as age, gender, and a body mass indicator, such as a body mass index value. The interactions and individual data may be used to predict an average expenditure by an individual (e.g., or associated with an individual, such as may be paid by the healthcare services provider 305 and/or insurance provider 303), which may be combined with a predicted probability that an individual may get a disease to determine the predicted expenditure that may be incurred by a recipient 301. The prediction may then be used by the healthcare services provider 305, insurance provider 303, or other entity as part of the healthcare incentives system 390.

For instance, as discussed in more detail below, a prediction may be made that a recipient 301 of body mass index indicating that the recipient is overweight will incur $10,000 of medical expenses within a period of time (e.g., 1 year, 5 years, 10 years, etc.) or as a result of a specific disease (e.g., for which the predictive analysis was performed). A prediction may also be made that a recipient 301 of a body mass index indicating a healthy weight will only incur $2,000 of medical expenses using the same metric. As such, the healthcare services provider 305, insurance provider 303, government 304, employer 302, or other entity may provide incentives to the recipient 301 to lower their body mass index to a healthy value. Incentives may include, for instance, rebates to the recipient 301, contributions to the healthcare individual reimbursement account 306, etc.

Statistical Analysis for Predictive Healthcare Expenditures

FIG. 4 is a flowchart illustrating a method 400 in accordance with various exemplary embodiments. The method 400 provides a first part of the model for statistical analysis on datasets to compute healthcare expenditures based on a plurality of variables.

The algorithm described in FIG. 4 is applied iteratively for each illness (disease), and by healthy BMI and unhealthy (overweight and obese) BMI, for each individual in the cohort (sample set).

At block 401 of FIG. 4, for the first part of the model, the total expenditures for a disease may be calculated using the sum of facility, physician and individual expenditures for emergency room visits, ambulatory care, home health and non-health agency services usage, outpatient care, inpatient care and hospitalization, zero night stays, prescription drug usage, and out of pocket expenses (premiums, co-payments, co-insurance, deductibles) during the year. The diseases, for which total expenditures are calculated, may be identified using standardized International Classification of Diseases (ICD) codes, such as codes for diabetes (DIABDX, ICD 9 code '250'), heart disease (angina or myocardial infarction or other heart disease or coronary heart disease, ICD 9 codes 410, 412, 413, 414, 415, 416, 423, 424, 426, 427, 428, 429), high blood pressure (BPMLDX, ICD 9 Code 401), stroke (STRKDX, ICD 9 codes 430-436), arthritis (ARTHDX, ICD 9 code715.00-715.98), mental diseases (ICD9 codes for depression, anxiety, alcoholism, drug abuse: '295', '296', '311', '312', '313', '296', '300', '301', '303', '304', '305', '309'), cancer (breast cancer: ICD9CODX, '174', 'V10', '85')); Colon Cancer: ICD 9 codes, '153', '154', 'V10', '45', '49')), etc. Other codes, such as CPT (Current Procedural Terminology) and HCPCS (Healthcare Common Procedure Coding System) may also be used. The expenditure data and/or codes may be stored in the predictive analysis system 190, such as stored in the memory 150 as healthcare expenditure data.

At block 402, values of total expenditures greater than zero may be converted to natural log of expenditures. The conversion may be performed by the microprocessor 160 of the predictive analysis system 190, or other suitable component. In some instances, the natural log value of healthcare expenditures may be stored in the memory 150, such as following calculation by the microprocessor 160 or upon receipt of already-converted values that may be provided to the predictive analysis system 190, such as part of the insurance provider datasets 140.

At block 403, independent variables from the datasets that may include at least age, BMI, race, gender, ethnicity, education status, diseases (diabetes, high blood pressure, heart disease, stroke, breast cancer, prostate cancer, arthritis, mental conditions), duration of illness (0 and 45 years), insurance status, and interactions of the disease with its duration, square of the duration, age and BMI, etc. may be categorized into groups. For instance, individuals may be categorized into two age groups, such as a first age group for ages 0-64 and a second age group for ages above 65 years. In some instances, the groups may be anonymized, such as via the use of coding or other techniques, such as coding the age variable as 0 for age group 0-64 and 1 for the age group of 65 and above. The BMI for individuals may be categorized as healthy weight (BMI less than 24.99), overweight (BMI between 25 and 29.99), or obese (BMI above 30). BMI may be calculated using the formula (weight (lb.)/ height (in)$^2$)*703. In some embodiments, other types of body mass indicators may be used, such as using different calculations, different categorizations, etc. Race may be categorized as White (Caucasian), Black, American Indian/ Alaskan Native, Asian, Native Hawaiian, Multiple race, etc. Ethnicity may be categorized as Hispanic or Non-Hispanic. Education Status may be categorized with 1 through 8 years of education being coded as elementary education; 9 through 12 years of education as high school; 13-17 years of education as college; and higher as post-graduate. Insurance Status may be categorized as private, public (for example Medicare, Medicaid, Tricare, SCHIP or other public programs), and uninsured. Additional types of categorizations will be apparent to persons having skill in the relevant art. In some embodiments, the independent variables and/or categorizations based thereon may be stored in the memory 150 of the predictive analysis system 190. For instance, individual healthcare data may be stored in the memory 150, with the categorized variables stored for each individual as individual characteristics. In some instances, a variable may be included that indicates that the individual is associated with a particular disease or is not associated with the particular disease.

At block 404, all the variables may be dummy coded. Dummy coding of the variables may include coding as described above with respect to categorization, or other form of anonymization of the variables. For instance, insurance status for an individual may be coded as 1 for private insurance, 2 for public insurance, and 3 for uninsured, such that the insurance status of an individual may not be readily identified when viewing their healthcare data. For example, an individual's insurance status may show as "3," which may prevent a user that is unaware of the coding or anonymization of the data from identifying the type of insurance the individual has, which may provide additional security as to the individual's healthcare data.

At block 405, interactions with disease and age; disease and body mass index; disease and duration may be computed, such as by the microprocessor 160 of the predictive analysis system 190. Interactions may be based on individual healthcare data (e.g., stored in the memory 150) for each disease. For instance, interactions may be computed for those individuals indicating as being associated with the disease, and may be based on data at the time the individual had or has the disease. Interactions may be represented using any suitable method, such as an equation, variable, discrete value, etc. For example, the interaction between disease and age may be a discrete set of points for each age, may be an equation based on age, etc.

Since the datasets may comprise of multiple zero values to represent bad debt, free care, etc., a two-part regression model may be adopted in the prediction of expenditures. At block 406, the first part of the model, a regression model on the subsample of individuals with expenses may be used to model a relationship between the dependent variable, natural log of the expenses, and the independent variables. The regression model may be applied to the data by the microprocessor 160 of the predictive analysis system 190. In some instances, the regression model itself and/or algorithms for the application thereof may be stored in the memory 150 of the predictive analysis system 190.

At block 407, variance control strategies may be adopted. In certain exemplary embodiments, Taylor series linearization methods to use Variance Estimation Strata (VARSTR) and Variance Estimation Primary Sampling Units (VARPSU) within the strata may be adopted to obtain variability of the survey estimates of expenditures of medical illnesses. Other methods of variance estimation may also be adopted. In some instances, the data may be weighted by an individual's weight and/or their body mass indicator, as stored in individual healthcare data. Adoption of variance control strategies and weighting of individual data may be performed by the microprocessor 160 of the predictive analysis system 190. At block 408, changes in R-square may be monitored by the microprocessor 160 to determine a fit model.

At block 409, expenditures may be predicted for individuals with a specific illness or disease by obtaining the sum of standard beta coefficients of the illness (where disease=1), and its interaction with its duration, body mass indicator, and age. In some instances, expenditure predictions may be adjusted for by race, ethnicity, gender, insurance status, educational status, and any other individual characteristic among overweight or obese individuals (e.g., based on body mass indicator) over one year in log dollars. The log dollars may be converted to raw dollars by taking the inverse of the log to obtain the predicted expenditure, which may be herein referred to as VALUE#1. The prediction of expenditures and adjustment thereof may be performed by the microprocessor 160 of the predictive analysis system 190.

At block 410, expenditures may be predicted for individuals without the specific illness or disease by obtaining the sum of standard beta coefficients of the illness (disease=0), and its interaction with its duration, body mass indicator, and age. Such expenditures may include out of pocket expenses for preventive measures (e.g. mammograms, colonoscopy, cancer screening, blood tests, annual physical/wellness visits), and insurance payments (premiums, co-payments, deductibles, co-insurance). In some instances, expenditure predictions may be adjusted for by race, ethnicity, gender, insurance status, educational status, and any other individual characteristic among overweight or obese individuals (e.g., based on body mass indicator) over one year in log dollars. The log dollars may be converted to raw dollars by taking the inverse of the log to obtain the predicted expenditure, which may be herein referred to as VALUE#2. The prediction of expenditures and adjustment thereof may be performed by the microprocessor 160 of the predictive analysis system 190.

FIG. 5 is a flowchart illustrating a method 500 in accordance with various exemplary embodiments. The method 500 provides a second part of the model (i.e., continuation of the first part depicted in FIG. 4) for statistical analysis on datasets to compute probabilities of healthcare expenditures based on a plurality of variables.

The algorithm described in FIG. 5 is applied iteratively for each illness (disease), and by healthy BMI and unhealthy (overweight and obese) BMI, for each individual in the cohort (sample set).

At block 501, a variable IF_EXP may be created for total expenditures greater than zero. The creation of the variable may be performed by the microprocessor 160 of the predictive analysis system 190. In some instances, the variable may be dummy coded for the second part of the model.

At block 502, the second part of the model may use binary logistic regression to predict the probability of having expenditure among overweight or obese individuals with the specific illness (e.g., where disease=1). The dependent variable IF_EXP (set to 1 if individual has expenditure and 0 if no expenditure) and independent variables may be the same as the ones used in the first part of the model illustrated in FIG. 4 and discussed above. The probability of predicting expenses among individuals with the illness may be calculated from exponentiation of B or $e^B$, where B is the sum of the coefficients of the disease, and its interaction with its duration, body mass indicator, and age, which may be adjusted for race, ethnicity, gender, insurance status, educational status, and other individual characteristic to obtain the probability, which may be referred to herein as VALUE#3. The prediction of the probability may be performed by the microprocessor 160 of the predictive analysis system 190.

At block 503, the second part of the model may use binary logistic regression to predict the probability of having expenditure among overweight or obese individuals without the specific illness (e.g., where disease=0). The dependent variable IF_EXP (set to 1 if individual has expenditure and 0 if no expenditure) and independent variables may be the same as the ones used in the first part of the model illustrated in FIG. 4 and discussed above. The probability of predicting expenses among individuals without the illness is calculated from exponentiation of B or $e^B$, where B is the sum of the coefficients of the disease, and its interaction with its duration, body mass indicator, and age, which may be adjusted for race, ethnicity, gender, insurance status, educational status, and other individual characteristic to obtain the probability, which may be referred to herein as VALUE#4. The prediction of the probability may be performed by the microprocessor 160 of the predictive analysis system 190.

FIG. 6 is a flowchart illustrating a method 600 in accordance with various exemplary embodiments. The method 600 may provide statistical analysis on datasets, based on the first and second parts of the model (depicted in FIGS. 4 and 5), to compute healthcare expenditures and probabilities based on a plurality of variables.

The algorithm described in FIG. 6 is applied iteratively for each illness (disease), and by healthy BMI and unhealthy (overweight and obese) BMI, for each individual in the cohort (sample set).

At block 601, a predicted expenditure incurred for overweight or obese individuals with illnesses may be obtained by multiplying the predicted probability of having expense (VALUE#3) from the second part of the model by its predicted expenditure (VALUE#1) obtained from the first part of the model. The predicted incurred expenditure may be referred to as VALUE#5. The predicted incurred expenditure may be calculated by the microprocessor 160 of the predictive analysis system 190. In some instances, the microprocessor 160 may calculate multiple predictive incurred expenditures for a plurality of different individual characteristics, such as for each of a plurality of different age groups, genders, etc. and combinations thereof, for individuals with the specified body mass indicator (e.g., overweight or obese BMI in the example illustrated in FIG. 6).

At block 602, a predicted expenditure incurred for overweight or obese individuals without illnesses may be obtained by multiplying the predicted probability of having expense (VALUE#4) from the second part of the model by its predicted expenditure (VALUE#2) obtained from the first part of the model. The predicted incurred expenditure may be referred to as VALUE#6. The predicted incurred expenditure may be calculated by the microprocessor 160 of the predictive analysis system 190. In some instances, the microprocessor 160 may calculate multiple predictive incurred expenditures for a plurality of different individual characteristics, such as for each of a plurality of different age groups, genders, etc. and combinations thereof, for individuals with the specified body mass indicator (e.g., overweight or obese BMI in the example illustrated in FIG. 6).

At block 603, a difference in expenditure (herein referred to as VALUE#7) may be obtained by calculating the different between VALUE#5 and VALUE#6, which may represent a predicted average per person increase in expenditure due to a person having the specific illness. To correct for transformation bias, the increase (VALUE#7) may be multiplied by a Bias Correction Factor (BCF) or a smearing factor. The smearing factor may be calculated by taking the antilog of the mean of the residuals. The calculations performed in identifying the difference in expenditure may be performed by the microprocessor 160 of the predictive analysis system 190, and may use data stored in the memory 150, such as the BFC or smearing factor.

At block 604, the prior steps (e.g., in the first and second models and blocks 601, 602, and 603) may be repeated for additional body mass indicators (e.g., healthy weight individuals according to BMI) to calculate increase in expenditures for healthy weight individuals. The value, which may be represented as VALUE#8, may be, as discussed above, representative of the increase in expenditure for an individual having the associated body mass indicator when faced with the illness. In some of these instances, each of these steps may also be performed for different groups of individuals with respect to other individual characteristics in addition to body mass indicator, such as repeating the steps for each body mass indicator for multiple age groups, genders, ethnicities, and/or combinations thereof.

FIG. 7 is a flowchart illustrating a method 700 in accordance with various exemplary embodiments. The method 700 provides statistical analysis on datasets to compute healthcare cost reductions, prevalence of individuals with inadequate activities in daily living and functional limitations, and total expenditures for the population with the specific illness.

At block 701, a cost reduction may be calculated as the weighted average of difference in predicted expenses between overweight or obese individuals (VALUE#7) and healthy weight individuals (VALUE#8) with the specific illness. This calculation may be performed by the microprocessor 160 of the predictive analysis system 190. The cost reduction may also be calculated for additional body mass indicators as appropriate. For instance, if the predicted expenses for individuals for each of five different body mass indicators is calculated, the microprocessor 160 may calculate four or more cost reductions (e.g., from each indicator to the next proceeding toward a healthy weight). Cost reductions may be used, for instance, for the providing of incentives for an individual moving from one body mass indicator to another, such as rebates or contributions to a HIRA 306.

At block 702, the total expenditures for individuals in the population with the illness may be calculated for overweight and obese individuals by multiplying the average per person increase in expenditure for the associated body mass indicators by the total number individuals with the illness having that body mass indicator in the sample This calculation may be performed by the microprocessor 160 of the predictive analysis system 190 and may be used, for instance, by the insurance provider 303 in the setting of premiums, payment of claims, etc.

At block 703, the total expenditures for individuals in the population with the illness may be calculated for individuals having a healthy weight by multiplying the average per person increase in expenditure for the associated body mass indicators by the total number of healthy weight individuals with the illness in the sample. This calculation may also be performed by the microprocessor 160 of the predictive analysis system 190.

At block 704, the prevalence of individuals with inadequate Activities of Daily Living (ADL) and functional limitations using variables such as difficulties in standing, bending, reaching overhead, physical limitations, housework limitations, social and cognitive limitations, among individuals associated with various body mass indicators may be calculated. The prevalence may be calculated, for instance, by the microprocessor 160 of the predictive analysis system 190. The microprocessor 106 may also be configured to perform analysis regarding ADL and the effect of various body mass indicators on ADL, as reducing weight is expected to improve ADL.

At block 705, the prevalence of diseases among individuals by BMI or other body mass indicator value and age may be calculated. The prevalence may be calculated based on healthcare data, such as stored in the memory 150 of the predictive analysis system 190, for individuals using the microprocessor 160. At block 706, the annual healthcare premiums categorized by family income may be calculated. The family income may be an individual characteristic stored in the healthcare data for the respective individual in the memory 150, which may be used by the microprocessor 160 in the categorization of healthcare premiums. At block 707, the average cost may also be modeled as a function of the discount rate, the survival probabilities of the individual with the health condition, and the average costs for the individual with each year past onset of illness. The average cost may be modeled by the microprocessor 160 of the predictive analysis system 190, which may utilize one or more modeling algorithms stored in the memory 150.

Referring to FIGS. 4-7, the modified two-part regression model may be executed to generate values (VALUE#1 through VALUE#8) for any disease, to estimate disease associated future expenditures for individuals with unhealthy and healthy BMI.

| Unhealthy BMI | Healthy BMI | |
|---|---|---|
| VALUE#1 | VALUE#1' | Expenditure with disease |
| VALUE#2 | VALUE#2' | Expenditure without disease |
| VALUE#3 | VALUE#3' | Probability of expenditure with disease |
| VALUE#4 | VALUE#4' | Probability of expenditure without disease |
| VALUE#5 | VALUE#5' | Predicted expenditure with disease |
| VALUE#6 | VALUE#6' | Predicted expenditure without disease |
| VALUE#7 | | Predicted increase in expenditure for disease duration |
| | VALUE#8 | Predicted increase in expenditure for disease duration |

Graphical Representation of Differential Analysis

FIG. 8 is a graphical representation illustrating differential analysis, generated from a calculus on datasets, of predicted lifetime costs, and predicted cost reductions based on projected availability of HIRA funds, by age and category.

At reference point 801, lifetime healthcare costs with BMI relevance (including at least out-of-pocket expenses and insurance payments) are predicted by age and BMI category. Reference points 802, 803 and 804 exemplify the predicted cost trajectories for populations in healthy, overweight and obese BMI categories respectively. Reference points 805 and 806 exemplify the cost reductions realized by achieving a healthy BMI in populations.

At reference point 807, availability of HIRA funds may be predicted by age and income category. Reference points 808, 809 and 810 exemplify the predicted trajectory of reserves in HIRA for populations in the low, middle and high-income categories respectively. Reference point 811 exemplifies predicted funds available through the HIRA at the age of onset of medical treatments to offset predicted healthcare expenses, thereby reducing direct payments to healthcare recipients by the healthcare insurance provider.

Benefits and Advantages of Predictive Analytics

The predictive analytics are performed on electronically stored information (raw data representation). The results of the analysis may be used to predict the incidence (occurrence) risks and lifecycle (for example, onset, duration, etc.) of specific diseases and the lifetime payments for such illnesses (or diseases) by insurance providers (for example, federal or state governments, private, etc.).

The forecasting of medical expenditures based on BMI provides insurance providers the ability to monitor high-risk recipients (members) and implement quality improvement initiatives to mitigate evidence-based risks taking into account the specific needs of members to increase the likelihood of desired health outcomes. The predictive analysis may be rendered as electronically stored information and shared with healthcare services providers (for example, hospitals, physicians, home-hospice, etc.) to facilitate appropriate guidance and decisions in patient care.

The predictive analysis model includes a plurality of independent variables that cause or promote obesity. These medical evidences may include at least the family history, age of onset of obesity, injury history, sleep disorders, effect of enzymes and other proteins in the blood, hormonal imbalances, endocrinological disorders, genetics, drug influences, emotions (e.g., boredom, sadness, anger, etc.), environmental influences, surgical history, allergies, eating disorders, religious activities, social activities, social influences (e.g., bullying, abuse, etc.), and regular diet composition (e.g., meat, fish, poultry, fruits, vegetables, formula foods, genetically modified foods, alcohol, etc.).

In one exemplary embodiment, the microprocessor 160 may estimate the average per person increase in predicted expenditures amongst BMI categories and the cost reduction as a cost differential when members achieve healthy BMI. BMI and a plurality of variables may be applied as categorical variables rather than continuous variables. Annual expenditures categorized by type of insurance provider for each disease may be calculated for BMI categories. The RAND Corporation Health Insurance Experiment (RAND HIE) two-part model has been modified to estimate expenditures amongst BMI categories for each disease predisposed by obesity.

In another exemplary embodiment of the disclosed apparatus, system, and method, weighting may be performed by frequency of obese, overweight and healthy weight members with a disease in the appropriate age group in the estimation of expenditures for the associated disease. Calculations discussed herein may hypothesize improved Activities of Daily Living, after obese or overweight members achieve healthy BMI, as a measure of indirect benefit and compound effect on lifetime cost reduction. In certain exemplary embodiments, partial premium reimbursements (e.g., as financial incentives) for achieving a healthy BMI by the healthcare insurer to the beneficiary may be rolled into a Healthcare Individual Retirement Account (HIRA), analogous to traditional or Roth IRA accounts. In certain exemplary embodiments, an employer may provide a matching contribution to the employee's HIRA account.

The present embodiments describe a solution that comprises of a data driven model for all healthcare beneficiaries (e.g., healthy and unhealthy), to estimate pre-disease and post-disease out-of-pocket and premium costs based on voluntary life style choices requiring no intervention to achieve and maintain a healthy BMI. The model is applied to estimate direct and indirect cost reductions to healthcare service providers and insurers based on delaying the onset, duration and intensity of a plurality of diseases that each individual is most likely to suffer in the future over a lifetime based on personal history, probabilities, categorized dependent and independent variables that change over the lifetime of the individual. The individual, for the purpose of these calculations, does not have to be currently under treatment for any condition by a healthcare provider (by a physician or at a facility). The model therefore predicts cost of treatment before any illness occurs in a healthy or unhealthy individual.

The exemplary embodiments are fundamentally different from other models that predict the most cost-effective intervention in a subject with an illness. Such other models may comprise of simulated virtual subjects, risk functions from which a benefit and function is derived to predict cost effectiveness of interventions necessary to avert medical events. The other models imply an existing disease condition requiring a decision by the healthcare service provider to offer treatment at a level that cost effectiveness is achieved towards a most improved outcome. Further, the other models involve a treatment cycle where the subject has medical condition(s) and is seeking treatment(s), which may be provided as a preventive measure to avert a medical event in the future.

The other models in other approaches do not estimate cost difference as a result of applying a particular intervention in a subject with the medical condition and an unhealthy BMI, versus a subject with the medical condition and a healthy BMI. Other models strictly apply the intervention on a subject for the purpose of cost effectiveness to achieve a desirable outcome given that the medical condition has already occurred in the subject. These other models generate risk functions based on type of intervention to determine the most cost effective intervention for an existing medical condition that needs to be treated. Weight loss in a simulated subject may be either a loss of body fat or body water, and therefore temporary in nature.

In the exemplary embodiments, the calculation of risk (e.g., a risk function) and cost reduction (e.g., benefits and cost functions) are fundamentally different from other approaches. Weight loss explicitly means reduction in BMI and sustaining a healthy BMI throughout lifetime. Further, weight loss is not viewed as a medical intervention, but as a voluntary lifestyle choice of the individual. The exemplary embodiments may generate a two-part model where the first part determines the total lifetime expenditures for an individual by illness, and the second part determines the probability of such expenditures for the individual based on disease interactions and dependent and independent variables. Further to estimate cost reduction, the two parts can be reapplied for individuals with (a) Unhealthy BMI with the illness, (b) Unhealthy BMI without the illness, (c) Healthy BMI with the illness, (d) Healthy BMI without the illness, etc. In particular, exemplary embodiments of the model do not advocate ranking members by benefits of intervention(s), or determining cost effectiveness of any set of treatments given a medical condition (episodic).

Contrary to models that suggest the use of metadata and decision processes at the level of detail as typically applied by healthcare stakeholders, the exemplary embodiments may use data sources retrieved from healthcare insurance companies including payments to healthcare insurance providers (private and public) and healthcare recipients, and member costs including premiums and out of pocket costs. The data sets may be historic and actuarial as retrieved from said data sources.

Other approaches determine cost difference based on continuing with or without intervention on an episodic basis (post disease condition), where a decision to apply an intervention is required to avert adverse medical events. The cost reduction is then limited to the chosen intervention and episode. In contrast, the approach discussed herein may determine cost reduction as a combination of pre-disease and post-disease activity; estimates lifetime reduction of expenditures for individuals, healthcare service providers, and insurers before any disease condition occurs; and estimates lifetime reduction of expenditures for healthy and unhealthy recipients of healthcare services. The cost differential may be based on sustaining BMI over age. The model is therefore a lifetime model and not an episodic model.

In an exemplary embodiment, risk is not calculated based on types of interventions required for a disease condition once that condition occurs in an individual. Instead, the system predicts the probabilistic onset and duration of an illness based on independent and dependent variables and estimates future costs irrespective of what interventions may be chosen by a healthcare provider. The model forecasts future costs based on illnesses that are most likely to occur in an individual irrespective of any possible intervention post-disease. In post-disease condition, it estimates lifetime cost reductions based on the individuals BMI markers incrementally over the duration of the illness. For example, the model estimates the lifetime healthcare costs based on age and BMI for healthy and unhealthy individuals (a) a 16-year old individual with unhealthy BMI and no preexisting disease condition, (b) a 16-year old individual with healthy BMI and no preexisting disease condition, (c) a 16-year old individual with unhealthy BMI and diabetes, (d) a 55-year old individual with unhealthy BMI and no preexisting disease condition, (e) a 55-year old individual with healthy BMI and no preexisting disease condition, (f) a 65-year old individual with healthy BMI and with a disease condition, (g) a 65-year old individual with unhealthy BMI and with a disease condition, etc.

In an exemplary embodiment, a list may be generated that has no rankings. The cost estimates may be generated for all individuals (e.g., unhealthy and healthy BMI or any other type or range of body mass indicators) to achieve and maintain healthy BMI. An individual may not require any medical intervention. A complex statistical regression methodology may be used in the methods discussed herein that has two parts. As discussed above, the first part may use a linear regression model predicts the expenditures for individuals with and without illness using interactions of the illness with factors such as age, BMI, and duration of the illness. As also discussed above, the second part may use binary logistic regression to predict the probability of incurring expenditures (physician and facility) with and without illness. The cost reduction may then be estimated for unhealthy individuals and also for healthy individuals. No virtual simulated patients are required in the model. The algorithm inputs real patient data into a validated regression model, instead of data representing virtual patients. The variables are categorical (such as diabetes, age groups, race, BMI groups, etc.) and not limited to continuous. Weight loss explicitly means reduction in BMI and sustaining healthy BMI throughout lifetime, unlike weight loss in a simulated subject that may be either a loss of body fat or body water and therefore temporary in nature.

In some instances, the average cost may be modeled as a function of discount rate, survival probabilities of the individual with the health condition, and the average costs for the individual with each year past onset of illness. In some cases, the individual in the model does not have to be seeking any healthcare service (by a physician or at a facility) as the model can also be applied to healthy individuals. The beginning variables therefore do not relate to a particular individual seeking a healthcare service requiring an intervention of some kind for treatment of the medical condition.

The approach advocates achieving a healthy BMI through voluntary life style choices and incentives to prevent early onset of illness or medical condition in the future based on the probabilistic likeliness of an individual to reach a medical condition based on risk profile, rather than preventive steps to be taken to avoid adverse medical outcomes. In contrast to approaches that predict the probability that a patient will remain or become a high user of medical services, the methods discussed herein forecasts expenses of the beneficiary for a disease condition. Incremental lifetime costs are a continuous differential analytics as a person's health indicator, activities of daily living, insurance premiums and payments, and service provider costs vary over time. The dependent variable can be the total expenditures (including out of pocket expenses) and not merely the utilization of medical services. The independent variables may include at least the family history, disease interactions, age groups, activities of daily living, onset, duration and progression of the disease, and not merely variables during the period of medical treatment utilization. No interventions are required. The methods discussed herein may predict total expenses including out of pocket expenses by body mass index.

The solution discussed herein proposes a cost estimation model for health care beneficiaries (e.g., with out of pocket costs) and service providers (e.g., insurers and healthcare providers) to forecast costs before need arises for any treatment, to avert or delay onset of disease condition, and reduce the cost impact of the disease should the disease condition occur (i.e. pre-disease). For post-disease condition, cost estimation may include the impact of BMI on multiple complications based on patient profile, activities of daily living, life style choices, disease progression and scope of cost reduction based on achieving a healthy BMI through the disease condition. This does not suggest any medical treatment options as a cost-benefit function. The models cited in prior-art use cost forecasts to deliver treatment based on a cost-benefit model to achieve the most desirable outcome.

The lifetime cost estimation may be a continuous differential analytic as a person's health indicators, activities of daily living, insurance premiums and charges, and service provider costs vary over time. The incremental multi-stage analysis processes dependent and independent variables that are constantly in flux to derive more accurate predictive estimates. In the models cited in prior-art the costs estimation is not continuous over the lifetime as a treatment decision is required and a spot assessment is necessary. The methods discussed herein predict lifetime costs for all individuals based on their body mass index irrespective of their employment history using multi stage regression analysis. Variables such as gender, race, ethnicity, and any other suitable individual characteristic, particularly those related to healthcare, are demographics that may be used in predicted estimates of health care costs. They are indicative of an individual.

The variables may include at least dependent and independent variables related to obesity. These variables may change as new variables relevant to obesity are discovered. As discussed herein, a BMI of less than 24.99 may refer to healthy weight. A BMI between 25 or 29.99 may refer to overweight (e.g., an unhealthy weight), and a BMI of above 30 may refer to obese (e.g., unhealthy weight). It will be apparent to persons having skill in the relevant art that a determination of healthy or unhealthy weight may change over time and based on circumstances, which may result in different BMIs corresponding to different determinations of health. In addition, in some instance, different metrics may be used for representation of an individual's health based on body mass.

As used herein, "pre-disease" may refer to calculations that involve individuals without the illness (or disease condition). The term "post disease" may refer to calculations that involve individuals with the illness or after the onset of illness. The models discussed herein may predict per person future expense both to the managed care industry and the individual by including at least out of pocket expenses. The risk functions in other approaches do not factor in the patient perspective by including out of pocket expense. Further, they estimate annual costs only, unlike the methods discussed herein that estimate lifetime costs. Unlike models in other approaches that predict the likelihood of being a high user of services, the high user more likely being an individual with a disease, the methods discussed herein predict the per person expense for individuals with no disease conditions and thereby not a high user of health care services (e.g., using the steps illustrated in block 401 through block 604).

The exemplary embodiments offer a methods of providing incentives to health insurance recipients to achieve desirable health outcomes, comprising (a) providing financial rebates as a percentage of paid premiums on meeting qualifying criteria on an annual basis, (b) establishing achievement of a healthy body mass index for the annual period as a qualifying criteria, (c) establishing a healthcare individual reimbursement account for the recipients, (d) receiving contributions, from a health insurance provider, to the healthcare individual reimbursement account, said contributions being structured as an annuity calculated as a percentage of paid premiums, (e) managing of the reimbursement funds by the recipients for healthcare associated expenditures, and (f) matching annual contributions to the recipients healthcare individual reimbursement account by an employer based wellness program.

Example Implementations of Predictive Analytics

Figure 9A:
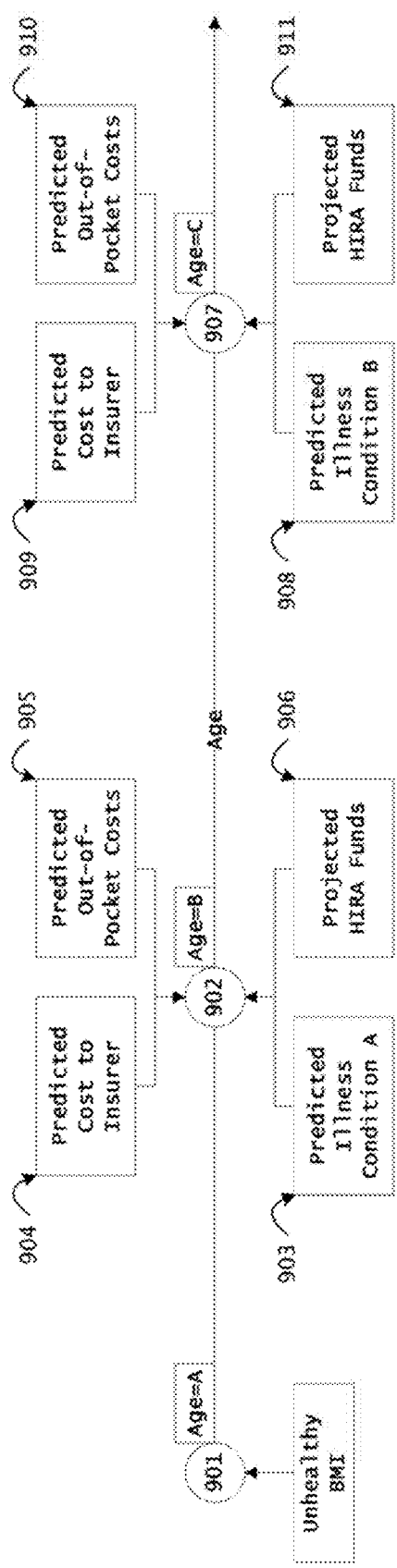
FIG. 9A is a graphical representation illustrating a method for providing differential analysis of predicted lifetime costs and predicted cost reductions for an individual with unhealthy BMI in accordance with various exemplary embodiments of the disclosed system.

FIG. 9A is a graphical illustration of the approach to estimate lifetime out-of-pocket expenses to an individual with an unhealthy BMI, and associated direct costs to the insurer.

Referring to FIG. 9A, at block 901 the current bio-markers for the individual with an unhealthy BMI (e.g., based on a body mass indicator included in associated healthcare data stored in the memory 150) are established at age A. At block 902, an illness condition A (903) may be predicted for the individual at an age B based on available healthcare data. At block 904, the direct cost to the insurer may be predicted using the methods and systems discussed herein, such as the models discussed above, as performed by the microprocessor 160. At block 905, the out-of-pocket expenses for illness condition A may be predicted. At block 906, availability of funds in the HIRA account for the individual based on past BMI history may be projected. Continuing over age, at blocks 907 through 911, other illness conditions may be predicted along with associated out-of-pocket costs to the individual, direct costs to the insurer, and projected availability of HIRA funds.

Figure 9B:
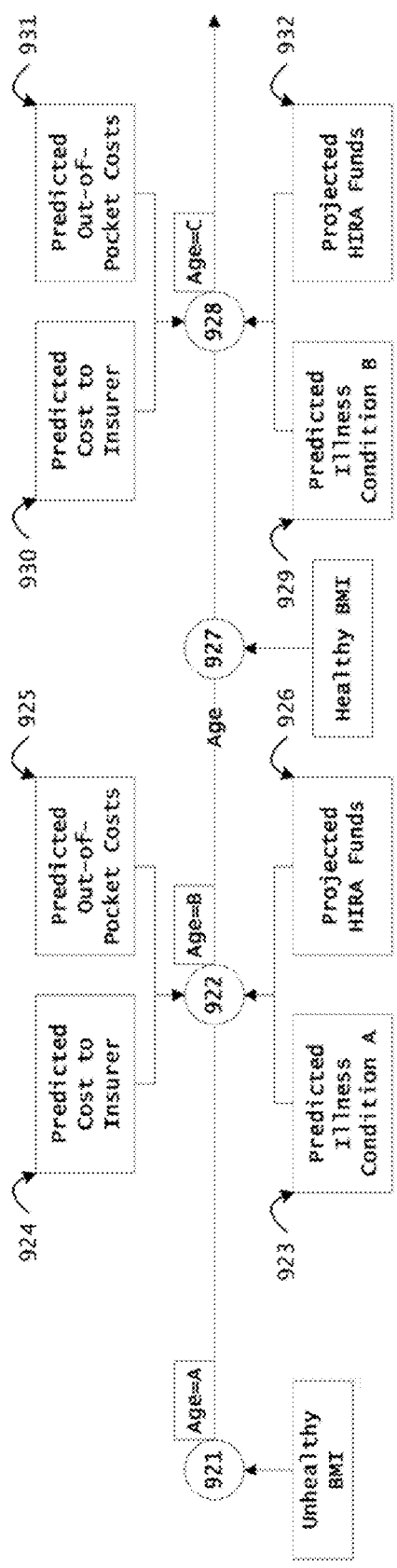
FIG. 9B is a graphical representation illustrating a method for providing differential analysis of predicted lifetime costs and predicted cost reductions for an individual with unhealthy BMI on achieving a healthy BMI in accordance with various exemplary embodiments of the disclosed system.

Referring to FIG. 9B, the estimations may be performed to include the individual with an unhealthy BMI at block 921 achieving a healthy BMI at block 927. This may be of particular relevance to any financial incentives provided by the insurer. For instance, an insurer may provide incentives to the individual due to achieving a healthier BMI or other body mass indicator as a result of decreased expected costs, as determined using the methods and systems discussed herein. For example, if a drop in weight (e.g., and equivalent BMI) by the individual leads to a predicted $15,000 decrease in cost to the insurer, the insurer may provide the individual with a proportional incentive, to encourage the drop in weight.

Figure 9C:
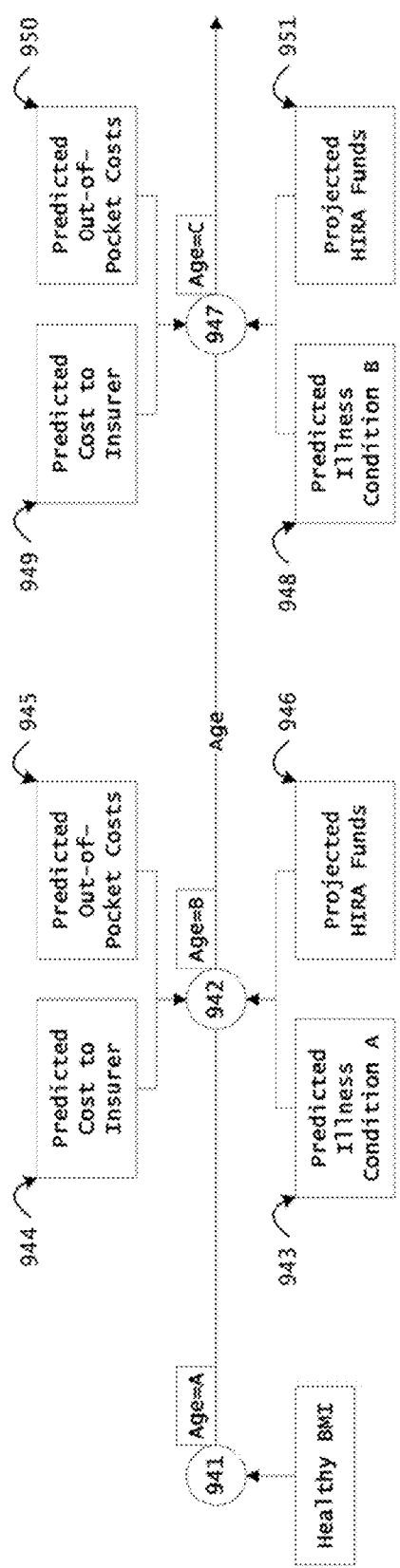
FIG. 9C is a graphical representation illustrating a method for providing differential analysis of predicted lifetime costs and predicted cost reductions for an individual with healthy BMI in accordance with various exemplary embodiments of the disclosed system.

Referring to FIG. 9C, the estimates may be performed to include the individual with a healthy BMI at block 941. This is a novel provision to reward healthy individuals rather than provide cross-subsidization that places healthy individuals at a disadvantage. Healthy individuals may also benefit from financial incentives in the HIRA plan.

Referring to FIG. 10, an iterative algorithm is described for a list of illness conditions. The algorithm may be stored in the memory 150 and executed by the microprocessor 160 of the predictive analytics system 190. For each illness condition in block 1002, personalized bio-markers and dependent and independent variables may be factored by illness condition. At block 1004, a probability may be established by bio-markers associated with the illness condition. At block 1005, a weight may be established by dependent variables associated with the illness condition. At block 1006, a weight may be established by independent variables associated with the illness condition. At block 1007, the likelihood of the illness condition in the individual may be determined based on the said probability and weights. At block 1008, the onset of the likely illness may be estimated. At block 1009, the duration of treatment for the illness condition may be estimated. At block 1010, the annual cost of treatment for the illness condition, including out-of-pocket expenses and insurer direct payments, using the two step regression model with healthy and unhealthy BMI discussed above, may be estimated. At block 1011, the iteration may continue for the next illness condition. Once the end of the list is reached, the algorithm may terminate at block 1012.

Referring to FIG. 11, a graphical representation is described to illustrate the two-part model and the final model for the estimation of personalized lifetime expenses, including out of pocket costs for diseases related to unhealthy BMI (1101). At block 1102, the first part of the two-part model discussed herein may be applied, with continuous dependent variables (1103) and independent variables (1104). Then at block 1105, the second part of the two-part model may be applied, with binary dependent variables (1106) and independent variables (1104). At block 1107, the final part of the model may be applied to interact the indicators of illnesses from the first and second parts of the model for predictions on expenditures for an individual of interest based on at least the age, race, gender, ethnicity, education, income, family history, activities of daily living, BMI, and any other suitable individual characteristics. At block 1109, the final part of the regression model is described that can be used to estimate personalized lifetime expenditures for an individual of interest.

Referring to FIG. 12, in an exemplary embodiment, the estimation of total lifetime expenditures for an individual may be performed incrementally across categorized age groups beginning at the current age and over the lifespan. Block 1202 represents the measured BMI, and block 1203 represents the current age, of the individual. Block 1204 illustrates one exemplary categorization by age group, categorized in, but not limited to, increments of 10. Block 1205 illustrates the onset of illness conditions ($I_1, I_2, \ldots, I_n$) and an associated duration for the illness estimated from the sub population in the category. Multiple other illnesses, by onset and duration, are illustrated based on the sub population in the category. The incremental estimation over the lifespan traverses through subsequent age groups where the centered age may be set to the onset of an illness condition in the age group category. The estimation may be repeated iteratively for other illnesses. The onset of an illness may be in an earlier, current or later age group (i.e. range), and the duration of an illness may span across age groups. Where the onset and duration of an illness does not span through an age group over the lifespan, associated illness related expenses are excluded from the estimation of future expenditures.

Referring to FIG. 13, the estimation of the probability of an illness 1306 for an individual may be performed incrementally across categorized age groups beginning at the current age and over the lifespan. Block 1302 represents the measured BMI, and block 1303 represents the current age, of the individual. Block 1304 illustrates one exemplary categorization by age group, categorized in, but not limited to, increments of 10. Block 1305 illustrates the probability of illness conditions $P(I_1, I_2, \ldots, I_n)$ for the individual estimated from the sub population in the category. The probability of multiple other illnesses are illustrated based on the sub population in the category. The incremental estimation over the lifespan traverses through subsequent age groups where the centered age may be set to the onset of an illness condition in the age group category. The estimation may be repeated iteratively for other illnesses. The onset of an illness may be in an earlier, current or later age group (i.e. range), and the duration of an illness may span across age groups. Where the onset and duration of an illness does not span through an age group over the lifespan, associated illness probabilities are excluded from the estimation of future expenditures.

Referring to FIG. 14, this figure illustrates a similarity function based on BMI. At block 1401 the centered BMI is set as the pivot to obtain the coefficient of centered BMI by subtracting the BMI of each of the other individuals categorized by age group in blocks 1404 and 1405 from the pivot. The individuals in the cohort (sample set) are categorized by age group 1406 and BMI 1403 (x-axis). The y-axis denotes the expense for an illness ($I_n$) 1402 for each individual.

Referring to FIG. 15, this figure illustrates a similarity function based on age. At block 1501 the centered age is set as the pivot to obtain the coefficient of centered age by subtracting the age of each of the other individuals categorized by BMI group in blocks 1504 and 1505 from the pivot. The individuals in the cohort (sample set) are categorized by BMI group 1506 and age 1503 (x-axis). The y-axis denotes the expense for an illness ($I_n$) 1502 for each individual.

Referring to FIG. 16, this figure illustrates a flowchart for real time data aggregation as a precursor to regression analysis to estimate total lifetime expenditures for an individual. At block 1602, query 1608 is received by a data harvester to retrieve healthcare datasets. At block 1603, connectors to a plurality of data providers 1604 retrieve the requested healthcare datasets from the healthcare marketplace, health insurers (public and private), and national or international healthcare organizations for population and illness related datasets. At block 1610, the retrieved raw and disparate healthcare datasets are received for data aggregation 1606. The retrieved healthcare datasets are processed by the data aggregator 1606 to create processed healthcare datasets. The processed healthcare datasets are generated by mining data from a plurality of data exchange formats in the most recent healthcare datasets, recoding data in the most recent healthcare datasets for normalization and consideration of missing values in categories of data, and imputing data in order to account for missing values in the most recent healthcare datasets. At block 1611, a series of data parsing and fusion operations 1612 are initiated for data mining, recoding and imputing to normalize and generate missing values. At block 1616, aggregate health profiles (AHP) 1614 are generated and received for analysis 1618 by the two-part regression model 1620. At block 1621, the two-part model uses interactions and variables (dependent and independent) 1622 to generate indicators for illnesses that include at least coefficients, expenses and probabilities for the illnesses. At block 1624, the indicators for illnesses 1626 are received by the final part of the regression model. At block 1627, the final part of the model uses interactions and variables 1628 to estimate total lifetime expenses and a healthcare risk score 1630 for an individual of interest.

Referring to FIG. 17, multiple imputation may be performed using any statistical analysis and statistical software framework (e.g. STATA, SPSS) to process a corpus of population sample datasets. At block 1702, use of methods such as linear regression and predictive mean matching may be applied to generate (create) missing variables and/or recode information in variables 1703.

Referring to FIG. 18, in the first part of the regression model, block 1802 performs linear regression to calculate an expense for an illness, using for example Taylor series for variance control strategies, and commands supported by the statistical analysis and statistical software framework. The regression produces coefficients 1803 for the illness. The first part of the regression model may be applied iteratively to a plurality of illnesses. A generalized command syntax for the linear regression may be described as (using STATA as the reference framework):
a) Direct Payments by Public Insurer
svy linearized, subpop(if nl_pub !=.): regress (dependent variables) (independent variables)
b) Direct Payments by Private Insurer
svy linearized, subpop(if nl_prv !=.): regress (dependent variables) (independent variables)
c) Out of Pocket Expenses by Individual
svy linearized, subpop(if nl_oop !=.): regress (dependent variables) (independent variables)
a) Referring to FIG. 19, in the second part of the regression model, block 1902 performs logistic regression to calculate a probability of an illness related expense using, for example, commands supported by the statistical analysis and statistical software framework. The regression produces coefficients 1903 for the illness. The second part may be applied iteratively to a plurality of illnesses. A generalized command syntax for the logistic regression may be described as (using STATA as the reference framework):
Direct Payments by Public Insurer
  svy linearized: logit if_pub (dependent variables) (independent variables)
b) Direct Payments by Private Insurer
  svy linearized: logit if_prv (dependent variable) (independent variable)
c) Out of Pocket Expenses by Individual
  svy linearized: logit if_oop (dependent variables) (independent variables)

Referring to FIG. 20, this figure illustrates the indicators for an illness (stroke) generated by the two-part regression model for a specific unhealthy BMI (BMI=30). At block 2002, the computed variables are listed. At block 2003, the coefficients for the illness and for the specific unhealthy BMI are listed. At block 2005, the illness related expense estimated by the first part of the two-part model for a specific unhealthy BMI (BMI=30) is listed by age group 2004. At block 2006, the probability of illness related expense estimated by the second part of the two-part model for a specific unhealthy BMI (BMI=30) is listed by age group 2004. At block 2007, the expense for a specific unhealthy BMI (BMI=30) in the age group 2004 is predicted by multiplying the expense in block 2005 with the probability in block 2006 for the age group 2004. At block 2008, the total expense for the illness for a specific unhealthy BMI (BMI=30) in the age group 2004 is listed. At block 2010, the total expense for the illness at block 2008 is multiplied by the antilog of the mean of residuals at block 2009. Block 2011 illustrates the indicators for the illness generated by the two-part regression model for a specific healthy BMI (BMI=22). At block 2012, the total expense for the illness with the specific healthy BMI (BMI=22) in the age group 2004 is listed. At block 2013, the total expense for the illness at block 2012 is multiplied by the antilog of the mean of residuals at block 2009. At block 2015, the cost reduction (or variance) 2014 is calculated as the difference between the expenses at blocks 2010 and 2013 to illustrate cost reduction based on achieving a healthy BMI (BMI=22).

Referring to FIG. 21, this figure illustrates the expenditure values (absolute and relative) computed by the two-part regression model for a specific age, at healthy and an unhealthy BMI, with and without the illness condition at the specific current age. In certain exemplary embodiments, the expenditure values may be estimated based on centered age and/or BMI across a population dataset. In certain exemplary embodiments, the expenditure values may be estimated based on age and/or BMI clustering (categorization by group) across a subset of the population dataset.

Referring to FIG. 22, this table provides examples of interactions coded in the regression model, using STATA as the reference framework. Additional interactions may be coded to enhance the model.

Referring to FIG. 23, this table provides examples of variables coded in the regression model, using STATA as the reference framework. Additional variables may be generated and registered to enhance the model.

Referring to FIG. 24, this table provides examples of variables imported in the regression model from datasets received from data providers 1604. Additional variables may be imported and registered as required to enhance the model. For example, CSV and TSV format datasets, the first record may be a header, which contains column names in each of the fields for parsers to identify each field in the data record. XML format datasets provide field names in tags for parsers to identify each field in the XML element. JSON format datasets provide a field name in the name/value pair for parsers to identify each field in the JSON object.

Referring to FIG. 25, in an exemplary embodiment, a web server platform 2502 comprises of the self-service web portal 2507, the analytics system 2503 that includes at least the regression models 2505 and data aggregator 2506. The analytics system 2503 receives requests from the self-service web portal 2507 to estimate lifetime expenditures for an individual or group of individuals from user devices 2514 or user terminals 2522. At block 2504, web reports may be scheduled and dispatched to the requestor, as an email attachment, or web link embedded in an email message, or to a reports server. The reports may be an expenses forecast 2534 for an individual 2512, or a payouts forecast 2532 for a plurality of members to a healthcare insurance provider 2508. The web server 2502 may be, for example, a dedicated physical server, a virtualized server on a hypervisor, cloud platform, etc.

In an exemplary embodiment, the data aggregator 2506 sends directed queries to a plurality of data providers 2508 (e.g. health insurance providers, healthcare data exchanges, healthcare organizations, etc.) and receives member healthcare datasets 2510. The datasets are processed to generate aggregate health profiles for regression 2505 and estimation of lifetime expenditures (e.g., lifetime healthcare expenditures) for an individual or a group of individuals as per estimate requests 2516, 2524, and 2530.

At block 2516, an individual 2512 may request an estimate of the lifetime expenditure from a user device 2514 (such as a smartphone, table, laptop/computer, etc.). At block 2518, an individual 2512 during a wellness visit to a primary care physician 2520 may request an estimate of the lifetime expenditure 2524 from a user terminal 2522 provided at the facility. At block 2526, an individual 2512 during a hospital discharge may request an estimate of the lifetime expenditure 2530 from a user terminal 2522 provided at the hospital 2528.

At block 2536, a health insurance provider 2508 may offer financial incentives 2536 to health insurance beneficiaries 2512 for achieving a healthy BMI. In an exemplary embodiment, the healthcare risk score is determined based on the estimated total lifetime healthcare expenditures for the individual of interest. In an exemplary embodiment, the method includes displaying, on a display device (e.g. computer monitor, LCD screen, CRT, etc.), the estimated total lifetime healthcare expenditures for the individual of interest and the healthcare risk score for the individual of interest.

The model estimates average per individual increase in predicted expenditure among individuals with healthy and unhealthy BMI and calculates cost reduction as the cost differential wherein individuals with unhealthy BMI achieve healthy BMI. BMI and variables have been categorized rather than applying them purely as continuous variables. The RAND two part model has been modified to estimate expenditures among individuals with healthy and unhealthy BMI for each illness condition associated with BMI. The weights are determined by the frequency of healthy and unhealthy BMI individuals associated with the illness condition in the appropriate age group for granular estimation of illness attributed expenditures. Improvement in activities of daily living are factored in as an indirect benefit where individuals with unhealthy BMI achieve healthy BMI.

The exemplary embodiments overcome the limitations of other approaches wherein these other approaches (a) estimate lifetime costs using cross sectional regression analysis; (b) model expenditures using a generalized linear model with a variance function; (c) determine the incremental cost between individuals with and without the disease; (d) control specific variables in the calculus; and (e) use a lifetable to simulate the distribution of lifetime costs.

The exemplary embodiments overcome the limitations of other approaches by (a) using a combination of linear and logistic regression; (b) factoring in the interaction of the diseases with BMI; (c) estimating the cost difference between individuals with healthy and unhealthy BMI pivoted on the disease; and (d) applying personalized variables that are distinct between individuals.

FIG. 26 illustrates an exemplary method for determining lifetime healthcare expenditures for an individual, on-demand and in real-time, based on body mass index on a computing system. The computing system can include, for example, the data harvester 1602, the data aggregator 1606, aggregate health profiles 1614, the two-part regression model 1620, and the final part regression model 1624 (See FIG. 16). In step 2601 of the method, a request is received for an estimate of the lifetime healthcare expenditures for an individual of interest. The request can be sent from a computing device (e.g., computer, laptop, tablet, smartphone, etc.) that is separate from the computing system that performs the method. At step 2603, the method can include querying, by the data aggregator 1606, in real-time, the most recent healthcare datasets for a plurality of individuals, including the individual of interest, from the data harvester 1602.

At step 2605, the method can include retrieving, by the data harvester 1602, in real-time, using a plurality of data source specific connectors, the most recent healthcare datasets from a plurality of healthcare data providers 1604. Each healthcare dataset includes, for example, at least the body mass index, the age, and the personal health record associated with an individual. In an exemplary embodiment, the plurality of individuals includes a first subset of individuals associated with an illness condition and a second subset of individuals not associated with the illness condition.

At step 2607, the method can include receiving, by the data aggregator 1606, the plurality of the most recent healthcare datasets for the plurality of individuals. At step 2609, the method can include generating, by the data aggregator 1606, processed healthcare datasets by mining data from a plurality of data exchange formats in the plurality of the most recent healthcare datasets, recoding data in the plurality of the most recent healthcare datasets for normalization and consideration of missing values in categories of data, and imputing data in order to account for missing values in the plurality of the most recent healthcare datasets.

At step 2611, the method can include generating, by the data aggregator 1606, aggregate health profiles 1614 for the plurality of individuals from the processed healthcare datasets. In an exemplary embodiment, the aggregate health profile 1614 can include, for example, attributes from at least the medical health records, personal profile, medical history, and claims history of the individual.

At step 2613, the method can include receiving, by a two-part regression model 1620 of the computing system, the aggregate health profiles 1614, a first set of variables related to characteristics of the individual of interest, and interactions that are expressed as a second set of variables and represent a quantitative contextual and evidence based correlation between illnesses, treatments, the onset and duration of illness, and attributes in the individual's aggregate health profile.

At step 2615, the method can include generating, by the two-part regression model 1620 of the computing system, indicators for an illness. In an exemplary embodiment, the indicators include, for example, expenses for the illness, probability of the illness, coefficients for the illness, etc.

At step 2617, the method can include receiving, by the final part regression model 1624 of the computing system, the indicators for the illness, the interactions, and the first set of variables.

At step 2619, the method can include estimating, by the final part regression model 1624 of the computing system, the total lifetime healthcare expenditures for the individual of interest and a healthcare risk score for the individual of interest based on the indicators for the illness, the interactions, and the first set of variables.

The generation (creation) of variables that express interactions, dependent variables, independent variables, and command syntax (STATA) to execute the regression model using the variables are illustrated below as representative examples.

1) Creating Dummy Variables for Healthy Weight
   generate hlthwt=bmi_c>=18.6 & bmi_c<=24.9 if bmi_c !=.
   generate ovob=bmi_c>=25 if bmi_c !=.
   generate undwt=bmi_c<=18.5 if bmi_c !=.
2) Creating Dummy Variables for Type of Arthritis
   generate rh_arth=arthtpdx==1 if arthtpdx !=.
   generate os_arth=arthtpdx==2 if arthtpdx !=.
   generate unsp_arth=arthtpdx==3 if arthtpdx !=.
3) Interaction between Osteoarthritis and Overweight/Obese (OvOb)
   generate OsOb=os_arth*OvOb if OvOb !=.
4) Interaction between Osteoarthritis and Healthy Weight
   generate HlthOs=os_arth*hlthwt if hlthwt !=.
5) Computing Duration of Arthritis
   generate arthdur=agelast−arthaged if arthaged>=0
   mvencode arthdur if arthaged==−1, mv(.=−1)
   generate arthdursq=arthdur*arthdur if arthdur !=.
6) Computing Ethnicity and Gender Categories
   generate nonhis=hispanx==2
   generate male=sex==1
7) Interaction between Recoded Diabetes and Centered Age
   generate dbagecen=diab_rec*agecen
   generate dbagesq=diab_rec*agesq
8) Computing Natural Log of Out of Pocket
   generate nl_oop=n(OOP_all)
9) Generating Recoded Variables for Cancer
   generate cacx_rec=cacervix==1 if cacervix !=−1
   recode cacx_rec (.=−1) if cacervix==−1 generate cabone_rec=cabone==1 if cabone==1
recode cabone_rec (.=−1) if cabone==−1
generate cacx_rec=cacervix==1 if cacervix !=−1
recode cacx_rec (.=−1) if cacervix==−1
generate cabone_rec=cabone==1 if cabone==1
recode cabone_rec (.=−1) if cabone==−1
generate caliver_rec=caliver==1 if caliver !=−1
recode caliver_rec (.=−1) if caliver==−1
generate calung_rec=calung==1 if calung !=−1
recode calung_rec (.=−1) if calung==−1
generate calymp_rec=calymph==1 if calymph !=−1
recode calymp_rec (.=−1) if calymph==−1
generate cabrain_rec=cabrain==1 if cabrain !=−1
recode cabrain_rec (.=−1) if cabrain==−1
10) Computing Natural Log of Medicare Expenditures
generate nl_mcr=ln(mcr) if mcr !=0
11) Regression of Medicare Expenditures with Associated Independent Variables
svy linearized, subpop(if nl_mcr !=.): regress nl_mcr os_arth Age_25_34 Age_35_44 Age_45_54 Age_55_64 Age_65_74 Age_75_85 OvOb rh_arth arthclrec
12) Logistic Model to Predict Probability of Medicare Expenditures
svy linearized: logit if_mcr Age_25_34 Age_35_44 Age_45_54 Age_55_64 Age_65_74 Age_75_85 OvOb undwt os_arth rh_arth arthclred arthclrecsq
13) Interaction between Age and Arthritis
generate Age25Os:InterAge25OsArth=Age_25_34*os_arth if os_arth !=.
generate Age35Os:InterAge35Os=Age_35_44*os_arth if os_arth !=.
generate age45Os:InterAge45Os=Age_45_54*os_arth if os_arth !=.
generate Age55Os:InterAge55Os=Age_55_64*os_arth if os_arth !=.
generate Age65Os:InterAge65Os=Age_65_74*os_arth if os_arth !=.
generate Age75Os:InterAge75Os=Age_75_85*os_arth if os_arth !=.
14) Private Expenditure Category
generate nl_prv=ln(prvexp)
generate if_prv=prvexp>0
generate prv_exp=iptprv10+rxprv10+hhaprv10+hhnprv10+zidprv10+zifprv10+ertprv10+optprv10+ob vprv10+amnprv10+obcprv10+obnprv10+obeprv10+opvprv10+opsprv10+amcprv10+ameprv10+amaprv10+amtprv10+dvtprv10
15) Public Expenditure Category
generate pub_exp=iptmcr10+rxmcr10+hhamcr10+hhnmcr10+zidmcr10+zifmcr10+ertmcr10+optmcr10+obvmcr10+amnmcr10+iptmcd10+rxmcd10+hhamcd10+hhnmcd10+zidmcd10+zifmcd10+ertmcd10+optmcd10+obvmcd10+amnmcd10+obcmcr10+obcmcd10+obnmcr10+obnmcd10+obemcr10+obemcd10+obamcr10+obamcd10+op vmcr10+opvmcd10+opsmcr10+opsmcd10+amcmcr10+amcmcd10+amemcr10+amemcd10+amamcr10+amamcd10+amtpry10+dvtmcr10+dvtmcd10+othmcr10+othmcd10
16) Out of Pocket Expenditure Category
generate OOP_all=optsf10+obvslf10+obcslf10+obnslf10+obeslf10+obaslf10+opvslf10+opsslf10+amnslf10+amcslf10+ameslf10+amaslf10+amtslf10+ertslf10+zifslf10+zidslf10+iptslf10+hhaslf10+hhnslf10+rxslf10+dvtslf10+othslf10
generate nl_pub=ln(pub_exp)
generate if_pub=pub_exp>0
17) Age Categories
generate age_18_24=agelast>=18 & agelast<=24
generate age_25_34=agelast>=25 & agelast<=34
generate age_35_44=agelast>=35 & agelast<=44
generate age_45_54=agelast>=45 & agelast<=54
generate age_55_64=agelast>=55 & agelast<=64
generate age_65_74=agelast>=65 & agelast<=74
generate age_75_85=agelast>=75 & agelast<=85
18) Arthritis (Private Expenditure)
svy linearized, subpop(if nl_prv!=.): regress nl_prv hlthwt age_75_85 age_65_74 age_55_64 age_45_54 age_35_44 age_25_34 os_arth rh_arth unsp_arth arthdur
svy linearized, subpop(if nl_prv!=.): regress nl_prv ovob age_75_85 age_65_74 age_55_64 age_45_54 age_35_44 age_25_34 unsp_arth os_arth rh_arth arthdur
svy linearized: logit if_prv age_25_34 age_35_44 age_45_54 age_55_64 age_75_85 hlthwt age_65_74 os_arth ovob rh_arth unsp_arth arthob female nvrmd div wid Educ_HS Educ_Col midinc
19) Diabetes (Duration)
generate dbcldur=agelast−diabaged if diabaged>=0
mvencode dbcldur if diabaged==−1, mv(.=−1)
generate dbcldursq=dbcldur*dbcldur if dbcldur !=.
20) Diabetes (Private Expenditure)
svy linearized, subpop(if nl_prv!=.): regress nl_prv diab_rec age_25_34 age_35_44 age_45_54 age_55_64 age_75_85 age_65_74 ovob dbcldur dbcldursq db2534 db3544 db6574 female
svy linearized, subpop(if nl_prv!=.): regress nl_prv diab_rec age_25_34 age_35_44 age_45_54 age_55_64 age_75_85 age_65_74 hlthwt dbcldur dbcldursq db2534 db3544 db6574 female
svy linearized: logit if_prv age_25_34 age_35_44 age_45_54 age_55_64 age_75_85 ovob age_65_74 dbcldur hlthwt diab_rec
21) Coronary Heart Disease (Private Expenditure)
generate chddur=agelast−chdaged if chdaged>=0
mvencode chddur if chdaged==−1, mv(.=−1)
generate chddursq=chddur*chddur if chddur !=.
svy linearized, subpop(if nl_prv !=.): regress nl_pry chddur age_65_74 age_75_85 age_55_64 age_45_54 age_35_44 age_25_34 chd_rec chddursq ovob
svy linearized: logit if_prv age_65_74 age_55_64 age_45_54 ovob chd_rec chddur chddursq age_75_85 hlthwt age_35_44 Educ_Col Educ_HS age_25_34 female
svy linearized, subpop(if nl_prv !=.): regress nl_prv chddur age_65_74 age_75_85 age_55_64 age_45_54 age_35_44 age_25_34 chd_rec hlthwt chddursq
22) High Blood Pressure (Private Expenditure)
generate hbcldur=agelast−hibpaged if hibpaged>=0
mvencode hbcldur if hibpaged==−1, mv(.=−1)
generate hbcldursq=hbcldur*hbcldur if hbcldur !=.
svy linearized, subpop(if nl_prv!=.): regress nl_prv age_25_34 age_35_44 age_45_54 age_55_64 age_75_85 age_65_74 ovob hbcldur hbcldursq hbp_rec
svy linearized, subpop(if nl_prv!=.): regress nl_prv age_25_34 age_35_44 age_45_54 age_55_64 age_75_85 age_65_74 hlthwt hbcldur hbcldursq hbp_rec svy linearized: logit if_prv age_25_34 age_35_44 age_45_54 age_55_64 age_75_85 age_65_74 ovob hbp_rec hlthwt hbob hbhlth hbcldur 23) Myocardial Infarction (Private Expenditure)
generate midur=agelast-miaged if imaged>=0
mvencode midur if miaged==-1, mv(.=-1)
generate midursq=midur*midur if midur !=.
 svy linearized, subpop(if nl_prv!=.): regress nl_prv age_25_34 age_35_44 age_45_54 age_55_64 age_75_85 age_65_74 ovob mi_rec miageinter6574 mi5564
 svy linearized: logit if_prv age_25_34 age_45_54 age_55_64 age_75_85 age_65_74 mi_rec ovob midur midursq hlthwt age_35_44 mi7585
 svy linearized, subpop(if nl_prv!=.): regress nl_prv age_25_34 age_35_44 age_45_54 age_55_64 age_75_85 age_65_74 hlthwt mi_rec miageinter6574 mi5564

24) Mental Health (Private Expenditure)
 svy linearized, subpop(if nl_prv!=.): regress nl_prv ment_pf age_65_74 age_75_85 age_55_64 age_45_54 age_35_44 age_25_34 hlthwt
 svy linearized, subpop(if nl_prv!=.): regress nl_prv ment_pf age_65_74 age_75_85 age_55_64 age_45_54 age_35_44 age_25_34 ovob
 svy linearized: logit if_prv ment_pf age_65_74 age_75_85 age_55_64 age_45_54 age_35_44 age_25_34 ovob nvrmd Educ_HS lowPr female white Educ_Col highinc midinc region10
 svy linearized: logit if_prv ment_pf age_65_74 age_75_85 age_55_64 age_45_54 age_35_44 age_25_34 hlthwt nvrmd Educ_HS lowPr female white Educ_Col highinc midinc region10

25) Breast Cancer (Private Expenditure)
generate brst_rec=cabreast==1 if cabreast>0
generate brstdur=agelast-brstaged if brstaged>=0
mvencode brstdur if brstaged==-1, mv(.=-1)
generate brstdursq=brstdur*brstdur if brstdur !=.
generate brst3544=brstdur*brstdursq*age_35_44 if brstdur!=.
generate brst7585=brstdur*brstdursq*age_75_85 if brstdur!=.
generate brst6574=brstdur*brstdursq*age_65_74 if brstdur!=.
generate brst5564=brstdur*brstdursq*age_55_64 if brstdur!=.
generate brst4554=brstdur*brstdursq*age_45_54 if brstdur!=.
generate brst1824=brstdur*brstdursq*age_18_24 if brstdur!=.
 svy linearized, subpop(if nl_prv!=.): regress nl_prv brst3544 ovob brst_rec brstdur brstdursq
 svy linearized, subpop(if nl_prv!=.): regress nl_prv brst3544 hlthwt brst_rec brstdur
 svy linearized: logit if_prv brst3544 brst_rec ovob age_35_44 brstdur brstdursq
 svy linearized: logit if_prv brst3544 brst_rec hlthwt age_35_44 brstdur brstdursq
 svy linearized, subpop(if nl_prv!=.): regress nl_prv brst4554 ovob brst_rec brstdur brstdursq age_45_54
 svy linearized, subpop(if nl_prv!=.): regress nl_prv brst4554 hlthwt brst_rec brstdur age_45_54
 svy linearized: logit if_prv brst4554 brst_rec ovob age_45_54 brstdur brstdursq
 svy linearized: logit if_prv Brst4554 brst_rec hlthwt age_45_54 brstdursq svy linearized, subpop(if nl_prv!=.): regress nl_prv ovob brst_rec brstdur age_55_64
 svy linearized, subpop(if nl_prv!=.): regress nl_prv hlthwt brst_rec brstdur undwt age_55_64
 svy linearized: logit if_prv brst_rec ovob brst5564 age_55_64 brstdur
 svy linearized: logit if_prv brst_rec hlthwt undwt brst5564 age_55_64 brstdur
 svy linearized, subpop(if nl_prv!=.): regress nl_pry brst6574 brstdur brst_rec ovob
 svy linearized, subpop(if nl_prv!=.): regress nl_pry brst6574 brst_rec hlthwt undwt
 svy linearized: logit if_prv brst_rec ovob brst6574 age_65_74 brstdursq
 svy linearized: logit if_prv brst_rec hlthwt brst6574 age_65_74 brstdursq
 svy linearized: logit if_prv brst_rec ovob brst7585 age_75_85 brstdur
 svy linearized: logit if_prv brst_rec hlthwt brst7585 age_75_85 brstdur
 svy linearized, subpop(if nl_prv!=.): regress nl_pry brst_rec ovob brstdur brst7585 age_75_85
 svy linearized, subpop(if nl_prv!=.): regress nl_pry brst_rec hlthwt brstdur brst7585 age_75_85

26) Cholesterol (Private Expenditure)
 svy linearized, subpop(if nl_prv!=.): regress nl_prv age_65_74 age_75_85 age_55_64 age_45_54 age_35_44 age_25_34 choldur chol_rec cholob chol3544
 svy linearized, subpop(if nl_prv!=.): regress nl_prv age_65_74 age_75_85 age_55_64 age_45_54 age_35_44 age_25_34 choldur chol_rec cholhlth chol3544
 svy linearized: logit if_prv hlthwt age_65_74 age_55_64 age_45_54 age_35_44 age_25_34 chol_rec cholhlth
 svy linearized: logit if_prv chol_rec age_25_34 age_45_54 age_35_44 age_55_64 age_65_74 ovob cholob 27) High Blood Pressure (Public Expenditure)
 svy linearized, subpop(if nl_pub!=.): regress nl_pub hbp_rec hbcldur hbcldursq age_25_34 age_35_44 age_45_54 age_55_64 age_75_85 age_65_74 hb2534 ovob undwt hb5564 hbob
 svy linearized, subpop(if nl_pub!=.): regress nl_pub hbp_rec hbcldur hbcldursq age_25_34 age_35_44 age_45_54 age_55_64 age_75_85 age_65_74 hlthwt hb2534 hb5564
 svy linearized: logit if_pub nvrmd hisp age_65_74 age_75_85 age_55_64 age_45_54 age_35_44 age_25_34 ovob hbp_rec hbcldur hb6574 hb7585
 svy linearized: logit if_pub age_65_74 age_75_85 age_55_64 age_25_34 hlthwt hbp_rec hbcldur hb5564 hb6574 hb7585

28) Coronary Heart Disease (Public Expenditure)
 svy linearized, subpop(if nl_pub !=.): regress nl_pub age_35_44 age_45_54 age_55_64 age_75_85 age_65_74 ovob chd_rec chd7585
 svy linearized: logit if_pub age_25_34 age_45_54 age_55_64 age_75_85 age_65_74 ovob chd_rec chddur chddursq
 svy linearized: logit if_pub age_25_34 age_45_54 age_55_64 age_75_85 age_65_74 hlthwt chd_rec chddur chddursq chd7585

29) Myocardial Infarction (Public Expenditure)
   svy linearized, subpop(if nl_pub!=.): regress nl_pub age_55_64 age_65_74 age_35_44 age_45_54 age_75_85 ovob midur midursq mi_rec miob mi2534 mi3544
   svy linearized, subpop(if nl_pub!=.): regress nl_pub age_55_64 age_65_74 age_35_44 age_45_54 hlthwt midur midursq mi_rec age_75_85 mi2534 mi3544
   svy linearized: logit if_pub age_25_34 age_45_54 age_55_64 age_75_85 ovob age_65_74 mi_rec
   svy linearized: logit if_pub age_25_34 age_45_54 age_55_64 age_75_85 hlthwt age_65_74 mi_rec
30) Diabetes (Public Expenditure)
   svy linearized, subpop(if nl_pub!=.): regress nl_pub dbcldursq female dbcldur age_65_74 age_75_85 age_55_64 age_45_54 age_35_44 db7585 diab_rec ovob hlthwt db6574
   svy linearized: logit if_pub dbcldur age_25_34 age_45_54 age_55_64 age_75_85 age_65_74 ovob dbcldursq db2534 db3544 db4554 db6574 diab_rec
   svy linearized: logit if_pub dbcldur age_25_34 age_45_54 age_55_64 age_75_85 age_65_74 hlthwt db2534 db3544 db4554 db6574 diab_rec
31) Breast Cancer (Public Expenditure)
   svy linearized, subpop(if nl_pub!=.): regress nl_pub age_65_74 age_75_85 age_55_64 age_45_54 age_35_44 brstdur brstdursq brst_rec ovob
   svy linearized, subpop(if nl_pub!=.): regress nl_pub age_65_74 age_75_85 age_55_64 age_45_54 age_35_44 brst3544 brst4554 brst7585 brstdur brstdursq brst_rec hlthwt nvrmd white
   svy linearized: logit if_pub brst_rec age_65_74 age_75_85 age_55_64 age_45_54 age_25_34 ovob white brstob
   svy linearized: logit if_pub brst_rec age_65_74 age_75_85 age_55_64 age_45_54 age_25_34 hlthwt
   svy linearized: logit if_pub brst_rec age_65_74 age_75_85 age_55_64 age_45_54 age_25_34 age_35_44 hlthwt brst2534 brstage5564 brstage6574 brstage7585
32) Cholesterol (Public Expenditure)
   generate choldur=agelast−cholaged if cholaged>=0
   mvencode choldur if cholaged==−1, mv(.=−1)
   generate choldursq=choldur*choldur if choldur !=.
   svy linearized, subpop(if nl_pub!=.): regress nl_pub age_35_44 age_45_54 age_55_64 age_75_85 age_65_74 chol_rec choldur ovob cholob chol5564 chol7585
   svy linearized, subpop(if nl_pub!=.): regress nl_pub age_55_64 age_75_85 age_65_74 chol_rec choldur hlthwt chol3544 chol4554 chol5564
   svy linearized: logit if_pub age_65_74 age_75_85 age_55_64 age_25_34 age_35_44 age_45_54 ovob choldur chol_rec cholob chol4554 chol6574 female white
   svy linearized: logit if_pub age_65_74 age_75_85 age_55_64 age_25_34 age_35_44 age_45_54 choldur chol_rec cholhlth chol3544 chol5564 female white
33) Mental Health (Public Expenditure)
   svy linearized, subpop(if nl_pub!=.): regress nl_pub ment_pf age_65_74 age_75_85 age_55_64 age_45_54 age_35_44 ovob ment7585
   svy linearized, subpop(if nl_pub!=.): regress nl_pub ment_pf age_65_74 age_75_85 age_55_64 age_45_54 age_35_44 age_25_34 hlthwt ment6574 ment7585
   svy linearized: logit if_pub ment_pf age_65_74 age_75_85 age_55_64 age_45_54 age_35_44 age_25_34 hlthwt ment3544 ment5564 ment6574 ment7585
   svy linearized: logit if_pub ment_pf age_65_74 age_75_85 age_55_64 age_45_54 age_35_44 age_25_34 ovob ment3544 ment5564 ment6574 ment7585
34) Arthritis (Public Expenditure)
   svy linearized, subpop(if nl_pub!=.): regress nl_pub age_35_44 age_45_54 age_55_64 age_75_85 age_65_74 arth_rec arthdur arthob arthdursq arth3544 arth4554 arth5564
   svy linearized, subpop(if nl_pub!=.): regress nl_pub age_35_44 age_45_54 age_55_64 age_75_85 age_65_74 arth_rec arthdur arthhlth arthdursq arth3544 arth4554 arth5564
   svy linearized: logit if_pub arth_rec age_25_34 age_55_64 age_75_85 age_65_74 ovob arthdur arth2534
   svy linearized: logit if_pub arth_rec age_25_34 age_55_64 age_75_85 age_65_74 hlthwt arthdur arth2534
35) High Blood Pressure (Out of Pocket Expenditure)
   generate hbhlth=hbp_rec*hlthwt if hlthwt !=.
   generate hbob=hbp_rec*ovob if ovob !=.
   generate hb1824=hbp_rec*age_18_24 if hbp_rec !=.
   generate hb2534=hbp_rec*age_25_34 if hbp_rec !=.
   generate hb3544=hbp_rec*age_35_44 if hbp_rec !=.
   generate hb4554=hbp_rec*age_45_54 if hbp_rec !=.
   generate hb5564=hbp_rec*age_55_64 if hbp_rec !=.
   generate hb6574=hbp_rec*age_65_74 if hbp_rec !=.
   generate hb7585=hbp_rec*age_75_85 if hbp_rec !=.
   svy linearized, subpop(if nl_oop!=.): regress nl_oop age_25_34 age_35_44 age_45_54 age_55_64 age_75_85 ovob age_65_74 hbcldur hbcldursq hbob hb5564 hb6574
   svy linearized: logit if_oop age_25_34 age_35_44 age_45_54 age_55_64 age_75_85 age_65_74 ovob hbcldur hbp_rec hbob hb2534
   svy linearized, subpop(if_oop if nl_oop!=.): regress nl_oop age_25_34 age_35_44 age_45_54 age_55_64 age_75_85 hlthwt age_65_74 hbcldur hbcldursq hbhlth hb3544
   svy linearized: logit if_oop age_25_34 age_35_44 age_45_54 age_55_64 age_75_85 age_65_74 hlthwt hbcldur hbp_rec hbhlth hb2534 female
36) Diabetes (Out of Pocket Expenditure)
   generate dbhlth=diab_rec*hlthwt if hlthwt !=.
   generate dbob=diab_rec*ovob if ovob !=.
   generate db7585=diab_rec*age_75_85 if diab_rec !=.
   generate db6574=diab_rec*age_65_74 if diab_rec !=.
   generate db5564=diab_rec*age_55_64 if diab_rec !=.
   generate db4554=diab_rec*age_45_54 if diab_rec !=.
   generate db3544=diab_rec*age_35_44 if diab_rec !=.
   generate db2534=diab_rec*age_25_34 if diab_rec !=.
   generate db1824=diab_rec*age_18_24 if diab_rec !=.
   generate dbBMI=diab_rec*bmi_c
   generate dbAgelast=diab_rec*agelast
   generate dbdurdursq=diab_rec*dbcldur*dbcldursq
   svy linearized, subpop(if nl_oop!=.): regress nl_oop age_25_34 age_35_44 age_45_54 age_55_64 age_75_85 ovob age_65_74 diab_rec dbcldur dbob db3544 db7585 svy linearized, subpop(if nl_oop!=.): regress nl_oop age_25_34 age_35_44 age_45_54 age_55_64 age_75_85 hlthwt age_65_74 diab_rec dbcldur dbhlth db3544 db7585 svy linearized: logit if_oop age_25_34 age_35_44 age_45_54 age_55_64 age_75_85 age_65_74 ovob dbcldur dbcldursq diab_rec dbob svy linearized: logit if_oop age_25_34 age_35_44 age_45_54 age_55_64 age_75_85 age_65_74 dbcldur dbcldursq diab_rec dbhlth female 37) Arthritis (Out of Pocket Expenditure)
generate arthob=arth_rec*ovob if ovob !=.
generate arthhlth=arth_rec*hlthwt if hlthwt !=.
generate arth6574=arth_rec*age_65_74 if arth_rec !=.
generate arth7585=arth_rec*age_75_85 if arth_rec !=.
generate arth5564=arth_rec*age_55_64 if arth_rec !=.
generate arth4554=arth_rec*age_45_54 if arth_rec !=.
generate arth3544=arth_rec*age_35_44 if arth_rec !=.
generate arth2534=arth_rec*age_25_34 if arth_rec !=.
generate arth1824=arth_rec*age_18_24 if arth_rec !=.
generate arthdurdursq=arth_rec*arthdur*arthdursq if arth_rec !=.
generate bmicenarth=arth_rec*bmicen if bmicen !=.

svy linearized, subpop(if nl_oop!=.): regress nl_oop age_25_34 age_35_44 age_45_54 age_55_64 age_75_85 ovob age_65_74 os_arth rh_arth unsp_arth arthdur arthdursq arthob hlthwt svy linearized, subpop(if nl_oop!=.): regress nl_oop age_25_34 age_35_44 age_45_54 age_55_64 age_75_85 hlthwt age_65_74 os_arth rh_arth unsp_arth arthdur arthdursq arthhlth ovob svy linearized: logit if_oop age_25_34 age_35_44 age_45_54 age_55_64 age_75_85 age_65_74 arth_rec arthob arthdur svy linearized: logit if_oop age_25_34 age_35_44 age_45_54 age_55_64 age_75_85 age_65_74 hlthwt arth_rec arthhlth arth5564 female white 38) Coronary Heart Disease (Out of Pocket Expenditure)
generate chd1824=chd_rec*age_18_24 if chd_rec !=.
generate chd2534=chd_rec*age_25_34 if chd_rec !=.
generate chd3544=chd_rec*age_35_44 if chd_rec !=.
generate chd4554=chd_rec*age_45_54 if chd_rec !=.
generate chd5564=chd_rec*age_55_64 if chd_rec !=.
generate chd6574=chd_rec*age_65_74 if chd_rec !=.
generate chd7585=chd_rec*age_75_85 if chd_rec !=.
generate chdob=chd_rec*ovob if ovob !=.
generate chdhlth=chd_rec*hlthwt if hlthwt !=.

svy linearized, subpop(if nl_oop!=.): regress nl_oop age_25_34 age_35_44 age_45_54 age_55_64 age_75_85 age_65_74 chdob white chddur chddursq svy linearized, subpop(if nl_oop!=.): regress nl_oop age_25_34 age_35_44 age_45_54 age_55_64 age_75_85 hlthwt age_65_74 chd_rec chddur chddursq female white Educ_Col chd2534 svy linearized: logit if_oop age_25_34 age_35_44 age_45_54 age_55_64 age_75_85 age_65_74 chdob chd5564 chd6574 chd7585 svy linearized: logit if_oop age_25_34 age_35_44 age_45_54 age_55_64 age_75_85 age_65_74 chdhlth chd5564 chd6574 chd7585 chd3544 female svy linearized, subpop(if nl_oop!=.): regress nl_oop chd_rec bmic agecen mi_rec chol_rec chddur chddursq female white nonhis unins chdagesq wid nvrmd sep midinc highinc lowPr Educ_Col Edu_c HS ang_rec 39) Myocardinal Infarction (Out of Pocket Expenditure)
generate mihlth=mi_rec*hlthwt if mi_rec !=.
generate miob=mi_rec*ovob if mi_rec !=.
generate mi7585=mi_rec*age_75_85 if mi_rec !=.
generate mi6574=mi_rec*age_65_74 if mi_rec !=.
generate mi5564=mi_rec*age_55_64 if mi_rec !=.
generate mi4554=mi_rec*age_45_54 if mi_rec !=.
generate mi3544=mi_rec*age_35_44 if mi_rec !=.
generate mi2534=mi_rec*age_25_34 if mi_rec !=.
generate mi1824=mi_rec*age_18_24 if mi_rec !=.
generate miBMI=mi_rec*bmi_c if bmi_c !=.

svy linearized, subpop(if nl_oop!=.): regress nl_oop ovob mi_rec age_25_34 age_35_44 age_45_54 age_55_64 age_65_74 mi7585 svy linearized, subpop(if nl_oop!=.): regress nl_oop hlthwt mi_rec age_25_34 age_35_44 age_45_54 age_55_64 miageinter6574 age_75_85 svy linearized: logit if_oop age_75_85 age_55_64 age_45_54 age_35_44 age_25_34 age_65_74 ovob mi_rec midur female white midursq svy linearized: logit if_oop age_75_85 age_55_64 age_45_54 age_35_44 age_25_34 age_65_74 hlthwt mi_rec midur female white midursq svy linearized, subpop(if nl_oop!=.): regress nl_oop chd_rec bmi_c agecen chol_rec midursq midur female white nonhis unins wid nvrmd sep midinc highinc lowPr Educ_Col Educ_HS ang_rec miagesq ohrt_rec 40) Breast Cancer (Out of Pocket Expenditure)
generate brst2534=brst_rec*age_25_34 if brst_rec !=.
generate brstage3544=brst_rec*age_35_44 if brst_rec !=.
generate brstage4554=brst_rec*age_45_54 if brst_rec !=.
generate brstage5564=brst_rec*age_55_64 if brst_rec !=.
generate brstage6574=brst_rec*age_65_74 if brst_rec !=.
generate brstage7585=brst_rec*age_75_85 if brst_rec !=.
generate brsthlth=brst_rec*hlthwt if hlthwt !=.
generate brstob=brst_rec*ovob if ovob !=.
generate brstdurdursq=brst_rec*brstdur*brstdursq if brst_rec !=.
generate brstBMI=brst_rec*bmi_c if bmi_c !=.
generate AgelastSq=agelast*agelast
generate hbpAgelastsq=hbp_rec*AgelastSq if hbp_rec !=.
generate hbpBMI=hbp_rec*bmi_c if hbp_rec !=.
generate BMISQ=bmi_c*bmi_c if bmi_c !=.
generate brstBMI=brst_rec*bmi_c if bmi_c !=.
generate brstdurdursq=brst_rec*brstdur*brstdursq if brst_rec !=.
generate brstInterbrstrem=brst_rec*brst_rem if brst_rec !=.
generate brst_rem=brstrems==1 if brstrems>0
recode brst_rem (.=-1) if brstrems==-1 svy linearized, subpop(if nl_oop!=.): regress nl_oop ovob brst_rec brstdur brstdursq age_25_34 age_35_44 brst4554 age_55_64 age_65_74 age_75_85 brst3544 brst6574 brst7585 svy linearized, subpop(if nl_oop!=.): regress nl_oop hlthwt brst_rec brstdur brstdursq age_25_34 age_35_44 brst4554 age_55_64 age_65_74 age_75_85 brst3544 brst6574 svy linearized: logit if_oop age_75_85 age_55_64 age_45_54 age_35_44 age_65_74 age_25_34 brst_rec ovob brstob nvrmd hisp pub_ins Educ_Col female white svy linearized: logit if_oop age_75_85 age_55_64 age_45_54 age_35_44 age_65_74 age_25_34 brst_rec hlthwt brsthlth nvrmd hisp pub_ins Educ_Col female white svy linearized, subpop(if nl_oop!=.): regress nl_oop brst_rec brstdur brstdursq white female unins Educ_Col nonhis Educ_HS nvrmd agelast lowPr midinc highinc bmi_c AgelastSq calung_rec caliver_rec 41) High Cholesterol (Out of Pocket Expenditure)
   generate chol1824=chol_rec*age_18_24 if chol_rec !=.
   generate chol2534=chol_rec*age_25_34 if chol_rec !=.
   generate chol3544=chol_rec*age_35_44 if chol_rec !=.
   generate chol4554=chol_rec*age_45_54 if chol_rec !=.
   generate chol5564=chol_rec*age_55_64 if chol_rec !=.
   generate chol6574=chol_rec*age_65_74 if chol_rec !=.
   generate chol7585=chol_rec*age_75_85 if chol_rec !=.
   generate cholob=chol_rec*ovob if chol_rec !=.
   generate cholhlth=hlthwt*chol_rec if chol_rec !=.
   svy linearized, subpop(if nl_oop!=.): regress nl_oop age_25_34 age_35_44 age_45_54 age_55_64 age_75_85 age_65_74 cholob choldur choldursq ovob chol_rec
   svy linearized, subpop(if nl_oop!=.): regress nl_oop age_25_34 age_35_44 age_45_54 age_55_64 age_75_85 age_65_74 hlthwt chol_rec cholhlth choldur choldursq
   svy linearized: logit if_oop hlthwt age_75_85 age_55_64 age_45_54 age_35_44 age_25_34 age_65_74 choldur choldursq chol_rec cholhlth chol2534 chol7585 female white nvrmd
   svy linearized: logit if_oop ovob age_75_85 age_55_64 age_45_54 age_35_44 age_25_34 age_65_74 choldur choldursq chol_rec cholob chol2534 chol6574 chol7585
   svy linearized, subpop(if nl_oop!=.): regress nl_oop agelast cholbmi choldur choldursq chol_rec bmi_c female white nvrmd sep Educ_Col Educ_HS lowPr midinc highinc unins pub_ins nonhis
42) Mental Health (Out of Pocket Expenditure)
   generate ment7585=ment_pf*age_75_85 if ment_pf !=.
   generate ment6574=ment_pf*age_65_74 if ment_pf !=.
   generate ment5564=ment_pf*age_55_64 if ment_pf !=.
   generate ment4554=ment_pf*age_35_44 if ment_pf !=.
   generate ment3544=ment_pf*age_35_44 if ment_pf !=.
   generate ment2534=ment_pf*age_25_34 if ment_pf !=.
   generate ment1824=ment_pf*age_18_24 if ment_pf !=.
   generate mentob=ment_pf*ovob if ovob !=.
   generate menthlth=ment_pf*hlthwt if hlthwt !=.
   svy linearized, subpop(if nl_oop!=.): regress nl_oop age_75_85 age_55_64 age_45_54 age_35_44 age_25_34 age_65_74 mentob ment7585
   svy linearized: logit if_oop age_65_74 age_75_85 age_55_64 age_45_54 age_35_44 age_25_34 mentob ment4554
   svy linearized, subpop(if nl_oop!=.): regress nl_oop age_75_85 age_55_64 age_45_54 age_35_44 age_25_34 age_65_74 menthlth ment3544 ment7585
   svy linearized: logit if_oop age_65_74 age_75_85 age_55_64 age_45_54 age_35_44 age_25_34 menthlth ment5564 ment2534
43) Destringing Variables
   destring cccodex, gen(new)
   rename new new_ccodex
   destring icd9codx, gen(new)
   rename new new_icd9codx
44) Multiple Imputation
   mi set wide
   mi register imputed brst1824 choldursq choldur brst7585 brst6574 brst5564 brst4554 brst3544 brstdur2534 brstdursq brstdur brst_rec ment_pf arthdursq arthdur midursq midur hbcldursq hbcldur dbcldursq dbcldur chddursq chddur unsp_arth os_arth rh_arth ang_rec mi_rec chd_rec chol_rec Educ_Col Educ_HS bmi_c diab_rec can_rec hbp_rec arth_rec mi register passive if_oop nl_oop if_pub nl_pub if_prv nl_prv ovob undwt hlthwt mi impute chained (pmm) os_arth rh_arth ang_rec unsp_arth mi_rec chd_rec chol_rec diab_rec can_rec hbp_rec brst_rec Educ_Col Educ_HS bmi_c choldur choldursq brst7585 brst6574 brst5564 brst4554 brst3544 brstdur2534 brstdur brstdursq arthdursq arthdur midursq midur hbcldur hbcldursq dbcldursq dbcldur chddursq chddur=agelast female Other_Race white lowPr midinc highinc pub_ins unins hisp wid div sep nvrmd prv_exp pub_exp OOP_all, add(25) rseed(345) force nomonotone)
45) Children and BMI
   generate undwt=age=>59.5 & age<=102.5 & BMI<=13.6|
   age=>103.5 & age<=114.5 & BMI<=13.8|
   age>=115.5 & age<=123.5 & BMI<=14.0|
   age>=124.5 & age<=130.5 & BMI<=14.2|
   age>=131.5 & age<=137.5 & BMI<14.4|
   age>=138.5 & age<=145.5 & BMI<=14.7|
   age>=146.5 & age<=153.5 & BMI<=15.0|
   age>=154.5 & age<=160.5 & BMI<15.3|
   age>=161.5 & age<=167.5 & BMI<=15.6|
   age>=168.5 & age<=174.4 & BMI<=15.9|
   age>=175.5 & age<=180.5 & BMI<=16.2|
   age>=181.5 & age<=187.5 & BMI<=16.5|
   age>=188.5 & age<=193.5 & BMI<=16.8|
   age>=194.5 & age<=199.5 & BMI<=171.1
   if sex==male
   mi impute chained (regress)bmi_c Educ_Col Educ_HS ment_pf os_arth_rh)arth diab_rec mi_rec
   (pmm) choldur choldursq brst7585 brst6574 brst5564 brst4554 brst3544 brstdur2534 brstdursq brstdur arthdursq arthdur midursq midur hbdur hbcldursq dbcldursq dbcldur chddursq chddur=agelast region10 female Other_Race white lowPr midinc highinc pub_ins unins hisp wid div sep nvrmd pub_exp OOP_all prv_exp, add(10)
46) Recoding for Work Limitations
   generate wlklim_rec=wlklim53==1 if wlklim53>0
   recode wlklim_rec (.=1) if wlklim31==1
   recode wlklim_rec (.=0) if wlklim31==2
   recode wlklim_rec (.=-1) if wlklim31==-1
47) Recoding for Activity Limitations
   generate actlim_rec=actlim53==1 if actlim53>0
   recode actlim_rec (.=1) if actlim31==1
   recode actlim_rec (.=0) if actlim31==2
   recode actlim_rec (.=-1) if actlim31==-1

Where methods described above indicate certain events occurring in certain orders, the ordering of certain events may be modified. Moreover, while a process depicted as a flowchart, block diagram, etc., may describe the operations of the system in a sequential manner, it should be understood that many of the system's operations can occur concurrently.

Techniques consistent with the present disclosure provide, among other features, a system and method to reduce healthcare costs with an incentive-based plan to achieve a healthy body mass index (BMI) and evidence based predictive and differential analysis of relevant compound risks and incremental lifetime expenditures. While various exemplary embodiments of the disclosed system and method have been described above, it should be understood that they have been presented for purposes of example only, not limitation. The various disclosed embodiments are not exhaustive and do not limit the disclosure to the precise forms disclosed. Modifications and variations are possible in light of the above teachings or may be acquired from practicing of the disclosure, without departing from the breadth or scope. The scope of the invention is defined by the claims and their equivalents.

What is claimed is:

1. A method of predicting future healthcare costs for an illness within a cohort of individuals, comprising:
building, by a services platform device of a processing apparatus, a cause-effect relationship and compound effect model based on a plurality of dependent and independent variables and interactions associated with illnesses, wherein the services platform device includes a processor;
harvesting, by a data harvester, a plurality of structured and semi-structured healthcare datasets, including electronic health records, medical health records, and personal health records, from a plurality of healthcare data providers;
aggregating, by a data aggregator of the services platform device, the plurality of structured and semi-structured healthcare datasets that were harvested to produce aggregated healthcare datasets;
performing, by the services platform device, risk assessments using differential and statistical regression analysis on the aggregated healthcare datasets, wherein the risk assessments are based on a first set of variables related to characteristics of an individual and interactions that are expressed as a second set of variables;
estimating, by the services platform device, incremental and lifetime costs associated with illnesses for individuals with a healthy body mass index (BMI) that is less than 24.99 that are with and without an illness, based on the cause-effect relationship and compound effect model; and
estimating, by the services platform device, incremental and lifetime costs associated with illnesses for individuals with an unhealthy BMI that is greater than 25 that are with and without an illness, based on the cause-effect relationship and compound effect model.

2. The method of claim 1, wherein the first set of variables may be defined manually, imported, or computed.

3. The method of claim 1, wherein the interactions associated with illnesses and the interactions expressed as the second set of variables represent a quantitative contextual and evidence based correlation between illnesses, treatments, and the onset and duration of illness.

4. The method of claim 1, wherein expenditures for an individual without the illness condition includes anticipated out-of-pocket payments for preventive measures, insurance premiums, co-payments, deductibles, and co-insurance.

5. The method of claim 1, further comprising:
calculating total expenditures by summing facility and physician direct payments by healthcare insurance providers and out-of-pocket expenses of a beneficiary, and converting the calculated total expenditures to a natural logarithm.

6. The method of claim 5, wherein performing risk assessments using differential regression analysis includes analyzing relationships between the dependent variables, the independent variables, and the natural logarithm.

7. The method of claim 1, wherein the independent variables include at least one of age, BMI, gender, education, race, income, occupation, health conditions designated by International Classification of Diseases/Healthcare Common Procedure Coding System/Current Procedural Terminology codes and onset dates, social history, family history, activities of daily living, activity limitations, vital signs, allergies, medications, bone mineral density, immunizations, bio-markers, genetic disposition, and claims history.

8. The method of claim 1, further comprising:
identifying interactions between (i) disease and age, (ii) disease and BMI, and (iii) disease and onset and duration of illness.

9. The method of claim 8, further comprising:
predicting expenditures for an individual on a basis of the identified interactions.

10. The method of claim 8, wherein the estimating of the incremental and relevant lifetime costs includes (i) predicting expenditures for an individual on a basis of the identified interactions, (ii) predicting a probability of having expenditures using binary logistic regression, and (iii) multiplying the predicted expenditures by the predicted probability.

11. The method of claim 1, further comprising:
predicting a probability of having expenditures using binary logistic regression.

12. The method of claim 1, wherein the associated lifetime costs include a plurality of expenses applicable to one or more treatments associated with one or more illnesses.

13. The method of claim 1, wherein the estimated incremental and lifetime costs associated with the illnesses for individuals with a healthy body mass index that is less than 24.99 that are with and without an illness includes at least out-of-pocket expenses and insurance payments.

14. The method of claim 13, wherein the estimated incremental and lifetime costs associated with the illnesses for individuals with an overweight or obese body mass index that is greater than 25 that are with and without an illness includes at least second out-of-pocket expenses and second insurance payments.

15. The method of claim 1, further comprising: calculating total expenditures by summing facility and physician direct payments by healthcare insurance providers and out-of-pocket expenses of a beneficiary and converting the calculated total expenditures to a natural logarithm, and
wherein the performing of the risk assessments using differential regression analysis includes analyzing relationships between the dependent variables which includes a natural logarithm of the lifetime costs, and the independent variables which include at least one of age, BMI, gender, education, race, income, occupation, health conditions designated by International Classification of Diseases/Healthcare Common Procedure Coding System/Current Procedural Terminology codes and onset dates, social history, family history, activities of daily living, activity limitations, vital signs, allergies, medications, bone mineral density, immunizations, bio-markers, genetic disposition, and claims history.

16. The method of claim 1, wherein the illnesses include at least diabetes, heart disease, stroke, arthritis, mental diseases, high blood pressure, and cancer.

17. The method of claim 1, wherein the estimated incremental and lifetime costs are calculated using a two-part regression model.

18. The method of claim 17, further comprising:
predicting, using a first part of the model, expenditures for the individuals with and without an illness,
using, by the second part of the model, binary logistic regression to predict a probability of having an expenditure among the individuals with and without an illness having the unhealthy BMI,
calculating the predicted expenditure incurred for the individuals having the unhealthy BMI with illnesses by multiplying the predicted probability of having an expenditure from the second part of the model by its predicted expenditure obtained from the first part of the model, and calculating the predicted expenditure incurred for the individuals having the unhealthy BMI without illnesses by multiplying the predicted probability of having an expenditure from the second part of the model by its predicted expenditure obtained from the first part of the model.

19. The method of claim 17, further comprising:

predicting, using a first part of the model, expenditures for the individuals with and without an illness, using, by the second part of the model, binary logistic regression to predict a probability of having an expenditure among the individuals with and without an illness having the healthy BMI, calculating the predicted expenditure incurred for the individuals having the healthy BMI with illnesses by multiplying the predicted probability of having an expenditure from the second part of the model by its predicted expenditure obtained from the first part of the model, and calculating the predicted expenditure incurred for the individuals having the healthy BMI without illnesses by multiplying the predicted probability of having an expenditure from the second part of the model by its predicted expenditure obtained from the first part of the model.

20. The method of claim 17, further comprising:

predicting, by a first part of the model, an expenditure for individuals, using, by the second part of the model, binary logistic regression to predict a probability of having an expenditure among individuals, calculating the predicted expenditure that includes direct payments by healthcare insurance providers for the individuals having the unhealthy BMI with illnesses by multiplying the predicted probability of having an expenditure from the second part of the model by its predicted expenditure obtained from the first part of the model, calculating the predicted expenditure that includes the direct payments by the healthcare insurance providers for the individuals having the healthy BMI with illnesses by multiplying the predicted probability of having an expenditure from the second part of the model by its predicted expenditure obtained from the first part of the model, calculating the predicted expenditure that includes the out-of-pocket expenses of the individuals having the unhealthy BMI with illnesses by multiplying the predicted probability of having an expenditure from the second part of the model by its predicted expenditure obtained from the first part of the model, calculating the predicted expenditure that includes the out-of-pocket expenses of the individuals having the healthy BMI with illnesses by multiplying the predicted probability of having an expenditure from the second part of the model by its predicted expenditure obtained from the first part of the model, calculating the predicted expenditure incurred for the individuals having the unhealthy BMI without illnesses by multiplying the predicted probability of having an expenditure from the second part of the model by its predicted expenditure obtained from the first part of the model, calculating the predicted expenditure incurred for the individuals having the healthy BMI without illnesses by multiplying the predicted probability of having an expenditure from the second part of the model by its predicted expenditure obtained from the first part of the model, and applying the first part and the second part of the model for a plurality of illnesses that may occur for an individual during their lifetime.

* * * * *